(12) United States Patent
Ayoub et al.

(10) Patent No.: US 7,335,802 B2
(45) Date of Patent: Feb. 26, 2008

(54) METHODS OF PREPARING BRANCHED ALIPHATIC ALCOHOLS

(75) Inventors: Paul Marie Ayoub, Amsterdam (NL); Hendrik Dirkzwager, Amsterdam (NL); Brendan Dermot Murray, Houston, TX (US); Steve Clois Sumrow, Katy, TX (US)

(73) Assignee: Shell Oil Company, Houston, TX (US)

( * ) Notice: Subject to any disclaimer, the term of this patent is extended or adjusted under 35 U.S.C. 154(b) by 395 days.

(21) Appl. No.: 10/965,256

(22) Filed: Oct. 14, 2004

(65) Prior Publication Data

US 2005/0101808 A1    May 12, 2005

Related U.S. Application Data

(60) Provisional application No. 60/511,211, filed on Oct. 15, 2003.

(51) Int. Cl.
*C07C 27/22* (2006.01)

(52) U.S. Cl. ............... 568/909; 568/840; 568/698; 558/39

(58) Field of Classification Search ............ 568/909, 568/840
See application file for complete search history.

(56) References Cited

U.S. PATENT DOCUMENTS

| | | | |
|---|---|---|---|
| 2,620,314 A | 12/1952 | Hoekstra | 252/448 |
| 2,930,763 A | 3/1960 | Haensel | 252/441 |
| 3,231,621 A | 1/1966 | Slaugh | 260/604 |
| 3,238,249 A | 3/1966 | Mirviss et al. | 260/505 |
| 3,239,566 A | 3/1966 | Slaugh | 260/604 |
| 3,239,569 A | 3/1966 | Slaugh | 260/632 |
| 3,239,570 A | 3/1966 | Slaugh | 260/632 |
| 3,239,571 A | 3/1966 | Slaugh | 260/632 |
| 3,274,287 A | 9/1966 | Moore et al. | 260/683.3 |
| 3,315,007 A | 4/1967 | Abell, Jr. et al. | 260/683.3 |
| 3,315,008 A | 4/1967 | Abell, Jr. et al. | 260/683.3 |
| 3,400,163 A | 9/1968 | Mason et al. | 260/606.5 |
| 3,420,875 A | 1/1969 | DiSalvo et al. | 260/513 |
| 3,420,893 A | 1/1969 | Faltings et al. | 260/618 |
| 3,428,654 A | 2/1969 | Rubinfeld et al. | 260/327 |
| 3,440,291 A | 4/1969 | Van Winkle et al. | 260/632 |
| 3,442,965 A | 5/1969 | Oldham | 260/671 |
| 3,448,157 A | 6/1969 | Slaugh et al. | 260/604 |
| 3,462,525 A | 8/1969 | Levinsky et al. | 424/56 |
| 3,484,498 A | 12/1969 | Berg | 260/671 |
| 3,488,158 A | 1/1970 | Bentley et al. | 23/258.5 |
| 3,492,364 A | 1/1970 | Jones et al. | 260/671 |
| 3,496,203 A | 2/1970 | Morris et al. | 260/439 |
| 3,496,204 A | 2/1970 | Morris et al. | 260/439 |
| 3,501,515 A | 3/1970 | Van Winkle et al. | 260/439 |
| 3,506,580 A | 4/1970 | Rubinfeld et al. | 252/138 |
| 3,527,818 A | 9/1970 | Mason et al. | 260/632 |
| 3,579,537 A | 5/1971 | Rubinfeld et al. | 260/327 |
| 3,676,523 A | 7/1972 | Mason | 260/683 |
| 3,686,351 A | 8/1972 | Mason | 260/683.15 |
| 3,737,475 A | 6/1973 | Mason | 260/683.15 |
| 3,745,112 A | 7/1973 | Ruasch | 208/139 |
| 3,907,909 A | 9/1975 | Macaluso, Sr. et al. | 260/632 HF |
| 4,016,245 A | 4/1977 | Plank et al. | 423/328 |
| 4,020,121 A | 4/1977 | Kister et al. | 260/683.15 |
| 4,251,499 A | 2/1981 | Nanne et al. | 423/329 |
| 4,375,573 A | 3/1983 | Young | 585/467 |
| 4,430,517 A | 2/1984 | Imai et al. | 585/660 |
| 4,438,287 A | 3/1984 | Imai | 568/909 |
| 4,506,032 A | 3/1985 | Imai et al. | 502/223 |
| 4,578,259 A | 3/1986 | Morimoto et al. | 423/329 |
| 4,579,986 A | 4/1986 | Sie | 585/324 |
| 4,795,623 A | 1/1989 | Evans | 423/328 |
| 4,942,027 A | 7/1990 | Evans | 423/328 |
| 4,959,491 A | 9/1990 | Threlkel | 562/94 |
| 5,012,021 A | 4/1991 | Vora et al. | 585/315 |
| 5,112,519 A | 5/1992 | Giacobbe et al. | 252/174.21 |
| 5,169,824 A | 12/1992 | Saleh et al. | 502/259 |
| 5,196,624 A | 3/1993 | Threlkel et al. | 585/513 |
| 5,196,625 A | 3/1993 | Threlkel et al. | 585/513 |
| 5,276,990 A | 1/1994 | Ramirez | 43/17.5 |
| 5,292,990 A | 3/1994 | Kantner et al. | 585/820 |
| 5,371,308 A | 12/1994 | Gosselink et al. | 585/251 |
| 5,510,306 A | 4/1996 | Murray | 502/64 |
| 5,523,503 A | 6/1996 | Funk et al. | 585/446 |
| 5,648,584 A | 7/1997 | Murray | 585/666 |
| 5,648,585 A | 7/1997 | Murray et al. | 585/671 |
| 5,780,694 A | 7/1998 | Singleton | 568/909 |
| 5,821,188 A * | 10/1998 | de Agudelo et al. | 502/74 |
| 5,849,960 A | 12/1998 | Singleton et al. | 568/909 |
| 5,849,972 A | 12/1998 | Vicari et al. | 585/531 |
| 5,985,238 A | 11/1999 | Pasquale et al. | 423/706 |

(Continued)

FOREIGN PATENT DOCUMENTS

EP    0055529    7/1982

(Continued)

OTHER PUBLICATIONS

U.S. Appl. No. 10/153,995, filed May 23, 2002.

(Continued)

*Primary Examiner*—Rosalynd Keys

(57) ABSTRACT

Systems and methods to produced branched aliphatic alcohols are described. Systems may include a dehydrogenation-isomerization unit, an olefin dimerization unit, an olefin isomerization unit, a hydroformylation unit, a dehydrogenation unit, a hydrogenation unit and/or combinations thereof. Methods for producing branched aliphatic alcohols may include isomerization of olefins in a process stream. The isomerized olefins may be hydroformylated to produce aliphatic alcohols. After hydroformylation of the aliphatic alcohols, unreacted components from the hydroformylation process may be separated from the aliphatic alcohols products. The unreacted components from the hydroformylation process may be recycled back into the main process stream or sent to other processing units. Addition of multiple streams to the units may be performed to control reaction conditions in the units.

88 Claims, 8 Drawing Sheets

U.S. PATENT DOCUMENTS

| | | | |
|---|---|---|---|
| 6,008,181 A | 12/1999 | Cripe et al. | 510/426 |
| 6,015,781 A | 1/2000 | Vinson et al. | 510/302 |
| 6,020,303 A | 2/2000 | Cripe et al. | 510/503 |
| 6,046,152 A | 4/2000 | Vinson et al. | 510/428 |
| 6,060,443 A | 5/2000 | Cripe et al. | 510/426 |
| 6,087,309 A | 7/2000 | Vinson et al. | 510/125 |
| 6,111,158 A | 8/2000 | Marinangeli et al. | 585/467 |
| 6,133,222 A | 10/2000 | Vinson et al. | 510/428 |
| 6,133,492 A | 10/2000 | Anantaneni | 585/456 |
| 6,150,322 A | 11/2000 | Singleton et al. | 510/426 |
| 6,187,981 B1 | 2/2001 | Marinangeli et al. | 585/323 |
| 6,222,077 B1 | 4/2001 | Singleton | 568/909 |
| 6,225,518 B1 | 5/2001 | Sohn et al. | 585/826 |
| 6,320,080 B2 | 11/2001 | Connor | 568/28 |
| 6,326,348 B1 | 12/2001 | Vinson et al. | 510/428 |
| 6,388,162 B1 | 5/2002 | Himelfarb et al. | 585/809 |
| 6,392,109 B1 | 5/2002 | O'Rear et al. | 585/323 |
| 6,414,199 B1 | 7/2002 | Saruwatari | 568/728 |
| 6,433,207 B1 | 8/2002 | Connor | 558/31 |
| 6,448,435 B1 | 9/2002 | Jacobson et al. | 562/39 |
| 6,448,458 B1 | 9/2002 | Marinangeli | 585/24 |
| 6,462,215 B1 | 10/2002 | Jacobson et al. | 558/41 |
| 6,492,568 B1 | 12/2002 | Murray et al. | 568/909 |
| 6,515,169 B1 | 2/2003 | Lawson et al. | 562/93 |
| 6,566,566 B1 | 5/2003 | Maas et al. | 568/909 |
| 6,657,092 B2 | 12/2003 | Dirkzwager et al. | 568/909 |
| 6,670,516 B1 | 12/2003 | Marinangeli et al. | 585/323 |
| 6,737,553 B1 | 5/2004 | Maas et al. | 568/909 |
| 6,737,555 B1 | 5/2004 | Maas et al. | 585/531 |
| 6,765,106 B2 | 7/2004 | Fenouil et al. | 558/41 |
| 6,770,191 B2 | 8/2004 | Ansorge et al. | 208/67 |
| 6,852,898 B2 | 2/2005 | Schulz et al. | 585/531 |
| 6,906,230 B1 | 6/2005 | Maas et al. | 568/909 |
| 2002/0004621 A1 | 1/2002 | Xu et al. | 585/260 |
| 2002/0087040 A1 | 7/2002 | Marchionna et al. | 585/331 |
| 2003/0120118 A1 | 6/2003 | Betts et al. | 568/451 |
| 2004/0030209 A1 | 2/2004 | Narbeshuber et al. | 585/323 |

FOREIGN PATENT DOCUMENTS

| | | |
|---|---|---|
| EP | 0103981 | 3/1984 |
| EP | 0211381 A1 | 2/1987 |
| EP | 0583836 | 2/1994 |
| EP | 0668342 | 8/1995 |
| GB | 1601818 | 6/1977 |
| WO | 97/38957 | 10/1997 |
| WO | 98/23566 | 6/1998 |
| WO | 00/12451 | 3/2000 |
| WO | 00/39058 | 7/2000 |
| WO | 01/85654 A2 | 11/2001 |
| WO | 01/85655 A2 | 11/2001 |
| WO | 02/064532 A2 | 8/2002 |

OTHER PUBLICATIONS

U.S. Appl. No. 10/075,682. filed Mar. 6, 2003.
U.S. Appl. No. 10/167,209, filed Jun. 11, 2002.
Flanigen et al., "Aluminophosphate Molecular Sieves and the Periodic Table," *New Developments in Zeolite Science Technology*, 1986, Kodansha Ltd., Tokyo, Japan, pp. 103-112.
"Alcohols, Higher Aliphatic," *Kirk Othmer Encyclopedia of Chemical Technology*, 2000, Fourth Edition, John Wiley & Sons, pp. 865-913.
Edward J. Wickson, Editor, "Monohydric Alcohols; Manufacture, Applications and Chemistry," American Chemical Society Symposium Series 159, 1981, pp. 72-164.
"Sasol Detergent Alcohols," Preliminary Sasol R&D Technical Bulletin, Nov. 25, 1996, pp. 1-13, XP002932342.
International Search Report for PCT/US2004/034080 of Mar. 4, 2005.
Written Opinion for PCT/US2004/034080 of Mar. 4, 2005.
International Search Report for PCT/US2004/033899 of Feb. 2, 2005.
Written Opinion for PCT/US2004/033899 of Feb. 2, 2005.
International Search Report for PCT/US2004/034036 of Apr. 12, 2005.
Written Opinion for PCT/US2004/034036 of Apr. 12, 2005.
International Search Report for PCT/US2004/034081 of Apr. 13, 2005.
Written Opinion for PCT/US2004/034081 of Apr. 13, 2005.
International Search Report for PCT/US2004/034037 of Apr. 12, 2005.
Written Opinion for PCT/US2004/034037 of Apr. 12, 2005.
International Search Report for PCT/US2004/034035 of Apr. 15, 2005.
Written Opinion for PCT/US2004/034035 of Apr. 15, 2005.
International Search Report for PCT/US2004/034008 of Apr. 25, 2005.
Written Opinion for PCT/US2004/034008 of Apr. 25, 2005.

* cited by examiner

METHODS OF PREPARING BRANCHED ALIPHATIC ALCOHOLS

CROSS REFERENCE TO RELATED APPLICATION

This application claims priority to U.S. Provisional Application Ser. No. 60/511,211 filed Oct. 15, 2003, the entire disclosure of which is herein incorporated by reference.

BACKGROUND OF THE INVENTION

1. Field of Invention

The present invention generally relates to systems and methods for preparing aliphatic alcohols. More particularly, embodiments described herein relate to systems and methods for preparing branched aliphatic alcohols.

2. Description of Related Art

Aliphatic alcohols are important compounds that may be used in a variety of applications or converted to other chemical compounds (e.g., surfactants, sulfates). Surfactants may be used in a variety of applications (e.g., detergents, soaps, oil recovery).

The structural composition of the aliphatic alcohol may influence the properties of the surfactant and/or detergent (e.g., water solubility, biodegradability and cold water detergency) produced from the aliphatic alcohol. For example, water solubility may be affected by the linearity of the aliphatic portion of the aliphatic alcohol. As the linearity of the aliphatic portion increases, the hydrophilicity (i.e., affinity for water) of the aliphatic alcohol surfactant may decrease. Thus, the water solubility and/or detergency performance of the aliphatic alcohol surfactant may decrease. Incorporating branches into the aliphatic portion of the aliphatic alcohol surfactant may increase the cold-water solubility and/or detergency of the aliphatic alcohol surfactant. Biodegradability, however, of the aliphatic alcohol surfactants may be reduced if the branches in the aliphatic portion of the alcohol surfactant include a high number of quaternary carbons. Incorporation of branches with a minimum number of quaternary carbon atoms into the aliphatic portion of the aliphatic alcohol surfactant may increase cold-water solubility and/or detergency of the alcohol surfactants while maintaining the biodegradability properties of the detergents.

The aliphatic portion of an aliphatic alcohol used to manufacture a surfactant may include one or more aliphatic alkyl groups as branches. Aliphatic alkyl groups that may form branches in the aliphatic portion may include methyl, ethyl, propyl or higher alkyl groups. Quaternary and tertiary carbons may be present when the aliphatic portion is branched. The number of quaternary and tertiary carbons may result from the branching pattern in the aliphatic portion. As used herein, the phrase "aliphatic quaternary carbon atom" refers to a carbon atom that is not bound to any hydrogen atoms.

U.S. Pat. No. 5,112,519 to Giacobbe et al., entitled "Process for Production of Biodegradable Surfactants and Compositions Thereof," which is incorporated by reference as if fully set forth herein, describes the manufacture of a surfactant by oligomerizing $C_3$ and $C_4$ olefins.

U.S. Pat. No. 6,222,077 to Singleton et al., entitled "Dimerized Alcohol Compositions and Biodegradable Surfactants Made Therefrom Having Cold Water Detergency", which is incorporated by reference as if fully set forth herein, describes a process to manufacture linear alcohols by dimerizing an olefin feed comprising $C_6$-$C_{10}$ linear olefins to obtain $C_{12}$-$C_{20}$ olefins. The dimerized olefins may be converted to alcohols by hydroformylation.

U.S. Pat. No. 5,849,960 to Singleton et al. entitled "Highly Branched Primary Alcohol Compositions, and Biodegradable Detergents Made Therefrom" and U.S. Pat. No. 6,150,322 to Singleton et al., entitled "Highly Branched Primary Alcohol Compositions, and Biodegradable Detergents Made Therefrom," both of which are incorporated by reference as if fully set forth herein, describe processes to manufacture branched primary alcohol compositions.

SUMMARY

In an embodiment, aliphatic alcohols may be produced by a method that includes dehydrogenation of paraffins to olefins and isomerization of the olefins in a dehydrogenation-isomerization unit. A process feed stream entering a dehydrogenation-isomerization unit may include linear olefins and paraffins having an average carbon number from 7 to 18. In an embodiment, a process feed stream entering a dehydrogenation-isomerization unit includes linear olefins and paraffins having an average carbon number from 10 to 17. As used herein, the phrase "carbon number" refers to the total number of carbon atoms in a molecule. The process feed stream entering a dehydrogenation-isomerization unit, in some embodiments, is derived from a Fischer-Tropsch process.

At least a portion of the paraffins in the feed stream may be dehydrogenated to form olefins in the dehydrogenation-isomerization unit. At least a portion of the resulting olefins and at least a portion of the olefins that were already present in the feed stream may also be isomerized in the dehydrogenation-isomerization unit. An isomerization process converts linear olefins (e.g., unbranched olefins) into branched olefins. The isomerized olefins may be hydroformylated to produce aliphatic alcohols. After hydroformylation of the olefins, unreacted components from the hydroformylation process may be separated from the aliphatic alcohol products. Paraffins and unreacted olefins in the separated stream may be recycled back into the dehydrogenation-isomerization unit.

Process conditions in the dehydrogenation-isomerization unit may be such that the resulting branched olefins have an average number of branches per olefin molecule from about 0.7 to about 2.5. The branched olefins may include, but are not limited to, methyl and/or ethyl branched olefins. The isomerization process may produce branched olefins that include less than 0.5 percent of quaternary aliphatic carbon atoms. The dehydrogenation-isomerization unit may include a catalyst that has two functions, to dehydrogenate the paraffins to olefins and to isomerize the olefins into branched olefins.

In an embodiment, a dehydrogenation-isomerization unit may include a plurality of zones. The plurality of zones may include a first reaction zone and a second reaction zone. The first reaction zone may be a dehydrogenation zone. The second reaction zone may be an isomerization zone. A hydrocarbon stream, containing olefins and paraffins, may enter the dehydrogenation zone. At least a portion of the paraffins in the hydrocarbon stream may be dehydrogenated to olefins to produce a stream enriched in olefins. The enriched olefin stream may be passed into the isomerization zone. In the isomerization zone, at least a portion of the olefins in the enriched olefin stream may be isomerized to branched olefins. The branched olefins may be converted to aliphatic alcohols by hydroformylation. After hydroformylation of the olefins, a paraffins and unreacted olefins stream may be separated from the produced aliphatic alcohol products. The paraffins and unreacted olefins stream may be recycled by directing at least a portion of the paraffins and unreacted olefins stream back into the dehydrogenation-isomerization unit and/or into a stream entering the dehydrogenation-isomerization unit.

In certain embodiments, a feed stream is fed into a dimerization unit that produces dimerized olefins. The produced dimerized olefins may include branched dimerized olefins. A process feed stream entering a dimerization unit is derived, in some embodiments, from a Fischer-Tropsch process. In an embodiment, produced dimerized olefins may be separated from the unreacted components after leaving the dimerization unit. The unreacted components, in some embodiments, may be recycled back into the dimerization unit. The produced dimerized olefins may be converted to aliphatic alcohols. In some embodiments, dimerized olefins may be hydroformylated to produce aliphatic alcohols. After hydroformylation of the dimerized olefins, at least a portion of unreacted components from the hydroformylation process may be separated from the produced aliphatic alcohol products.

At least a portion of the unreacted components and the produced dimerized olefins may be separated to produce an unreacted hydrocarbon stream and a produced dimerized olefins stream. At least a portion of the unreacted hydrocarbon stream may be recycled to the dimerization unit.

Process conditions in the dimerization unit may be such that the resulting branched olefins have an average number of branches per olefin molecule from about 0.7 to about 2.5. The branched olefins may include, but are not limited to, methyl and/or ethyl branched olefins. A dimerization unit may produce branched olefins that include less than 0.5 percent of quaternary carbon atoms. In an embodiment, a feed stream entering the dimerization unit includes alpha-olefins having an average carbon number from 4 to 9. The branched olefins produced from the dimerization of alpha-olefins having an average carbon number from 4 to 9 will have an average carbon number from 8 to 18.

In an embodiment, an isomerization unit may be used to produce branched olefins. In an embodiment, at least a portion of the product stream exiting a dimerization unit may be combined with at least a portion of the product stream exiting an isomerization unit and the combined stream directed to a hydroformylation unit. At least a portion of the olefins in the combined stream may be hydroformylated in the hydroformylation unit to produce aliphatic alcohols. After hydroformylation of the olefins, at least a portion of unreacted components from the hydroformylation process may be separated from the aliphatic alcohol products. At least a portion of the unreacted components may be separated.

Isomerization of olefins in a process stream may occur in an isomerization unit. In certain embodiments, a process feed stream entering an isomerization unit is derived from a Fischer-Tropsch process. At least a portion of the linear olefins in a process feed stream may be isomerized to branched olefins in the isomerization unit. The resulting branched olefins may have an average number of branches per olefin molecule from about 0.7 to about 2.5. The branched olefins may include, but are not limited to, methyl and/or ethyl branched olefins. The isomerization process may produce branched olefins that include less than 0.5 percent of aliphatic quaternary carbon atoms.

In an embodiment, one or more hydrocarbon streams may be combined with the feed stream entering an isomerization unit. The hydrocarbon stream may be mixed with the feed stream to alter the concentration of the olefins entering the isomerization unit. After the feed stream is processed in the isomerization unit, the resulting branched olefin-containing stream is passed into a hydroformylation unit. One or more hydrocarbon streams may be combined with the branched olefin-containing stream to alter the concentration of olefins entering the hydroformylation unit. After hydroformylation of the olefins, unreacted components from the hydroformylation process may be separated from the aliphatic alcohol products. Paraffins and unreacted olefins in the separated stream may be sent to a dehydrogenation unit.

Dehydrogenation of paraffins may occur in a dehydrogenation unit. In an embodiment, at least a portion of a paraffins and unreacted olefins stream may enter a dehydrogenation unit. In the dehydrogenation unit, at least a portion of the paraffins in the paraffins and unreacted olefins stream may be dehydrogenated to produce olefins. At least a portion of the produced olefins may exit the dehydrogenation unit to form an olefinic hydrocarbon stream. The resulting olefinic hydrocarbon stream from the dehydrogenation process may be recycled back into the isomerization unit and/or into a stream entering the isomerization unit.

In an embodiment, a feed stream containing olefins and paraffins may be processed in a hydrogenation unit. A process feed stream entering a hydrogenation unit is derived, in some embodiments, from a Fischer-Tropsch process. In the hydrogenation unit at least a portion of the olefins in the feed stream may be hydrogenated to form paraffins. The resulting paraffinic feed stream may be fed into a dehydrogenation unit. At least a portion of the paraffins may be dehydrogenated to form an olefinic hydrocarbons feed stream. The resulting olefinic hydrocarbon stream from the dehydrogenation process may be introduced into a dimerization unit and/or an isomerization unit. At least a portion of the resulting olefins may be hydroformylated to produce aliphatic alcohols.

In an embodiment, a feed stream containing olefins and paraffins may be processed in a hydrogenation unit. A process feed stream entering a hydrogenation unit is derived, in some embodiments from a Fischer-Tropsch process. In the hydrogenation unit at least a portion of the olefins in the feed stream may be hydrogenated to form paraffins. The resulting paraffinic feed stream may be fed into a dehydrogenation-isomerization unit. At least a portion of the paraffins in the feed stream may be dehydrogenated to form olefins. The dehydrogenation-isomerization unit may also isomerize at least a portion of the resulting olefins and at least a portion of the olefins that were already present in the feed stream. The olefins produced from the dehydrogenation-isomerization unit may be hydroformylated to produce aliphatic alcohols. At least a portion of the aliphatic alcohols may have a branched aliphatic structure.

In certain embodiments, at least a portion of the aliphatic alcohols may be sulfated to form aliphatic sulfates. In some embodiments, aliphatic sulfates may include branched alkyl groups.

In certain embodiments, at least a portion of the produced aliphatic alcohols may be oxyalkylated to form oxyalkyl alcohols. In some embodiments, oxyalkyl alcohols may include branched alkyl groups. In some embodiments, at least a portion of the produced branched aliphatic alcohols may be ethoxylated to form branched ethoxyalkyl alcohols. At least a portion of the oxyalkyl alcohols may be sulfated to from oxyalkyl sulfates. In some embodiments, oxyalkyl sulfates may include branched alkyl groups.

BRIEF DESCRIPTION OF THE DRAWINGS

Advantages of the present invention will become apparent to those skilled in the art with the benefit of the following detailed description of embodiments and upon reference to the accompanying drawings, in which.

Figure 1:
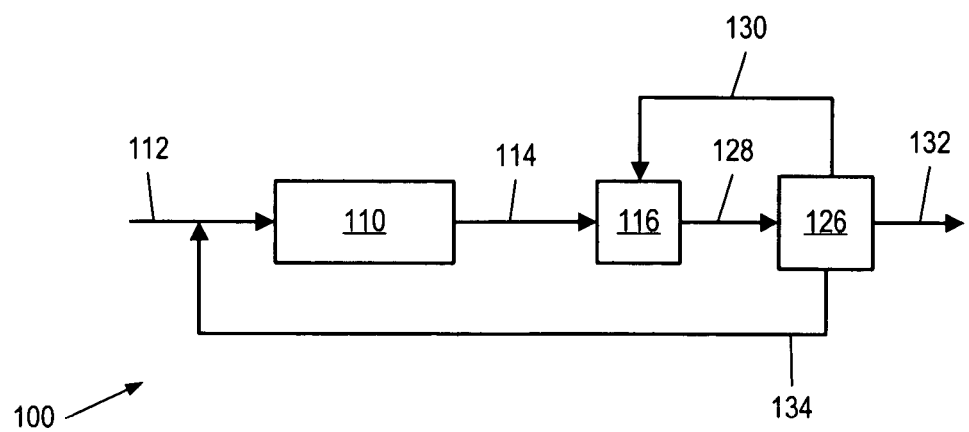
FIG. 1 depicts a schematic diagram of an embodiment of a system for producing branched aliphatic alcohols using a dehydrogenation-isomerization unit.

While the invention is susceptible to various modifications and alternative forms, specific embodiments thereof are shown by way of example in the drawing and will herein be described in detail. It should be understood that the drawings and detailed description thereto are not intended to limit the invention to the particular form disclosed, but on the contrary, the intention is to cover all modifications, equivalents, and alternatives falling within the spirit and scope of the present invention as defined by the appended claims.

DETAILED DESCRIPTION

Hydrocarbon products may be synthesized from synthesis gas (i.e., a mixture of hydrogen and carbon monoxide) using a Fischer-Tropsch process. Synthesis gas may be derived by partial combustion of petroleum (e.g., coal, hydrocarbons), by reforming of natural gas or by partial oxidation of natural gas. The Fischer-Tropsch process catalytically converts synthesis gas into a mixture of products that includes saturated hydrocarbons, unsaturated hydrocarbons and a minor amount of oxygen-containing products. The products from a Fischer-Tropsch process may be used for the production of fuels (e.g., gasoline, diesel oil), lubricating oils and waxes.

Fischer-Tropsch process streams may also be used to prepare commodity products, which have economic value. For example, linear olefins are commodity products that are useful for the production of surfactants. Using a portion of the process stream to produce linear olefins may increase the economic value of a Fischer-Tropsch process stream.

Surfactants derived from branched olefins may have different properties than surfactants derived from linear olefins. For example, surfactants derived from branched olefins may have increased water solubility and/or improved detergency properties compared to surfactants derived from linear olefins. Biodegradable properties of the surfactant, however, may be affected by the presence of quaternary carbon atoms in the branched portion of the surfactant. Surfactants made from branched olefins with a minimum number of quaternary carbon atoms may have similar biodegradable properties to surfactants derived from linear olefins. Production of branched olefins from a Fischer-Tropsch process stream may increase the economic value of the stream. In some embodiments, linear olefins may be converted into branched olefins with a minimum number of quaternary carbon atoms using an isomerization catalyst. Increasing the amount of branched olefins derived from a Fischer-Tropsch process stream may increase the economic value of the process streams.

Methods are described for increasing the amount of branched olefins derived from a process stream that includes certain amount of olefins, thus increasing the economic value of the process stream. Such methods are useful for both Fischer-Tropsch process streams and product streams from other sources that include hydrocarbons.

A hydrocarbon feed stream composition may include paraffins and olefins. At least a portion of the hydrocarbon stream may be made up of linear paraffins and olefins having at least 4 carbon atoms and up to 18 carbon atoms. A hydrocarbon feed stream may be obtained from a Fischer-Tropsch process or from an ethylene oligomerization process. Fischer-Tropsch catalysts and reaction conditions may be selected to provide a particular mix of products in the reaction product stream. For example, a Fischer-Tropsch catalyst and reaction conditions may be selected to increase the amount of olefins and decrease the amount of paraffins and oxygenates in the stream. Alternatively, the catalyst and reaction conditions may be selected to increase the amount of paraffins and decrease the amount of olefins and oxygenates in the stream.

The catalyst used in a Fischer-Tropsch process may be Mo, W, Group VIII compounds or combinations thereof. Group VIII compounds include, but are not limited to, iron, cobalt, ruthenium, rhodium, platinum, palladium, iridium and osmium. Combinations of Mo, W and Group VIII compounds may be prepared in the free metal form. In an embodiment, combinations of Mo, W and Group VIII compounds may be formed as alloys. Combinations of Mo, W and Group VIII compounds may be formed, in some embodiments, as oxides, carbides or other compounds. In other embodiments, combinations of Mo, W and Group VIII compounds may be formed as salts. Iron based and cobalt based catalysts have been used commercially as Fischer-Tropsch catalysts. Ruthenium catalysts tend to favor the formation of high melting waxy species under high-pressure conditions. Synthetic Fischer-Tropsch catalysts may include fused iron. In some embodiments, a fused iron Fischer-Tropsch catalyst may include a promoter (e.g., potassium or oxides on a silica support, alumina support or silica-alumina support). Cobalt metal may also be used in a Fischer-Tropsch catalyst. With the proper selection of supports, promoters and other metal combinations, a cobalt catalyst may be tuned to manufacture a composition enriched in the desired hydrocarbon species. Other catalysts, such as iron-cobalt alloy catalysts, are known for their selectivity toward the production of olefins. Catalysts and combinations for manufacture of hydrocarbon species by a Fischer-Tropsch process are generally known.

While reference is made to a Fischer-Tropsch stream, any stream of olefins and saturated hydrocarbons may be suitable. Many Fischer-Tropsch streams may contain from 5 percent to 80 percent olefins, the remainder being saturated hydrocarbons comprising paraffins and other compounds. The Fischer-Tropsch stream may be separated into several streams. For example, one stream may include hydrocarbons with an average carbon number from 4 to 9 for streams used in a dimerization unit. A second stream may include hydrocarbons with an average carbon number from 7 to 18 for processes that involve an isomerization unit.

In some embodiments, feed streams containing olefins and paraffins are obtained through cracking of paraffin wax or the oligomerization of olefins. Commercial olefin products manufactured by ethylene oligomerization are marketed in the United States by Chevron Phillips Chemical Company, Shell Chemical Company (as NEODENE®) and by British Petroleum. Cracking of paraffin wax to produce alpha-olefin and paraffin feed streams is described in U.S. Pat. No. 4,579,986 to Sie, entitled "Process For The Preparation Of Hydrocarbons" and U.S. patent application Ser. No. 10/153,955 of Ansorge et al., entitled "Process For The Preparation of linear Olefins and Use Thereof To Prepare Linear Alcohols," both of which are incorporated by reference herein. Specific procedures for preparing linear olefins from ethylene are described in U.S. Pat. No. 3,676,523 to Mason, entitled "Alpha-Olefin Production ;" U.S. Pat. No. 3,686,351 to Mason, entitled "Alpha-Olefin Production;" U.S. Pat. No. 3,737,475 to Mason, entitled "Alpha-Olefin Production" and U.S. Pat. No. 4,020,121 to Kister et al., entitled "Oligomerization Reaction System," all of which are incorporated herein by reference. Most of the above-mentioned processes produce alpha-olefins. Higher linear internal olefins may be commercially produced (e.g., chlorination-dehydrochlorination of paraffins, paraffin dehydrogenation, isomerization of alpha-olefins).

In an embodiment, a feed stream is processed to produce a hydrocarbon stream that includes branched olefins. These branched olefins may be converted to branched aliphatic alcohols using various techniques. The feed stream may have a paraffin content range between about 50 percent by weight to about 90 percent by weight of the feed stream. In certain embodiments, a feed stream may have a paraffin content greater than 90 percent by weight paraffins. The feed stream may also include olefins. The olefin content of the feed stream may be between about 10 percent by weight to about 50 percent by weight. In other embodiments, a feed stream may have an olefin content greater than 90 percent by weight olefins.

The composition of the feed stream may include hydrocarbons having an average carbon number ranging from 4 to 30. In an embodiment, an average carbon number of the hydrocarbons in a feed stream may range from 4 to 24. In other embodiments, an average carbon number of the feed stream may range from 4 to 18. An average carbon number of the hydrocarbons in a feed stream may range from 7 to 18 for processes that involve an isomerization unit or a dehydrogenation-isomerization unit. In certain embodiments, an average carbon number of the hydrocarbons in a feed stream may range from 10 to 17 for processes that involve an isomerization unit or a dehydrogenation-isomerization unit. In some embodiments, an average carbon number of hydrocarbons in a feed stream may range from 10 to 13 for processes that involve an isomerization unit or a dehydrogenation-isomerization unit. In other embodiments, an average carbon number of hydrocarbons in a feed stream may range from 14 to 17 for processes that involve an isomerization unit or a dehydrogenation-isomerization unit.

The average carbon number of the hydrocarbons in a feed stream may range from 4 to 9 for processes that use a dimerization unit. In certain embodiments, an average carbon number of the hydrocarbons in a feed stream ranges from 5 to 8 for processes that use a dimerization unit. In some embodiments, an average carbon number of hydrocarbons in a feed stream may range from 5 to 7. In other embodiments, an average carbon number of hydrocarbons in a feed stream may range from 7 to 9. A feed stream may include minor amounts of hydrocarbons having a carbon number that is higher or lower than the desired carbon number range. In some embodiments, a feed stream may be derived from distillation of a process stream that includes a broader range of carbon numbers.

In an embodiment, a feed stream for a dimerization unit and/or an isomerization unit includes mono-olefins and/or paraffins. The mono-olefins may be of a linear or branched structure. The mono-olefins may have an alpha or internal double bond position. The feed stream may include olefins in which 50 percent or more of the olefin molecules present may be alpha-olefins of a linear (straight chain) carbon skeletal structure. In certain embodiments, at least about 70 percent of the olefins are alpha-olefins of a linear carbon skeletal structure. A hydrocarbon stream in which greater than 70 percent of all of the olefin molecules are alpha-olefins of a linear carbon skeletal structure may be used in certain embodiments to convert olefins to aliphatic alcohols.

Such a stream may be derived from a Fischer-Tropsch process. In some embodiments, a feed stream includes olefins in which at least about 50 percent of the olefin molecules present are internal olefins.

Branched chain olefins may be converted to branched aliphatic alcohols (e.g., branched primary alcohols) by a hydroformylation process. "Hydroformylation," as used herein, refers to the production of alcohols from olefins via a carbonylation and a hydrogenation process. Other processes may be used to produce aliphatic alcohols from olefins. Examples of other processes to produce aliphatic alcohols from olefins include, but are not limited to, hydradration, oxidation and hydrolysis, sulfation and hydration, and epoxidation and hydration. The composition of an alcohol product stream may include aliphatic alcohols having an average carbon number ranging from 5 to 31. In an embodiment, an average carbon number of the aliphatic alcohols in an alcohol product stream may range from 7 to 19. In certain embodiments, an average carbon number of the aliphatic alcohols in an alcohol product stream may range from 11 to 18. In some embodiments, an average carbon number of aliphatic alcohols in an alcohol product stream may range from 11 to 14 for processes that involve an isomerization unit or a dehydrogenation-isomerization unit. In other embodiments, an average carbon number of aliphatic alcohols in an alcohol product stream may range from 15 to 18 for processes that involve an isomerization unit or a dehydrogenation-isomerization unit.

For processes that involve a dimerization unit, an average carbon number of aliphatic alcohols in an alcohol product stream may range from 9 to 19. In certain embodiments that involve a dimerization unit, an average carbon number of aliphatic alcohols in an alcohol product stream may range from 11 to 17. In some embodiments that involve a dimerization unit, an average carbon number of aliphatic alcohols in an alcohol product stream may range from 11 to 15. In other embodiments that involve a dimerization unit, an average carbon number of aliphatic alcohols in an alcohol product stream may range from 15 to 19.

In certain embodiments, a first hydrocarbon stream that includes paraffins and olefins may be introduced into a dehydrogenation-isomerization unit. The dehydrogenation-isomerization unit may replace two independent units (e.g., an isomerization unit and a dehydrogenation unit). The dehydrogenation-isomerization unit may dehydrogenate paraffins to olefins and isomerize the resulting olefins and/or initial olefins present in the hydrocarbon stream to branched olefins. In an embodiment, a catalyst may perform the dehydrogenation-isomerization of the hydrocarbons in the first hydrocarbon stream. In certain embodiments, a catalyst may be a single catalyst. The catalyst, in some embodiments, may be a mixture of two catalysts (e.g., a dehydrogenation catalyst and an isomerization catalyst). In other embodiments, two separate catalysts located in different zones or in a stacked bed configuration in one dehydrogenation-isomerization unit may perform the dehydrogenation-isomerization process. As used herein, "a dehydrogenation-isomerization catalyst" may be one or more catalysts.

In certain embodiments, a dehydrogenation-isomerization unit may have several points of entry to accommodate different process streams. The process streams may be from other processing units and/or storage units. Examples of process streams include, but are not limited to, a diluent hydrocarbon stream, and/or other hydrocarbon streams that include olefins and paraffins derived from other processes. As used herein, "entry into the dehydrogenation-isomerization unit" refers to entry of process streams into the dehydrogenation-isomerization unit through one or more entry points.

A first hydrocarbon stream, including a mixture of olefins and paraffins, may be introduced into dehydrogenation-isomerization unit 110 via first conduit 112 as depicted for System 100 in FIG. 1. Hydrocarbons in the first hydrocarbon stream may have an average carbon number from 7 to 18. In certain embodiments, hydrocarbons in the first hydrocarbon stream may have an average carbon number from 10 to 17. In some embodiments, hydrocarbons in the first hydrocarbon stream may have an average carbon number from 10 to 13. In other embodiments, hydrocarbons in the first hydrocarbon stream may have an average carbon number from 14 to 17. In some embodiments, a first hydrocarbon stream includes alpha-olefins. The alpha-olefin content of the first hydrocarbon stream may be greater than 70 percent of the total amount of olefins in the first hydrocarbon stream. In certain embodiments, a first hydrocarbon stream may be produced from a Fischer-Tropsch process.

In dehydrogenation-isomerization unit 110, at least a portion of the paraffins in the first hydrocarbon stream may be dehydrogenated to olefins. At least a portion of the resulting olefins and at least a portion of the olefins that were already present in the feed stream may be isomerized to produce a second hydrocarbon stream. The isomerization process converts linear olefins (i.e., unbranched olefins) into branched olefins.

The catalyst used for the dehydrogenation-isomerization of the first hydrocarbon stream may be based on a zeolite catalyst modified with one or more metals or metal compounds. The catalyst used in dehydrogenation-isomerization unit 110 to treat the olefins in the first hydrocarbon stream may be effective for skeletally isomerizing linear olefins in the process stream into olefins having an average number of branches per olefin molecule chain greater than 0.7. In certain embodiments, an average number of branches per olefin molecule chain may range from about 0.7 to about 2.5. In some embodiments, an average number of branches per olefin molecule chain may range from about 0.7 to about 2.2. In other embodiments, an average number of branches per olefin molecule chain may range from about 1.0 to about 2.2.

The dehydrogenation-isomerization catalyst may contain a zeolite having at least one channel with a crystallographic free channel diameter greater than 4.2 Å and less than 7 Å, measured at room temperature. As used herein, "channel diameter or size" refers to an effective channel diameter or size for diffusion. The zeolite may have no channels present that have a free channel diameter greater than 7 Å. The catalyst may contain at least one channel having a crystallographic free diameter at the entrance of the channel greater than 4.2 Å and less than 7 Å. The catalyst may not have a channel with a diameter at the entrance, which exceeds the 7 Å upper limit of the range. Zeolites possessing channel diameters greater than 7 Å may be susceptible to undesirable olefin by-products (e.g., aromatization, oligomerization, alkylation, coking). In some embodiments, a zeolite may not contain a channel having a free diameter along either of the x or y planes of greater than 4.2 Å. A small channel size may prevent diffusion of the olefin into and/or out of the channel pore once the olefin becomes branched. A zeolite may have at least one channel with a free diameter of the channel within a range of greater than 4.2 Å and less than 7 Å.

In an embodiment, an olefin molecule, due to its high carbon chain length, may not have to enter into the zeolite channel, diffuse through, and exit the other end of the channel. The rate of branching seen when passing the olefin across the zeolite may not correspond to the theoretical rate of branching if each olefin molecule were to pass through the channels. Most of the olefins may partially penetrate the channel for a distance effective to branch the portion of the chain within the channel and subsequently withdraw from the channel once isomerized. In an embodiment of a method to produce aliphatic alcohols, olefin molecules in a hydrocarbon stream may predominately have a structure which is branched at the ends of the olefin carbon backbone, and substantially linear towards the center of the molecule, (e.g., at least 25 percent of the carbons at the center are unbranched).

In certain embodiments, a zeolite catalyst structure may contain channels having free diameters greater than 4.2 Å and less than 7 Å along both the x and y planes in the [001] view. Zeolites with the specified channel size may be referred to as medium or intermediate channel zeolites and typically have a 10-T member (or puckered 12-T member) ring channel structure in one view and a 9-T member or less (small pore) in another view, if any. There is no limit to channel numbers or orientation (e.g., parallel, non-interconnecting intersections, or interconnecting at any angle) in the zeolite.

Examples of zeolites with a channel size from about 4.2 Å to 7.0 Å include molecular sieves, ferrierite, AlPO-31, SAPO-11, SAPO-31, SAPO-41, FU-9, NU-10, NU-23, ZSM-12, ZSM-22, ZSM-23, ZSM-35, ZSM-48, ZSM-50, ZSM-57, SUZ-4A, MeAPO-11, MeAPO-31, MeAPO-41, MeAPSO-11, MeAPSO-31, and MeAPSO-41, MeAPSO-46, ELAPO-11, ELAPO-31, ELAPO-41, ELAPSO-11, ELAPSO-31, and ELAPSO-41, laumontite, cancrinite, offretite, hydrogen form of stilbite, the magnesium or calcium form of mordenite and partheite. The isotypic structures of the zeolite frameworks, known under other names, may be considered equivalent. Zeolite framework is described by Flanigen et al.; in "Aluminophosphate Molecular Sieves and the Periodic Table," New Developments in Zeolite Science Technology, 1986, Kodansha Ltd., Tokyo, Japan, which is incorporated by reference herein.

Many natural zeolites such as ferrierite, heulandite and stilbite may feature a one-dimensional pore structure with a pore size at or slightly smaller than about 4.2 Å in diameter. U.S. Pat. No. 4,795,623 to Evans, entitled "Time Effective Method For Preparing Ferrierite" and U.S. Pat. No. 4,942,027 to Evans, entitled "Method for Preparing Ferrierite," both of which are incorporated by reference herein, describe converting channels in natural zeolites to larger channels. Channels in natural zeolites may be converted to zeolites with desired larger channel sizes by removing an associated alkali metal or alkaline earth metal by generally known methods (e.g., ammonium ion exchange, optionally followed by calcination, to yield a zeolite in substantially a hydrogen form). Replacing the associated alkali or alkaline earth metal with the hydrogen form may enlarge the channel diameter. In some embodiments, natural zeolites (e.g., some forms of mordenite) may have a channel size greater than 7 Å. The channel size may be reduced by substituting an alkali metal for larger ions (e.g., a larger alkaline earth metal).

In certain embodiments, zeolites may have a ferrierite isotypic (or homeotypic) framework structure. The prominent structural features of ferrierite found by x-ray crystallography may be parallel channels in the alumino-silicate framework. The parallel channels may have an elliptical cross section. Zeolites having a ferrierite isotypic framework structure are described in European Patent No. 55 529 to Seddon et al., entitled, "Zeolites;" and European Patent No. 103 981 to Whittam, entitled "Zeolites." Zeolites having a ferrierite isotypic framework are also described in U.S. Pat. No. 4,016,245 to Plank et al., U.S. Pat. No. 4,578,259 to Morimoto et al., entitled "Process For Preparing A Crystalline Aluminosilicate;" entitled "Crystalline Zeolite And Method Of Preparing Same" and U.S. Pat. No. 4,375,573 to Young et al., entitled "Selective Production And Reaction of P-Disubstituted Aromatics Over Zeolite ZSM-48," all of which are incorporated by reference as if fully set forth herein.

In an embodiment, a hydrogen form of ferrierite (H-ferrierite) may be considered to be substantially one-dimensional. H-ferrierite may have parallel running channels. H-ferrrierite may have elliptical channels that have free diameters of 4.2 Å by 5.4 Å along the x and y planes in the [001] view. The channels may be large enough to permit entry of a linear olefin and diffusion out of or through the channel of the methyl branched isoolefin. The channels may be small enough to retard coke formation. Methods for preparing various H-ferrierite are described in U.S. Pat. No. 5,985,238 to Pasquale et al., entitled "Process For Preparing Ferrierite;" U.S. Pat. No. 4,251,499 to Nanne et al., entitled "Process For The Preparation Of Ferrierite;" U.S. Pat. No. 4,795,623 to Evans, entitled "Time Effective Method For Preparing Ferrierite" and U.S. Pat. No. 4,942,027 to Evans, entitled "Method for Preparing Ferrierite;" all of which are incorporated by reference herein.

In certain embodiments, a dehydrogenation-isomerization catalyst may be combined with a refractory oxide that serves as a binder material. Suitable refractory oxides include, but are not limited to, natural clays (e.g., bentonite, montmorillonite, attapulgite, and kaolin), alumina, silica, silica-alumina, hydrated alumina, titania, zirconia or mixtures thereof.

Examples of alumina binders may include, but are not limited to, pseudoboehmite, gamma and bayerite aluminas. Alumina binders may be commercially available (e.g., LaRoche Chemicals manufactures VERSAL® aluminas and Sasol manufactures CATAPAL® aluminas). In an embodiment, high-dispersity alumina powders may be used as alumina binders when extrusion is utilized for catalyst preparation. High-dispersity alumina powders may have a dispersity of greater than 50 percent in an aqueous acid dispersion having an acid content of 0.4-milligram equivalents of acid (acetic) per gram of powder. Such high-dispersity aluminas may be exemplified by CATAPAL® alumina manufactured by Sasol.

A weight ratio of zeolite to binder material may range from about 10:90 to about 99.5:0.5. In some embodiments, a weight ratio may range from about 75:25 to about 99:1. In other embodiments, a weight ratio of zeolite to binder material may range from about 80:20 to about 98:2. In certain embodiments, a weight ratio of zeolite to binder material may range from about 85:15 to about 95:5 on an anhydrous basis.

In certain embodiments, a dehydrogenation-isomerization catalyst may be prepared with one or more monocarboxylic acids and/or inorganic acids. In addition to the monocarboxylic and/or inorganic acids, at least one organic acid with at least two carboxylic acid groups ("polycarboxylic acid") may be used. Monocarboxylic acids may have a substituted or unsubstituted hydrocarbyl group having 1 to 20 carbon atoms. The hydrocarbyl group may be aliphatic, cyclic or aromatic. Examples of monocarboxylic acids having 1 to 20 carbon atoms include, but are not limited to, acetic acid, formic acid, propionic acid, butyric acid, caproic acid, glycolic acid, lactic acid, hydroxylbutyric acid, hydroxycyclopentanoic acid, salicylic acid, mandelic acid, benzoic acid and fatty acids. Examples of inorganic acids include, but are not limited to, nitric acid, phosphoric acid, sulfuric acid and hydrochloric acid.

The polycarboxylic acid may, in certain embodiments, be an organic acid with two or more carboxylic acid groups attached through a carbon-carbon bond linkage to a hydrocarbon segment. The linkage may be at any portion of the hydrocarbon segment. The polycarboxylic acid may have a hydrocarbon segment with less than 10 carbon atoms. The hydrocarbon segment may be aliphatic, cyclic or aromatic. The hydrocarbon segment may have zero carbon atoms for oxalic acid with two carboxylic acid groups attached through the carbon-carbon bond. Examples of the polycarboxylic acids include, but are not limited to, tartaric acid, citric acid, malic acid, oxalic acid, adipic acid, malonic acid, galactaric acid, 1,2-cyclopentane dicarboxylic acid, maleic acid, fumaric acid, itaconic acid, phthalic acid, terephthalic acid, phenylmalonic acid, hydroxyphthalic acid, dihydroxyfumaric acid, tricarballylic acid, benzene-1,3,5-tricarboxylic acid, isocitric acid, mucic acid and glucaric acid. The polycarboxylic acids may be any isomers of the above acids. In some embodiments, the polycarboxylic acids may be any stereoisomers of the above acids. In an embodiment, polycarboxylic acids with at least two carboxylic acid groups and at least one hydroxyl group are used. In an embodiment, citric acid, tartaric acid and malic acid may be used as polycarboxylic acids.

Metals incorporated into a dehydrogenation-isomerization catalyst may be metals that promote the oxidation of coke in the presence of oxygen at a temperature greater than 250° C. and the dehydrogenation of paraffins. "Metal(s)," as used herein, refers to metals of a zero oxidation state and/or higher oxidation states (e.g., metal oxides). As used herein, "coke" refers to a product from thermal degradation of larger molecules into smaller molecules.

Metals used in the dehydrogenation-isomerization catalyst may be transition and rare earth metals. Coke oxidation-promoting metals include, but are not limited to, Groups IB, VB, VIB, VIIB, VIII of the transition metal series of the Periodic Table and/or combinations thereof. In certain embodiments, Pd, Pt, Ni, Co, Mn, Ag, Cr and/or combinations thereof may be used in the dehydrogenation-isomerization catalyst. In other embodiments, metal oxides such as, but not limited to, chrome oxide, iron oxide, noble metals, or mixtures thereof may be used as coke-oxidizing compounds in the catalyst.

An amount of the metal introduced may range from about 5 parts per million ("ppm") up to about 15 percent by weight. In certain embodiments, an amount of metal may range from about 5 ppm to about 10 percent by weight. In some embodiments, an amount of metal may range from about 5 ppm to about 5 percent by weight.

Noble metals (e.g., platinum and/or palladium) may be used in smaller amounts of metals than other metals incorporated into a zeolite and/or binder. "Noble metals," as used herein, refers to metals of the group that includes platinum, palladium, iridium, ruthenium, osmium and rhodium. In certain embodiments, an amount of noble metals may range from about 5 ppm to about 2 percent by weight, basis metal, of the final catalyst. In some embodiments, an amount of noble metals may range from about 5 ppm to about 1000 ppm, basis metal, of the final catalyst. In other embodiments, an amount of noble metal(s) may range from about 5 ppm to about 3000 ppm, basis metal, of the final catalyst. An amount of noble metal(s) used in a dehydrogenation-isomerization catalyst may, in certain embodiments, range from about 5 ppm to about 2000 ppm by weight, basis metal, of the final catalyst. An amount of noble metal(s) sufficient to promote regeneration without deteriorating the performance of the catalyst may be in the range from about 30 ppm to about 100 ppm. Higher amounts of platinum and/or palladium (e.g., greater than 2% by weight) may have an adverse effect on the catalyst (e.g., run life, olefin isomerization activity, selectivity).

In an embodiment, zeolite powder and alumina powder may be mixed (e.g., mulled) with water and one or more metal compounds of the catalyst. The resulting mixture may be formed into a pellet. Catalysts prepared by mulling may have superior olefin isomerization performance over catalysts prepared by impregnation. The term "mulling," as used herein, refers to mixing of powders to which sufficient water has been added to form a thick paste and wherein the mixing is accompanied by concomitant shearing of the paste. Commercially available mullers such as the Lancaster Mix Muller and the Simpson Mix Muller may be used.

The pellet may be formed, in some embodiments, by extrusion. One or more peptizing acid (e.g., nitric acid, acetic acid, citric acid or mixtures thereof) may be added to the mixture and optional extrusion aids such as cellulose derivatives (e.g., METHOCEL®F4M, hydroxypropyl methylcellulose, manufactured by The Dow Chemical Company) may be utilized. The amounts of peptizing acid used may be determined by routine experimentation to provide a plastic, extrudable material. The term "pellets," as used herein, refers to any shape or form of consolidated materials.

In certain embodiments, a noble metal such as platinum and/or palladium may be added to the zeolitic catalyst after pelletization. Common metal incorporation methods known to those skilled in the art (e.g., impregnation, noble metal ion exchange and co-mulling) may be used to produce a working catalyst useful in dehydrogenation-isomerization of paraffins. The addition of noble metals to the catalyst may aid in the dehydrogenation reaction of paraffins. Pellets containing noble metals may be calcined at a temperature range from about 250° C. to about 700° C. In certain embodiments, a calcination temperature may range from about 300° C. to about 600° C. In some embodiments, a calcination temperature may range from about 450° C. to about 525° C.

The dehydrogenation-isomerization catalyst may be contacted with the first hydrocarbon stream in dehydrogenation-isomerization unit 110 under a variety of conditions to dehydrogenate paraffins to olefins and isomerize the resulting olefins. In dehydrogenation-isomerization unit 110, reaction temperatures may range from about 300° C. to about 700° C. A reaction temperature, in some embodiments, may range from about 350° C. to about 550° C. A total pressure of dehydrogenation-isomerization unit 110 during the reaction may range from about 0.010 atmosphere (1 kPa) to about 25.0 atmospheres (2534 kPa). In an embodiment, a total pressure of dehydrogenation-isomerization unit 110 during the reaction may range from about 0.010 atmosphere (1 kPa) to about 15.0 atmospheres (1520 kPa). In other embodiments, a total pressure of dehydrogenation-isomerization unit 110 during the reaction may range from about 1 atmosphere (101 kPa) to about 5.0 atmospheres (507 kPa). In order to prevent coking, hydrogen may be fed together with the first hydrocarbon stream. Hydrogen gas and paraffins present in the first hydrocarbon stream may be fed at a hydrogen gas to paraffin molar ratio in the range from about 0.1 to about 20. In certain embodiments, a hydrogen gas to paraffin molar ratio may be in the range from about 1 to about 10.

Residence time in dehydrogenation-isomerization unit 110 may be selected such that conversion level of the paraffins to olefins may be kept below 40 mole percent. In an embodiment, a conversion level ranges from 5 mole percent to 30 mole percent. By keeping the conversion level low, side reactions (e.g., diene formation and cyclization reactions) may be minimized. Olefin conversion may be increased by varying the reaction conditions (e.g., temperature, residence time) as long as side reactions remain below acceptable limits. Olefins produced in dehydrogenation-isomerization unit 110 may have a higher degree of branching than a paraffin feed to the dehydrogenation-isomerization unit. It should be understood that the concentration of olefins produced via dehydrogenation-isomerization unit 110 may be limited by the thermodynamic equilibrium of olefins and paraffins at the reaction temperature. The conditions for olefin isomerization dehydrogenation-isomerization 110 may be controlled such that the number of carbon atoms in the olefins prior to and subsequent to the isomerization conditions is substantially the same.

Branched olefins produced in dehydrogenation-isomerization unit 110 may include methyl, ethyl and/or longer carbon chain branches. Hydrogen Nuclear Magnetic Resonance ($^1$H NMR) analysis of the isomerized olefin composition may be performed. Branched olefins may include quaternary and/or tertiary aliphatic carbons. In certain embodiments, an amount of quaternary aliphatic carbons produced in a unit in which olefin isomerization occurs may be minimized. As used herein, "an unit where olefin isomerization occurs and/or where branching is introduced in an olefin" refers to a dehydrogenation-isomerization unit, an isomerization unit and/or a dimerization unit. $^1$H NMR analysis of the olefins may indicate the extent of isomerization of the olefins in the hydrocarbon stream. $^1$H NMR analysis may be capable of differentiating a wide range of olefin structures such as the olefin structures illustrated in FIG. 2.

Figure 2:
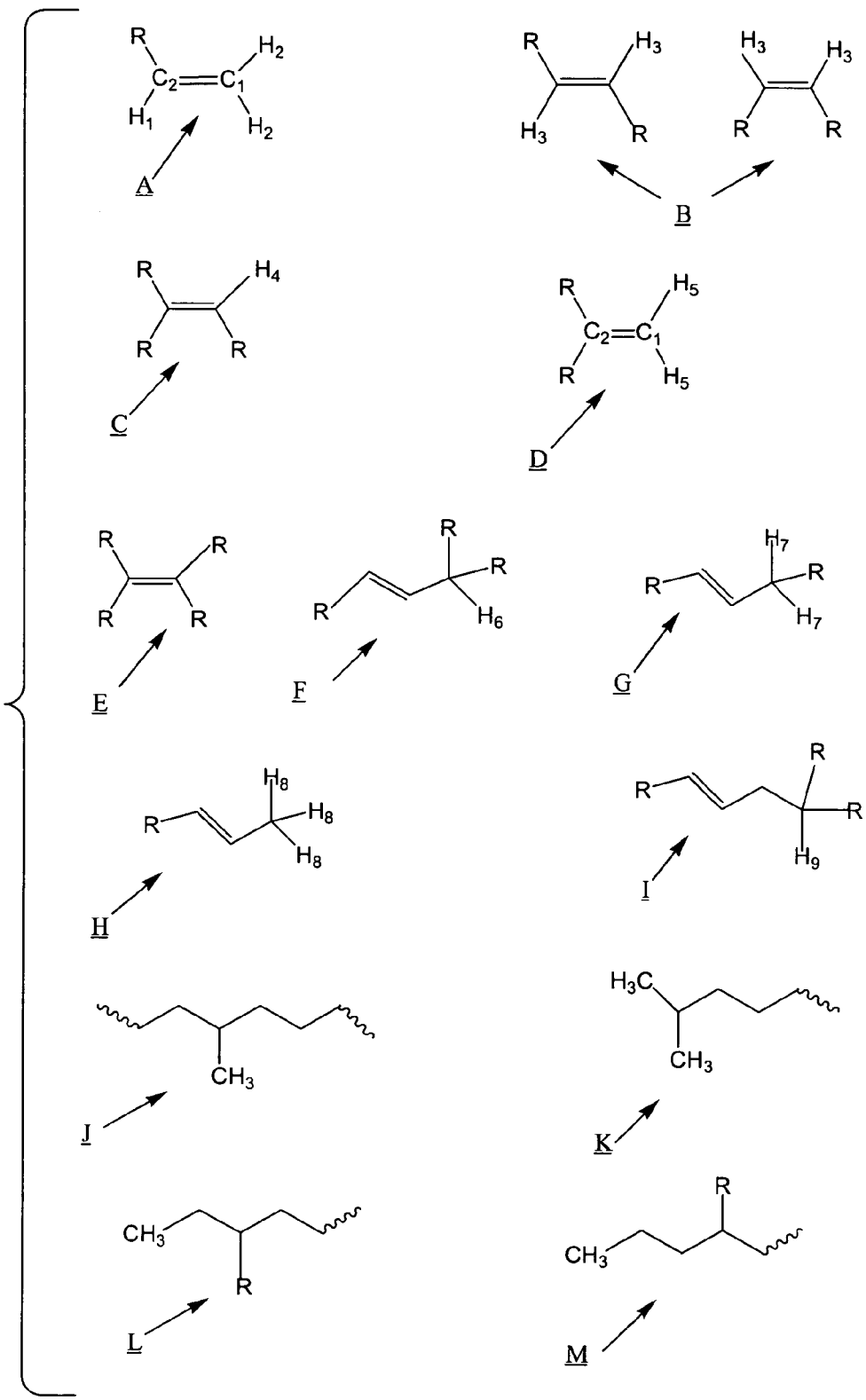
FIG. 2 illustrates structures of aliphatic and olefin sites as determined by $^1$H NMR analysis in an embodiment of a method to produce branched aliphatic alcohols.

$^1$H NMR analysis may use a combination of a 12-degree tip and a 5 second recycle delay time. For example, a spectral width of 8 KHz on a 500 MHz instrument may be used in the analysis. Enough scans (e.g., 64) may be performed to give adequate signal to noise ratio for the detection of the aliphatic and olefinic sites in the olefin molecules. Aliphatic and olefin sites may be calculated through analysis of the resulting $^1$H NMR spectrum. It is assumed in the $^1$H NMR method one double bond per molecule. The total number of branches is a sum of all aliphatic and olefinic branch sites per olefin molecule. An average carbon number per molecule may be provided as an input to a $^{13}$C NMR calculation using generally known analytical techniques (e.g., gas chromatography coupled with mass spectrometry). Aliphatic branches, as used herein, refer to branches on non-olefinic carbons. Olefinic branches, as used herein, refer to branches on olefinic carbons. The total number of branches on a double bond may be determined by summation of the individual contributions of the various assayed olefin units. Olefin units include vinyl, di-substituted, tri-substituted, vinylidene and/or tetra-substituted olefins, as illustrated in FIG. 2. The amount and type of olefin may vary with process stream composition and isomerization reaction conditions. In an embodiment, an amount of tetra-substituted olefin produced may be low.

As illustrated in FIG. 2, vinyl substituted olefin A is defined as an olefin having one functional group (R) and hydrogen $H_1$ bound to carbon $C_2$ and two hydrogens $H_2$ bound to carbon $C_1$ of the double bond. "Functional group (R)" as used herein, refers to any aliphatic group other than hydrogen that can be covalently bound to a carbon atom making up the structure of the double bond. Di-substituted olefin B, as used herein, refers to an olefin having two functional groups R and two hydrogens $H_3$ covalently bound to each of the carbon atoms of the double bond. Olefin B may be a cis-olefin, a trans-olefin or a mixture thereof. Tri-substituted olefin C, as used herein, refer to an olefin having functional groups R and hydrogen $H_4$ covalently bound to the carbon atoms of the double bond. Vinylidene olefin D, as used herein, refers to an olefin having two functional groups R covalently bound to carbon atom $C_2$ and two hydrogens $H_5$ covalently bound to carbon atom $C_1$ of the double bond. Tetra-substituted olefin E, as used herein, refers to an olefin having four functional groups R (i.e., no hydrogens) covalently bound to the carbons of the double bond. Tetra-substituted olefins are not directly detected in the $^1$H NMR spectrum since they bear no hydrogens bound to the carbon atoms of the double bond. Tetra-substituted olefins may be determined by calculating the difference between the numbers of all olefin units, as determined from the aliphatic portion of the spectrum adjacent to the double bond (e.g., hydrogens $H_6$, $H_7$, and $H_8$, in Structures F-H) and the directly identified olefins bearing hydrogens on carbons atoms of the double bond.

For example, in a solution containing olefins A, B, C, D and E, the total number of olefin branches per olefin molecule may be calculated in the following manner. The olefinic branching values may be determined by calculating the average number of branches of the individual contributions of the various assayed olefin units. In the solution, vinyl olefin A and di-substituted olefins B (e.g., cis- and trans-olefins) contribute no olefinic branches. Similarly, tri-substituted olefin C and vinylidene olefin D contribute one olefin branch each. Tetra-substituted olefin E contributes two olefin branches. Therefore, in this example, the total number of olefinic branches would be four and the average olefin branching per molecule would be about 0.67 (4 branches per six olefin molecules).

A total number of branches on aliphatic carbons in the olefin molecules (e.g., structures F and I) may be determined by summation of the individual contribution of structures with methines adjacent to the double bonds ($H_6$) and structures with methines not adjacent to the double bond ($H_9$). Olefins F and I would each contribute one branch per olefin molecule, assuming no additional aliphatic branches in the R chains. It is to be understood that, although as shown, olefins F and I are derivatives of olefin B, methine hydrogens may be found in olefins A-E depending on the branching in the R groups.

The presence of quaternary carbon atoms may be determined using carbon 13 ($^{13}$C) NMR techniques. The type of branching (e.g., methyl, ethyl, propyl or larger groups) may be determined by hydrogenation of the olefin mixture and then $^{13}$C NMR analysis of the hydrogenated olefin solution. $^{13}$C NMR analysis may resolve methyl groups that are directly attached to the hydrogenated olefin backbone structure (e.g., $CH_3$ in structure J and K), methyls in ethyl groups attached to the hydrogenated olefin backbone structure (e.g., $CH_3$ in structure L), and methyls in propyl or longer groups attached to the hydrogenated olefin backbone structure (e.g., $CH_3$ in structure M). The various methyl peak positions in FIG. 2 are given in parts per million (ppm) relative to tetramethyl silane.

Methyls in structure M in FIG. 2 may include terminal methyls, propyl and/or larger branches. The number of propyl or larger branches may not be directly obtained from the 13.5-15 ppm peak region in the spectrum. Propyl or larger branched values may be computed by taking the difference between the total number of branches per molecule and the number of methyl and ethyl branches per molecule obtained directly from the methyl spectral regions of structures J-L. The total number of branches per molecule is determined by adding the number of methyls per molecule and subtracts "two", wherein "two" accounts for the hydrogenated olefin backbone's terminal methyls.

In an embodiment, an average number of branches per olefin molecule present in the produced branched olefin composition may be greater than 0.7. In certain embodiments, an average number of branches per olefin molecule present in the branched olefin composition is from about 0.7 to about 2.5. In some embodiments, an average number of branches per olefin molecule present in the branched olefin composition is from about 0.7 to about 2.2. In certain embodiments, an average number of branches per olefin molecule present in the branched olefin composition is from about 1.0 to about 2.2. The degree of branching in the product may be controlled by controlling process conditions used in a unit in which olefin isomerization occurs. For example, high reaction temperatures and lower feed rates may result in a higher degree of branching. Methyl branches may represent between about 20 percent to about 99 percent of the total number of branches present in the olefin molecules. In some embodiments, methyl branches may represent greater than 50 percent of the total number of branches in the olefin molecules. The number of ethyl branches in the olefin molecules may represent, in certain embodiments, less than 30 percent of the total number of branches. In other embodiments, a number of ethyl branches, if present, may be between about 0.1 percent and about 2 percent of the total number of branches. Branches other than methyl or ethyl, if present, may be less than 10 percent of the total number of branches.

Aliphatic quaternary carbon atoms present in the branched olefin composition may be less than 2 percent of the carbon atoms present. In an embodiment, a number of aliphatic quaternary carbon atoms present is less than 1 percent of the carbon atoms present. For applications in which biodegradability is important, the number of aliphatic quaternary carbon atoms may be less than 0.5 percent of the carbon atoms present. In an embodiment, a number of aliphatic quaternary carbon atoms is less than 0.3 percent of the carbon atoms present. In other embodiments, a number of aliphatic quaternary carbon atoms present in the branched olefin composition is between about 0.01 percent and about 0.3 percent of the aliphatic carbon atoms present.

A second hydrocarbon stream may exit dehydrogenation-isomerization unit 110 and be transferred to other processing units (e.g., a hydroformylation unit, separation units, an alkylation units) via second conduit 114. At least a portion of the second hydrocarbon stream may exit dehydrogenation-isomerization unit 110 and be introduced into hydroformylation unit 116 via second conduit 114. In hydroformylation unit 116, at least a portion of the olefins in the second hydrocarbon stream may be converted to alcohols. At least a portion of the produced alcohols and at least a portion of the unreacted components of the second hydrocarbon stream may form a hydroformylation reaction stream.

In an embodiment, olefins may be separated, if desired, from the second hydrocarbon stream through techniques generally known in the art (e.g., distillation, molecular sieves, extraction, adsorption, adsorption/desorption, and/or membranes). Separation of at least a portion of the branched olefins from the linear olefins and paraffins may increase the concentration of branched olefins entering the hydroformylation unit. In addition, separation of at least a portion of the branched olefins from the linear olefins and paraffins may influence the ratio of linear to branched olefins produced in the hydroformylation unit.

Figure 3:
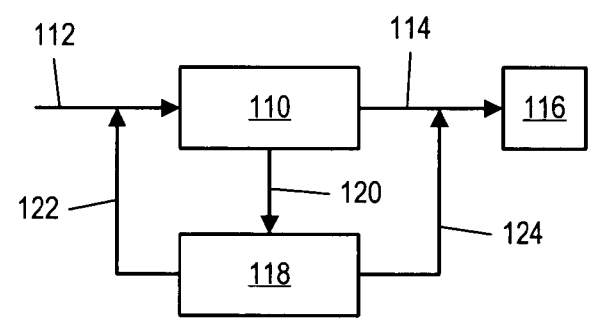
FIG. 3 depicts a schematic diagram of an embodiment of a system for producing branched aliphatic alcohols using a dehydrogenation-isomerization unit and a separation unit to separate branched olefins from linear olefins and paraffins.

Referring to FIG. 3, a second hydrocarbon stream may exit dehydrogenation-isomerization unit 110 and enter separation unit 118 via separation conduit 120. Separation unit 118 may produce at least two streams, a branched olefins stream and a linear olefins and paraffins stream. In separation unit 118, the second hydrocarbon stream may be contacted with organic and/or inorganic molecular sieves (e.g., zeolite or urea) with the correct pore size for branched olefins and/or linear olefins and paraffins. Subsequent desorption (e.g., solvent desorption) of at least a portion of the branched olefins and/or at least a portion of the linear olefins and paraffins from the molecular sieves may produce at least two streams (e.g., a branched olefins stream and a linear olefins and paraffins stream).

Separation unit 118 may include a fixed bed containing adsorbent for separation of the second hydrocarbon stream to produce a branched olefin and paraffins stream and a linear olefins and paraffins stream. Separation temperatures in separation unit 118 may range from about 100° C. to about 400° C. In some embodiments, separation temperatures may range from 180° C. to about 380° C. Separation in separation unit 118 may be conducted at a pressure ranging from about 2 atmospheres (202 kPa) to about 7 atmospheres (710 kPa). In some embodiments, a pretreatment of a second hydrocarbon stream may be performed to prevent adsorbent poisoning. An example of an adsorption/desorption process is a Molex process using Sorbex® separations technology (UOP process, UOP, Des Plaines, Ill.). Adsorption/desorption processes are described in U.S. Pat. No. 6,225,518 to Sohn et al., entitled "Olefinic Hydrocarbon Separation Process;" U.S. Pat. No. 5,292,990 to Kantner et al., entitled, "Zeolite Compositions For Use in Olefinic Separations" and U.S. Pat. No. 5,276,246 to McCulloch et al., entitled "Process For Separating Normal Olefins From Non-Normal Olefins," all of which are incorporated by reference as if fully set forth herein.

At least a portion of the linear olefins and paraffins stream may be transported to other processing units and/or stored on site. In an embodiment, at least a portion of the linear olefins and paraffins stream may be combined with first hydrocarbon stream in first conduit 112 via linear olefin and paraffin recycle conduit 122. The combined stream may enter dehydrogenation-isomerization unit 110 via first conduit 112 to continue the process to produce aliphatic alcohols. In some embodiments, a linear olefins and paraffins stream may be introduced directly into dehydrogenation-isomerization unit 110.

At least a portion of the branched olefins stream may be transported and utilized in other processing streams and/or stored on site via branched olefins conduit 124. In some embodiments, at least a portion of a branched olefins stream may exit separation unit 118 and be introduced into second conduit 114 via branched olefins conduit 124. In other embodiments, at least a portion of a branched olefins stream may exit separation unit 118 and be introduced directly into a hydroformylation unit.

Referring to FIG. 1, the second hydrocarbon stream may exit dehydrogenation-isomerization unit and enter hydroformylation unit 116 via second conduit 114. Hydroformylation unit 116 may have several points of entry to accommodate entry of additional process streams. As used herein, "stream entering into the hydroformylation unit" is defined as the entry of process streams into the hydroformylation unit through one or more entry points. Examples of such process streams include, but are not limited to, additional streams from dehydrogenation-isomerization unit 110, a diluent hydrocarbon stream, gases and/or other hydrocarbon streams that include olefins and paraffins derived from other processes.

In a hydroformylation process, olefins are converted to aldehydes, alcohols or a combination thereof by reaction of at least a portion of the olefins with carbon monoxide and hydrogen according to an Oxo process. As used herein, an "Oxo process" refers to the reaction of an olefin with carbon monoxide and hydrogen in the presence of a metal catalyst (e.g., a cobalt catalyst) to produce an alcohol containing one more carbon atom than the starting olefin. In other hydroformylation processes, a "modified Oxo process" is used. As used herein, a "modified Oxo process" refers to an Oxo process that uses a phosphine, phosphite, arsine or pyridine ligand modified cobalt or rhodium catalyst. Preparation and use of modified Oxo catalysts are described in U.S. Pat. No. 3,231,621, to Slaugh, entitled "Reaction Rates In Catalytic Hydroformylation"; U.S. Pat. No. 3,239,566 to Slaugh et al., entitled "Hydroformylation Of Olefins;" U.S. Pat. No. 3,239,569 to Slaugh et al., entitled "Hydroformylation Of Olefins;" U.S. Pat. No. 3,239,570 to Slaugh et al., entitled "Hydroformylation Of Olefins;" U.S. Pat. No. 3,239,571 to Slaugh et al., entitled "Hydroformylation Of Olefins;" U.S. Pat. No. 3,400,163 to Mason et al., entitled "Bicyclic Heterocyclic Sec- And Tert-Phosphines;" U.S. Pat. No. 3,420,898 to Van Winkle et al., entitled "Single Stage Hydroformylation Of Olefins To Alcohols Single Stage Hydroformylation Of Olefins To Alcohols;" U.S. Pat. No. 3,440,291 to Van Winkle et al., entitled "Single Stage Hydroformylation Of Olefins To Alcohols;" U.S. Pat. No. 3,448,157 to Slaugh et al., entitled "Hydroformylation Of Olefins;" U.S. Pat. No. 3,488,158 to Slaugh et al., entitled "Hydroformylation Of Olefins;" U.S. Pat. No. 3,496,203 to Morris et al., entitled "Tertiary Organophosphine-Cobalt-Carbonyl Complexes;" U.S. Pat. No. 3,496,204 to Morris et al., entitled "Tertiary Organophosphine-Cobalt-Carbonyl Complexes;" U.S. Pat. No. 3,501,515 to Van Winkle et al., entitled "Bicyclic Heterocyclic Terteriary Phosphine-Cobalt-Carbonyl Complexes"; U.S. Pat. No. 3,527,818 to Mason et al., entitled "Oxo Alcohols Using Catalysts Comprising Ditertiary Phosphines;" U.S. patent application Ser. No. 10/075,682, entitled "A Process For Preparing A Branched Olefin, A Method Of Using The Branched Olefin For Making A Surfactant, and a Surfactant" and in U.S. patent application Ser. No. 10/167,209 entitled "Process for the Preparation Of A Highly Linear Alcohol Composition," all of which are incorporated herein by reference. Methods of alcohol production are also described by Othmer, in "Encyclopedia of Chemical Technology" 2000, Fourth Edition; and by Wickson, in "Monohydric Alcohols; Manufacture, Applications and Chemistry" Ed. Am. Chem. Soc. 1981, both of which are incorporated herein by reference.

A hydroformylation catalyst used in hydroformylation unit 116 may include a metal from Group VIII of the Periodic Table. Examples of Groups VIII metals include cobalt, rhodium, nickel, palladium or platinum. The Group VIII metal may be used as a complex compound. A complex compound may be a Group VIII metal combined with a ligand. Examples of ligands include, but are not limited to, a phosphine, phosphite, arsine, stibine or pyridine ligand. Examples of hydroformylation catalysts include, but are not limited to, cobalt hydrocarbonyl catalyst, cobalt-phosphine ligand catalyst, rhodium-phosphine ligand catalyst or combinations thereof.

A source of the Group VIII metal may be a salt. Salts of acids with a pKa value from about 2 to about 6 when measured in water at 20° C., may be used. Examples of suitable acids include nitric acid, sulfuric acid, organic acids and sulfonic acids. Examples of organic acids include octanoic acid, dichloroacetic acid, trifluoroacetic acid perfluoropropionic acid and combinations thereof. Examples of sulfonic acids include p-toluenesulfonic acid, benzenesulfonic acid, methanesulfonic acid and combinations thereof.

Ligands of a hydroformylation catalyst may be made of monophosphines. A monophosphine may include three hydrocarbon groups, three oxy groups, or combinations of hydrocarbon groups and oxy groups. Monophosphine ligands may be attached to arsenic or tin to form a hydroformylation catalyst. Examples of monophosphine ligands include, but are not limited to, triamylphosphine, trihexylphosphine, dimethylethylphosphine, diamylethylphosphine, tricyclopentylphosphine, tricyclohexylphosphine, diphenylbutylphosphine, diphenylbenzylphosphine, diphenyl(2-pyridyl)phosphine, phenyl[bis(2-pyridyl)]phosphine, triethoxyphosphine, butyldiethoxyphosphine, triphenylphosphine, dimethylphenylphosphine, methyldiphenylphosphine, dimethylpropylphosphine, tritoluylphosphine or combinations thereof.

In other embodiments, bidentate phosphine ligands may be used. Bidentate phosphine ligands may be attached to arsenic or antimony to form a hydroformylation catalyst. Examples of bidentate phosphine ligands include, but are not limited to, 1,2-bis(dimethylphosphino)ethane, 1,2- and 1,3-bis(dimethylphosphino)propane, 1,2-bis(diethylphosphino)ethane, 1,2-bis[di(1-butyl)phosphino]ethane, 1-dimethylphosphino-2-diethylphosphinoethane, 1,2-bis(di-phenylphosphino)ethane, 1,2-bis(diperfluorophenylphosphino)ethane, 1,3-bis(diphenylphosphino)propane, 1,4-bis(diphenylphosphino)butane, 1-dimethylphosphino-2-diphenylphosphinoethane, 1-diethylphosphino-3-diphenylphosphinopropane, 1,2-bis[di(o-toluyl)phosphino] ethane or combinations thereof.

In some embodiments, phosphine ligands may include phosphabicyclo-hydrocarbons. Examples of phosphabicyclo-hydrocarbons include, but are not limited, 9-hydrocarbyl-9-phospha-bicyclononane and P, P-bis(9-phosphabicyclononyl)-hydrocarbons in which the smallest P-containing ring contains at least 5 carbon atoms. Examples of ligands in which the P-containing ring contains at least 5 carbon atoms include, but are not limited to, 9-aryl-9-phosphabicyclo[4.2.1]nonanes; 9-(dialkylaryl)-9-phosphabicyclo [4.2.1]nonanes; 9-alkyl-9-phospha-bicyclo[4.2.1]nonanes; 9-cycloalkyl-9-phospha-bicyclo[4.2.1]nonanes; 9-cycloalkenyl-9-phosphabicyclo[4.2.1]nonanes; P, P-bis(9-phosphabicyclo-nonyl)alkanes; 9-aryl-9-phosphabicyclo[3.3.1] nonanes; 9-(dialkylaryl)-9-phosphabicyclo[3.3.1]nonanes; 9-alkyl-9-phospha-bicyclo[3.3.1]nonanes; 9-cycloalkyl-9-phospha-bicyclo[3.3.1]nonanes; 9-cycloalkenyl-9-phosphabicyclo[3.3.1]nonanes. Other examples of such ligands, include but are not limited to, 9-phenyl-9-phosphabicyclo [4.2.1]nonane; 9-(2,4-dimethylphenyl)-9-phosphabicyclo [4.2.1]nonane; 9-ethyl-9-phosphabicyclo [4.2.1]nonane; 9-cyclohexyl-9-phosphabicyclo[4.2.1]nonane; 9-cyclopentenyl-9-phospha-bicyclo[4.2.l]nonane; 1,2-P, P-bis(9-phosphabicyclo-[4.2.1]nonyl)ethane; 1,3-P, P-bis(9-phosphabicyclo-[4.2.1]nonyl)propane; 1,4-P, P-bis(9-phosphabicyclo-[4.2.1]nonyl)butane; 9-aryl-9-phosphabicyclo[4.2.1] nonanes; 9-(dialkylaryl)-9-phosphabicyclo[4.2.1]nonanes; 9-alkyl-9-phospha-bicyclo[4.2.1]nonanes; 9-cycloalkyl-9-phospha-bicyclo[4.2.1]nonanes; 9-cycloalkenyl-9-phosphabicyclo[4.2.1]nonanes; P, P-bis(9-phosphabicyclo-nonyl)alkanes; 9-phenyl-9-phosphabicyclo[3.3.1]nonane; 9-(2,4-dimethylphenyl)-9-phosphabicyclo[3.3.1]nonane; 9-ethyl-9-phosphabicyclo [3.3.1]nonane; 9-cyclohexyl-9-phosphabicyclo[3.3.1]nonane; 9-cyclopentenyl-9-phosphabicyclo[3.3.1]nonane; 1,2-P, P-bis(9-phosphabicyclo-[3.3.1]nonyl)ethane; 1,3-P, P-bis(9-phosphabicyclo-[3.3.1]nonyl)propane; 1,4-P,P-bis(9-phosphabicyclo-[3.3.1]nonyl)butane or combinations thereof.

A phosphine ligand may be used in amounts in a molar ratio of phosphine to metal (e.g., cobalt) in a range from about 0.5 to about 2. In certain embodiments, a molar ratio of alkyl phosphine to metal may be in a range of about 0.6 to about 1.8. In addition to the metal and the phosphine ligand, the hydroformylation catalyst may also include additional components for enhancing the stability of the metal/phosphine system. In some embodiments, a hydroformylation catalyst may include additional components for improving the alcohol selectivity. Examples of additional components are potassium hydroxide and sodium hydroxide. The additional component may be used in a molar ratio of additional component to metal from about 0 to about 1.

A source of carbon and hydrogen for a hydroformylation process in hydroformylation unit 116 may be a gas. Examples of gases include, but are not limited to, carbon monoxide, hydrogen or synthesis gas. A ratio of carbon monoxide to hydrogen applied in hydroformylation unit 116 may be in a range from about 1.0 to about 5.0. In certain embodiments, a hydrogen to carbon monoxide molar ratio may be in a range from about 1.5 to about 2.5.

Synthesis gas that contains hydrogen and carbon monoxide in a molar ratio from about 1 to about 2.5 may be used in hydroformylation unit 116. In other embodiments, synthesis gas that contains hydrogen and carbon monoxide in a molar ratio from 1.0 to 10.0 may be used. In other embodiments, synthesis gas that contains a hydrogen and carbon monoxide molar ratio from 1.5 to 2.5 may be used as a source of carbon and hydrogen. It should be understood that the gas feed may be a mixture of carbon monoxide and hydrogen gases only, synthesis gas only or combinations thereof.

In hydroformylation unit 116, olefins in the second hydrocarbon stream may be hydroformylated using a continuous, semi-continuous or batch process. In case of a continuous mode of operation, the liquid hourly space velocities may be in the range of about $0.1\ h^{-1}$ to about $10\ h^{-1}$. When operating hydroformylation unit 116 as a batch process, reaction times may vary from about 0.1 hours to about 10 hours or even longer.

Reaction temperatures in hydroformylation unit 116 may range from about 100° C. to about 300° C. In certain embodiments, reaction temperatures in the hydroformylation unit ranging from about 125° C. to about 250° C. may be used. Pressure in hydroformylation unit 116 may range from about 1 atmosphere (101 kPa) to about 300 atmospheres (30398 kPa). In an embodiment, a pressure from about 20 (2027 kPa) to about 150 atmospheres (15199 kPa) may be used. An amount of catalyst relative to the amount of olefin to be hydroformylated may vary. Typical molar ratios of catalyst to olefin in the second hydrocarbon stream may range from about 1:1000 to about 10:1. A ratio of between about 1:10 and about 5:1 may be used in certain embodiments. In an embodiment, a second stream may be added to hydroformylation unit 116 to control reaction conditions. The second stream may include solvents that do not interfere substantially with the desired reaction. Examples of such solvents include, but are not limited to, alcohols, ethers, acetonitrile, sulfolane and paraffins.

Mono-alcohol selectivities of at least 90 percent and even of at least 92 percent may be achieved in hydroformylation unit 116. In addition, olefin conversions to aliphatic alcohols may range from about 50 percent by weight to greater than 95 percent by weight. In certain embodiments, olefin conversion to aliphatic alcohols may be greater than 75 percent by weight. In some embodiments, olefin conversion to aliphatic alcohols may be greater than 99 percent by weight.

Isolation of aliphatic alcohols produced from the hydroformylation reaction product stream may be achieved by generally known methods. In an embodiment, isolation of the aliphatic alcohols includes subjecting the produced aliphatic alcohols to a first distillation, a saponification, a water washing treatment and a second distillation.

The hydroformylation reaction mixture stream may enter separator 126 via third conduit 128. In separator 126, the hydroformylation reaction product stream may be subjected to a first distillation step (e.g., flash distillation or a short path distillation). In an embodiment, a short path distillation may be used to produce at least two streams, a bottom stream and a top stream. At least a portion of the bottom stream may be recycled to hydroformylation unit 116 via bottom stream recycle conduit 130, in certain embodiments. The top stream may include, but is not limited to, paraffins, unreacted olefins and a crude aliphatic alcohol product.

In an embodiment, a top stream may be subjected to a saponification treatment to remove any acids and esters present in the stream. Saponification may be performed by contacting the top stream with an aqueous solution of a hydroxide base (e.g., sodium hydroxide or potassium hydroxide) at elevated temperatures with agitation. The saponification may be carried out by contacting the top stream with an aqueous 0.5 percent to 10 percent hydroxide base solution at a crude alcohol/water ratio of 10:1 to 1:1. The amount of hydroxide base used may depend on an estimated amount of esters and acids present.

Saponification of the top stream may be carried out batch-wise or continuously. The top stream may be subjected to one or more saponification processes. Saponification reaction temperatures may be from about 40° C. to about 99° C. In an embodiment, saponification temperatures may range from about 60° C. to about 95° C. Mixing of the top stream with the basic water layer may be performed during the saponification reaction. Separation of the top stream from the basic water layer may be performed using known methods. The top stream may be subjected to a water wash after separation to remove any sodium salts present. The top stream may be separated using generally known techniques (e.g., fractional distillation) to produce at least two streams, a crude alcohol product stream and a paraffins and unreacted olefins stream. As used herein, "fractional distillation" refers to the distillation of liquids and subsequent collection of fractions of liquids determined by boiling point. The paraffins and unreacted olefins stream may be recycled, transported to other units for processing, stored on site, transported offsite and/or sold.

In certain embodiments, a crude aliphatic alcohol product stream may contain unwanted by-products (e.g., aldehydes, hemi-acetals). The by-products may be removed by subjecting the crude alcohol product stream to a hydrofinishing treatment step to produce an aliphatic alcohol product stream. "Hydrofinishing," as used herein, refers to a hydrogenation reaction carried out under relatively mild conditions. Hydrofinishing may be carried out using conventional hydrogenation processes. Conventional hydrogenation processes may include passing the crude alcohol feed together with a flow of hydrogen over a bed of a suitable hydrogenation catalyst. The aliphatic alcohol product stream may include greater than 50 percent by weight of the produced aliphatic alcohols. In some embodiments, the aliphatic alcohol product stream may include greater than 80 percent by weight of the produced aliphatic alcohols. In other embodiments, the aliphatic alcohol product stream may include greater than 95 percent by weight of the produced aliphatic alcohols. The aliphatic alcohol product stream may include branched aliphatic primary alcohols. The resulting aliphatic alcohols in the aliphatic alcohol product stream may be sold commercially, transported off-site, stored on site and/or used in other processing units via product conduit 132.

The composition of an aliphatic alcohol product stream may include hydrocarbons with an average carbon number ranging from 8 to 19. In an embodiment, an average carbon number of the hydrocarbons in aliphatic alcohol product stream may range from 10 to 17. In certain embodiments, an average carbon number of the feed stream may range from 10 to 13. In other embodiments, an average carbon number of the feed stream may range from 14 to 17. The aliphatic alcohol product stream may include branched primary alcohols. The branched primary alcohol product may be suitable for the manufacture of anionic, nonionic and cationic surfactants. In some embodiments, branched primary alcohol products may be used as the precursor for the manufacture of anionic sulfates, including aliphatic sulfates and oxyalkyl sulfates and oxyalkyl alcohols.

Aliphatic alcohols may have slightly higher aliphatic branching and slightly higher number of quaternary carbons as the olefin precursor. In some embodiments, aliphatic branching may include methyl and/or ethyl branches. In other embodiments, aliphatic branching may include methyl, ethyl and higher aliphatic branching. In certain embodiments, a number of quaternary carbon atoms in the aliphatic alcohol product may be less than 0.5. In other embodiments, a number of quaternary carbon atoms in the aliphatic alcohol product may be less than 0.3. Branching of the alcohol product may be determined by $^1$H NMR analysis. The number of quaternary carbon atoms may be determined by $^{13}$C NMR. A $^{13}$C NMR method for determining quaternary carbon atoms for branched aliphatic alcohols is described in U.S. Pat. No. 6,150,322 to Singleton et al., entitled, "Highly Branched Primary Alcohol Compositions and Biodegradable Detergents Made Therefrom," which is incorporated by reference herein.

In certain embodiments, at least a portion of the paraffins and unreacted olefins stream may be combined with the first hydrocarbon stream in first conduit 112 to produce a combined stream via fourth conduit 134. The combined stream may be introduced into dehydrogenation-isomerization unit 110 via first conduit 112. At least a portion of the olefins in the combined stream may be isomerized to branched olefins. In some embodiments, at least a portion of the paraffins and unreacted olefins stream is introduced directly into dehydrogenation-isomerization unit 110 via one or more entry points. Because the paraffins and unreacted olefins stream containing paraffins and unreacted olefins may be recycled to dehydrogenation-isomerization unit 110 as one stream, the process may be more efficient, resulting in an overall higher throughput. The higher throughput will increase the overall yield of the aliphatic alcohols.

Figure 4:
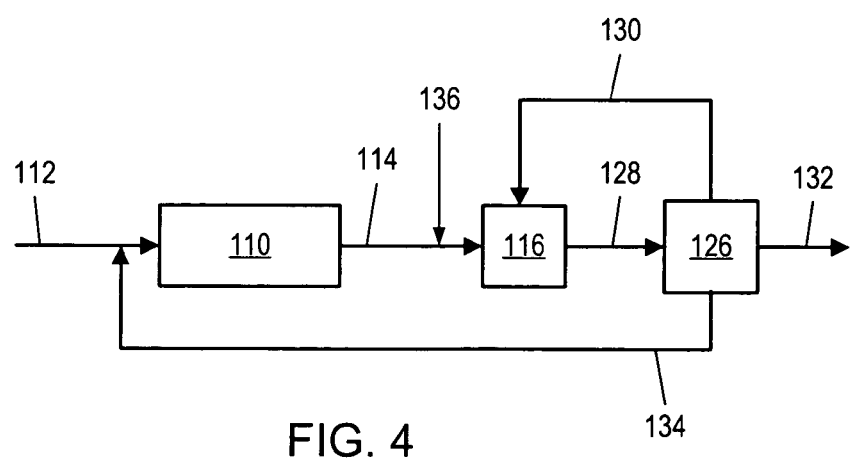
FIG. 4 depicts a schematic diagram of an embodiment of a system for producing branched aliphatic alcohols using a dehydrogenation-isomerization unit with addition of an additional hydrocarbon stream.

In some embodiments, an olefins and paraffins concentration in hydroformylation unit 116 may be adjusted depending on the source of the olefin stream entering the hydroformylation unit. A third hydrocarbon stream may be added upstream of hydroformylation unit 116 to produce a combined stream. In other embodiments, a third hydrocarbon stream may be introduced directly into hydroformylation unit 116 through one or more points. A third hydrocarbon stream may be introduced into second conduit 114 via fifth conduit 136 to produce a combined stream as depicted in FIG. 4. The combined stream may enter hydroformylation unit 116 via second conduit 114 to continue the process to produce aliphatic alcohols.

The third hydrocarbon stream may be from the same source as the first hydrocarbon stream. In some embodiments, a third hydrocarbon stream may be a hydrocarbon stream that includes olefins, paraffins, and/or hydrocarbon solvents derived from another source. The third hydrocarbon stream may include olefins and paraffins. In certain embodiments, an average carbon number of the hydrocarbons in the third hydrocarbon stream ranges from 7 to 18. In some embodiments, a paraffin content of the third hydrocarbon stream may be between about 60 percent and about 90 percent by weight. In other embodiments, a paraffin content of the third hydrocarbon stream may be greater than 90 percent by weight.

In an embodiment, an olefin content of a third hydrocarbon stream ranges between about 1 percent and about 99 percent relative to the total hydrocarbon content. In certain embodiments, an olefin content of the third hydrocarbon stream may be between about 45 percent and about 99 percent by weight. In other embodiments, an olefin concentration of the third hydrocarbon stream may be greater than 80 percent by weight.

In certain embodiments, dehydrogenation-isomerization unit 110 may be separated into a plurality of zones to control reaction temperatures and/or prevent unwanted side reactions (e.g., diene formation and/or cyclization reactions). A first hydrocarbon stream containing paraffins and unreacted olefins may be introduced into dehydrogenation-isomerization unit 110 via first conduit 112 as depicted for System 200 in FIG. 5. In some embodiments, a first hydrocarbon stream includes alpha-olefins. Hydrocarbons in the first hydrocarbon stream may have an average carbon number from 7 to 18. In other embodiments, hydrocarbons in the first hydrocarbon stream may have an average carbon number from 10 to 17. In some embodiments, hydrocarbons in the first hydrocarbon stream may have an average carbon number from 14 to 17. In certain embodiments, hydrocarbons in the first hydrocarbon stream may have an average carbon number from 10 to 13. An alpha-olefin content of the first hydrocarbon stream may be greater than 70 percent of the total amount of olefins in the first hydrocarbon stream. In certain embodiments, a first hydrocarbon stream is produced from a Fischer-Tropsch process. Dehydrogenation-isomerization unit 110 may be divided into a plurality of zones. The plurality of zones may include, but is not limited to, a first reaction zone, a transition zone and a second reaction zone. In first reaction zone 210, at least a portion of the paraffins in the first hydrocarbon stream may be dehydrogenated to olefins to produce an olefinic stream. The process stream may then pass into second reaction zone 212. In second reaction zone 212, at least a portion of the olefins in the process stream may be isomerized to branched olefins to produce a second hydrocarbon stream.

In first reaction zone 210, the dehydrogenation catalyst may be selected from a wide range of catalyst types. For example, the catalyst may be based on a metal or metal compound deposited on a porous support. The metal or metal compound may be selected from, but is not limited to, chrome oxide, iron oxide and noble metals.

Techniques of preparing catalysts, for performing the dehydrogenation step and for performing associated separation steps are known in the art. For example, suitable procedures for preparing catalysts and performing the dehydrogenation step are described in U.S. Pat. No. 5,012,021 to Vora et al., entitled "Process For the Production of Alkyl Aromatic Hydrocarbons Using Solid Catalysts;" U.S. Pat. No. 3,274,287 to Moore et al., entitled "Hydrocarbon Conversion Process and Catalyst;" U.S. Pat. No. 3,315,007 to Abell et al., entitled "Dehydrogenation of Saturated Hydrocarbons Over Noble-Metal Catalyst;" U.S. Pat. No. 3,315,008 to Abell et al., entitled "Dehydrogenation of Saturated Hydrocarbons Over Noble-Metal Catalyst;" U.S. Pat. No. 3,745,112 to Rausch, entitled "Platinum-Tin Uniformly Dispersed Hydrocarbon Conversion Catalyst and Process;" U.S. Pat. No. 4,506,032 to Imai et al., entitled "Dehydrogenation Catalyst Composition" and U.S. Pat. No. 4,430,517 to Imai et al., entitled "Dehydrogenation Process Using a Catalytic Composition," all of which are incorporated by reference herein.

Reaction temperatures in first reaction zone 210 may range from about 300° C. to about 600° C. In some embodiments, a reaction temperature in first reaction zone 210 may range from about 450° C. to about 550° C. A total pressure in first reaction zone 210 may range from about 0.010 atmosphere (1 kPa) to about 25.0 atmospheres (2534 kPa). In certain embodiments, total pressure in first reaction zone 210 may range from about 0.010 atmospheres (1 kPa) to about 15.0 atmospheres (1520 kPa). In some embodiments, hydrogen may be fed together with the unreacted first hydrocarbon stream in order to prevent coking. Hydrogen and paraffins present in the unreacted first hydrocarbon stream may be fed at a hydrogen to paraffin molar ratio in a range from about 0.1 to about 20. In an embodiment, a hydrogen to paraffin molar ratio may be in a range of about 1 to about 10.

Figure 5A:
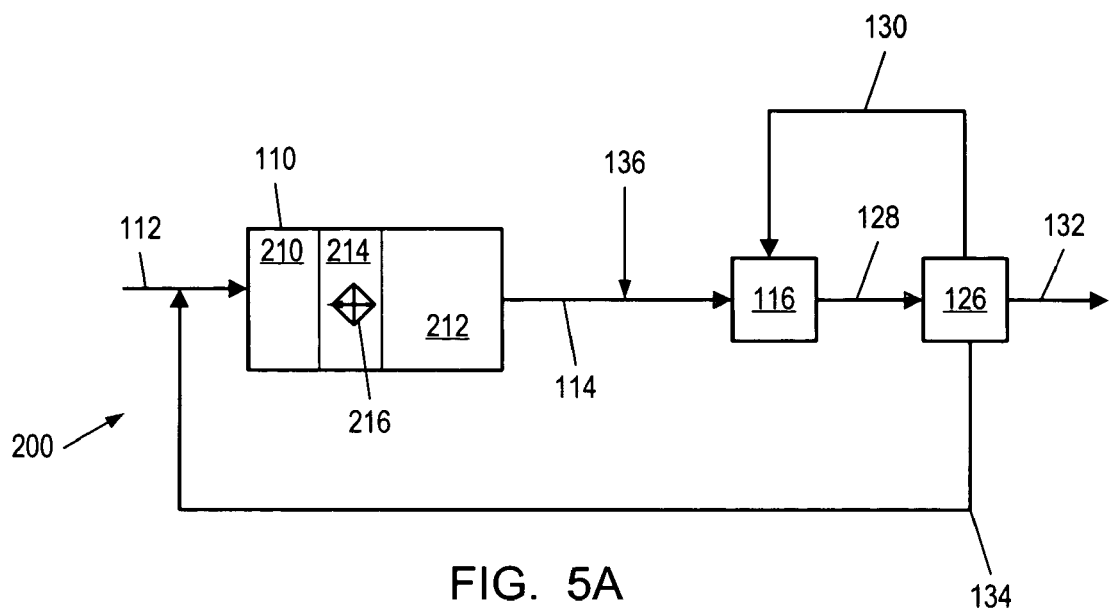
FIGS. 5A-B depict schematic diagrams of embodiments of a system for producing branched aliphatic alcohols using a two-zone dehydrogenation-isomerization unit.
Figure 5B:
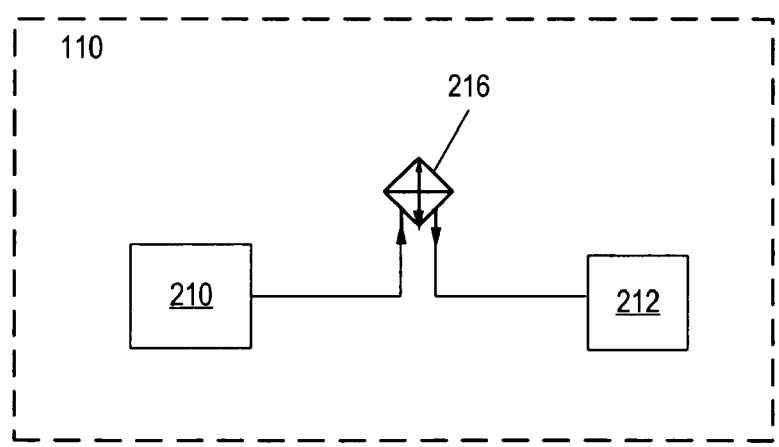

Residence time in first reaction zone 210 may be selected such that a conversion level of the paraffins to olefins is below about 50 mole percent. In certain embodiments, a conversion level of the paraffins to olefins may be kept in a range from about 10 mole percent to about 20 mole percent. By keeping the conversion level low, side reactions (e.g., diene formation and cyclization reactions) may be prevented. In some embodiments, an olefinic hydrocarbon stream may exit first reaction zone 210, pass through transition zone 214 and enter second reaction zone 212. Transition zone 214 may include heat exchanger 216. Heat exchanger 216 may reduce the temperature of the olefinic hydrocarbon stream. In an embodiment, first reaction zone 210 and second reaction zone 212 in dehydrogenation-isomerization unit 110 may be separate units, as depicted in FIG. 5B, with heat exchanger 216 positioned between the two units.

After the olefinic hydrocarbon stream enters second reaction zone 212, at least a portion of the olefins are isomerized to branched olefins to produce a second hydrocarbon stream. The composition and level of branching of the second hydrocarbon stream may be performed by $^1$H NMR analysis. In an embodiment, an olefinic stream may exit first reaction zone 210 and directly enter second reaction zone 212 where at least a portion of the olefins in the olefinic stream are isomerized to branched olefins.

The catalyst used for isomerization of the olefins to branched olefins may be the same as described in U.S. Pat. No. 5,648,584 to Murray, entitled "Process for Isomerizing Linear Olefins to Isoolefins" and U.S. Pat. No. 5,648,585 to Murray et al., entitled "Process for Isomerizing Linear Olefins to Isoolefins" both of which are incorporated herein by reference.

In an embodiment, linear olefins in a first hydrocarbon stream are isomerized in second reaction zone 212 by contacting at least a portion of the olefinic stream with a zeolite catalyst. The zeolite catalyst may have at least one channel with a crystallographic free channel diameter ranging from greater than 4.2 Å to less than 7 Å. The zeolite catalyst may have an elliptical pore size large enough to permit entry of a linear olefin and at least partial diffusion of a branched olefin. The pore size of the zeolite catalyst may also be small enough to retard coke formation.

Temperatures in second reaction zone 212 may be from about 200° C. to about 500° C. to isomerize linear olefins to branched olefins. In some embodiments, reaction temperatures in the first reaction zone and the second reaction zone are substantially the same. In such embodiments, use of a heat exchanger is not required. Typically, however, the reaction temperature of second reaction zone 212 is less than the reaction temperature of the first reaction zone. The use of a heat exchanger lowers the temperature of the stream leaving the first reaction zone to the appropriate temperature for reaction in the second reaction zone. Hydrocarbon partial pressure in the second reaction zone may be from about 0.1 atmosphere (10 kPa) to about 10 atmospheres (1013 kPa).

In some embodiments, the second hydrocarbon stream may exit a second reaction zone and enter a separation unit. In the separation unit, branched olefins may be separated from linear olefins and paraffins as previously described with regard to FIG. 3. Referring to FIG. 5, the second hydrocarbon stream may exit second reaction zone 212 via second conduit 114 and enter hydroformylation unit 116. At least a portion of the olefins in the second hydrocarbon stream may be hydroformylated to produce a hydroformylation reaction stream as described for System 100. At least a portion of the hydroformylation reaction stream may be separated into a bottom stream and a top stream using generally known methods. The crude aliphatic alcohol product stream may be further purified as described for System 100 to produce a paraffins and unreacted olefins stream and an aliphatic alcohol product stream. The aliphatic alcohol product stream may include branched aliphatic alcohols (e.g., branched primary aliphatic alcohols). The aliphatic alcohol product stream may be recycled, transported to other processing units, sold, and/or transported to storage vessels.

The hydroformylation reaction mixture stream may enter separator 126 via third conduit 128. In separator 126, at least three streams, a bottom stream, a paraffins and unreacted olefins stream and an aliphatic alcohol product stream, may be produced using techniques previously described for System 100. At least a portion of the bottom stream may be recycled to the hydroformylation unit via bottom stream recycle conduit 130. At least a portion of the paraffins and unreacted olefins stream may be recycled combined with other process streams, transported to and/or stored on site. The aliphatic alcohol product stream may be transported via product conduit 132 to be stored on site, sold commercially, transported off-site and/or utilized in other processing units.

In an embodiment, at least a portion of the paraffins and unreacted olefins stream may be combined with the first hydrocarbon stream to produce a combined hydrocarbon stream via fourth conduit 134. The combined hydrocarbon stream may enter first reaction zone 210 and undergo the dehydrogenation-isomerization process and hydroformylation process to produce aliphatic alcohols. By recycling the paraffins and unreacted olefins stream, the yield of product may be maximized. In an embodiment, a paraffins and unreacted olefins stream may directly enter dehydrogenation-isomerization unit 110 through one or more points of entry.

In some embodiments, an olefins and paraffins concentration in hydroformylation unit 116 may be adjusted depending on the source of the olefin stream entering the hydroformylation unit as previously described for System 100. At least a portion of a third hydrocarbon stream may be introduced into second conduit 114 upstream of hydroformylation unit 116 via fifth conduit 136. The combined stream may be introduced into hydroformylation unit 116 via second conduit 114. At least a portion of the olefins in the combined stream may be hydroformylated to produce aliphatic alcohols. In an embodiment, a third hydrocarbon stream may be introduced directly into hydroformylation unit 116 through one or more points of entry.

A third hydrocarbon stream may be used to optimize the olefin concentration in hydroformylation unit 116 at a concentration sufficient to maximize hydroformylation of the olefin. In addition, the third hydrocarbon may optimize the ratio of linear to branched aliphatic groups in the aliphatic alcohol. The third hydrocarbon stream may be, but is not limited to, a hydrocarbon stream containing olefins, paraffins and/or hydrocarbon solvents.

In an embodiment, a third hydrocarbon stream includes a paraffin content of between about 50 percent and about 99 percent relative to the total hydrocarbon content. In certain embodiments, a paraffin content of the third hydrocarbon stream ranges between 60 percent and 90 percent relative to the total hydrocarbon content. In other embodiments, a paraffin content of the third hydrocarbon stream is greater than 80 percent relative to the total hydrocarbon content.

In an embodiment, an olefin content of a third hydrocarbon stream ranges between about 1 percent and about 99 percent relative to the total hydrocarbon content. In other embodiments, an olefin content of a third hydrocarbon stream may be greater than 80 percent relative to the total hydrocarbon stream.

Figure 6:
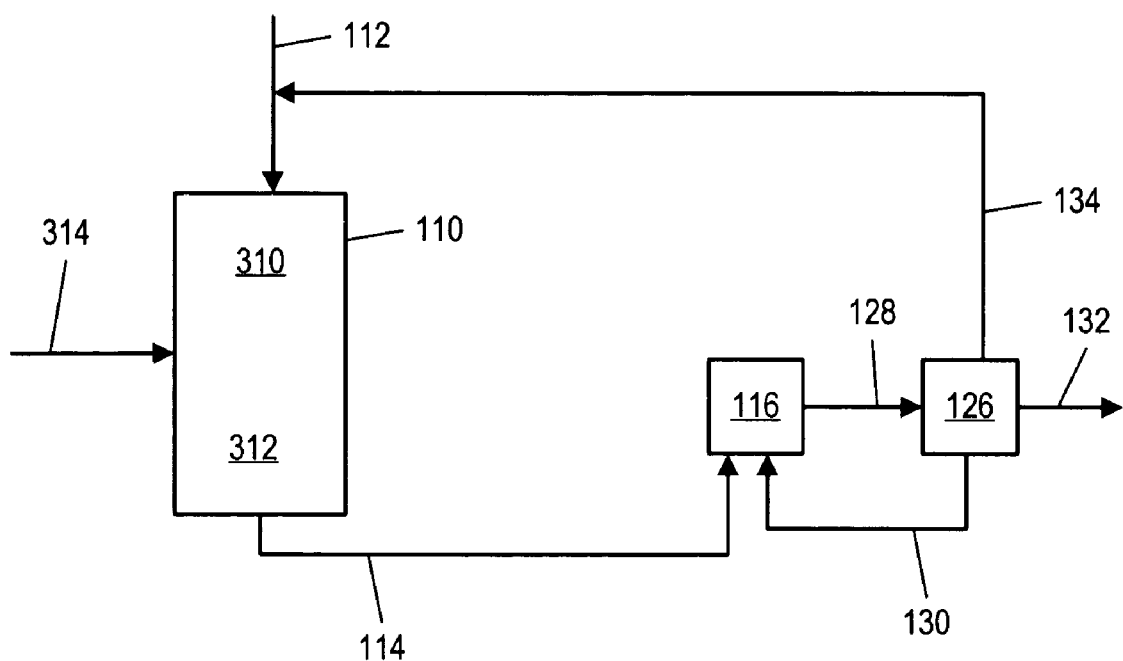
FIG. 6 depicts a schematic diagram of an embodiment of a system for producing branched aliphatic alcohols using a dehydrogenation-isomerization unit with a stacked bed catalyst configuration.

In an embodiment, a catalyst in dehydrogenation-isomerization unit 110 may be used in a stacked bed configuration. A stacked bed configuration may allow for the use of one or more catalysts in the reactor. A catalyst for dehydrogenation of paraffins and a catalyst for isomerization of olefins may enhance the selectivity of the catalysts and/or the process. A stacked bed configuration of dehydrogenation-isomerization unit 110 is depicted for System 300 in FIG. 6. Operating conditions of the stacked bed configuration may be the same as for two-zone system described above for System 200. The first hydrocarbon stream may enter the dehydrogenation zone 310 via first conduit 112.

The dehydrogenation catalyst used in the stacked bed configuration may have nonacidic properties. The term "nonacidic," as used herein, refers to a catalyst that exhibits little skeletal isomerization activity. The dehydrogenation catalyst may include a noble metal, a Group IVA component, an alkali or alkaline earth component, a halogen component and/or a porous carrier material.

In certain embodiments, a noble metal may be dispersed throughout the dehydrogenation catalyst. An amount of noble metal may range between about 0.01 weight percent to about 5 weight percent, calculated on an elemental basis, of the final dehydrogenation catalyst. In certain embodiments, a dehydrogenation catalyst includes about 0.1 weight percent to about 1 weight percent platinum. The noble metal may be incorporated into the catalytic composite by techniques known in the art (e.g., co-precipitation, co-gelation, ion exchange, impregnation, deposition from a vapor phase or from an atomic source) before incorporation of other catalytic components. In some embodiments, a noble metal may be incorporated into the catalytic composite during incorporation of other catalytic components. In other embodiments, a noble metal may be incorporated into the catalytic composite after incorporation of other catalytic components. In certain embodiments, a noble metal may be incorporated by impregnation of the carrier material with a solution or suspension of a decomposable compound of the noble metal. For example, platinum may be added to a catalytic support by commingling the platinum with an aqueous solution of chloroplatinic acid. In other embodiments, optional components (e.g., nitric acid) may be added to the impregnating solution to assist in dispersing or fixing the noble metal in the final catalyst composite.

The Group IVA component, may include germanium, tin, lead or combinations thereof. In some embodiments, a Group IVA component may exist within the catalyst in an oxidation state above that of the noble metal. The Group IVA component may be present as an oxide. In certain embodiments, a Group IVA component may be combined with a carrier material. In some embodiments, a Group IVA component may be combined with the other catalytic components. In other embodiments, a Group IVA component may be dispersed throughout the catalyst. A Group IVA component may range between about 0.01 weight percent to about 5 weight percent, calculated on an elemental basis, of the final catalyst composite. In some embodiments, a catalyst includes about 0.2 weight percent to about 2 weight percent tin.

The Group IVA component may be incorporated in the catalytic composite according to generally known methods (e.g., co-precipitation, co-gelation, ion exchange and impregnation) before other catalytic components are incorporated. In some embodiments, a Group IVA component may be incorporated during incorporation of other catalytic components. In other embodiments, a Group IVA component may be incorporated after other catalytic components are incorporated. In some embodiments, a tin component may be incorporated by co-gelation with the porous carrier material. The tin may be incorporated in an alumina carrier material by mixing a soluble tin compound (e.g., stannous or stannic chloride) with an alumina hydrosol. A gelling agent (e.g., hexamethylenetetraamine) may be added to the tin-alumina hydrosol mixture. The tin-alumina hydrosol mixture may be dropped into an oil bath to form spheres containing alumina and tin. In other embodiments, a germanium component may be impregnated into a carrier material with a solution or suspension of a decomposable compound of germanium (e.g., germanium tetrachloride dissolved in an alcohol). In other embodiments, a lead component may be impregnated from a solution of lead nitrate in water.

In certain embodiments, an alkali or alkaline earth component may be included in the dehydrogenation catalyst. Alkali and alkaline earth component may include, but is not limited to, cesium, rubidium, potassium, sodium, lithium, barium, strontium, calcium and magnesium or mixtures thereof. The alkali or alkaline earth component may exist in the final catalytic composite in an oxidation state above that of the noble metal. The alkali or alkaline earth component may be present as an oxide. In some embodiments, an alkali or alkaline earth metal may be combined with the carrier material. In certain embodiments, an alkali or alkaline earth metal may be combined with other dehydrogenation catalytic components.

In other embodiments, an alkali or alkaline earth component may be dispersed throughout the catalytic composite. An amount of alkali or alkaline earth component may range from about 0.01 weight percent to 15 weight percent, calculated on an elemental basis, of the final catalytic composite. In other embodiments, a dehydrogenation catalyst includes about 1 weight percent to about 3 weight percent potassium. In certain embodiments, an atomic ratio of the alkali or alkaline earth component to the noble metal may be greater than at least about 10.

The alkali or alkaline earth component may be incorporated in the catalytic composite according to generally known methods (e.g., co-precipitation, co-gelation, ion exchange or impregnation) before other catalytic components are incorporated. In some embodiments, an alkali or alkaline earth component may be incorporated during incorporation of other catalytic components. In other embodiments, an alkali or alkaline earth component may be incorporated after other catalytic components are incorporated. For example, a potassium component may be impregnated into the carrier material with a solution of potassium nitrate. An atomic ratio of alkali or alkaline earth component to noble metal may be at least about 10. In certain embodiments, an atomic ratio of the alkali or alkaline earth component to the noble metal component may range from about 15 to about 25.

A porous carrier material used in a dehydrogenation catalyst may include a porous, absorptive support with high surface area from about 25 $m^2/g$ to about 500 $m^2/g$. The porous carrier material may have a melting point greater than the conditions utilized in the dehydrogenation zone. Examples of carrier materials include, but are not limited to, activated carbon, coke, charcoal, silica, silica gel, silicon carbide, synthetically prepared and/or naturally occurring clays and silicates, refractory inorganic oxides, crystalline zeolitic aluminosilicates, naturally occurring or synthetically prepared mordenite and/or faujasite, spinels or combinations of thereof. In certain embodiments, a carrier material may be gamma- or eta-alumina. In some embodiments, clays and silicates may or may not be acid treated (e.g., attapulgite, china clay, diatomaceous earth, fuller's earth, kaolin, kieselguhr, ceramics, porcelain, crushed firebrick, bauxite). Examples of refractory inorganic oxides include alumina, titanium dioxide, zirconium dioxide, chromium oxide, beryllium oxide, vanadium oxide, cerium oxide, hafnium oxide, zinc oxide, magnesia, boria, thoria, silica-alumina, silica-magnesia, chromia-alumina, alumina-boria, and silica-zirconia. Zeolitic aluminosilcates may be, in some embodiments, in the hydrogen form. In other embodiments, zeolitic aluminosilicates may be in a form that may be exchanged with metal cations. Examples of spinels include, but are not limited to, $MgAl_2O_4$, $FeAl_2O_4$, $ZnAl_2O_4$, $CaAl_2O_4$, and other like compounds having the formula $MO-Al_2O_3$ in which M is a metal having a valence of 2.

In certain embodiments, an alumina carrier material used in a dehydrogenation catalyst may be prepared in any suitable manner from synthetic or naturally occurring raw materials. The alumina carrier may be formed in any desired shape (e.g., spheres, pills, cakes, extrudates, powders, granules). The alumina carrier may be utilized in any particle size. In certain embodiments, a sphere shape may be utilized. The particle may be about 1/16 inch in diameter. In certain embodiments, a particle diameter of less than 1/32 inch may be utilized.

Alumina spheres may be prepared, in some embodiments, by converting aluminum metal into an alumina sol. An alumina sol may be prepared by reacting aluminum metal with a suitable peptizing acid and water. The resulting alumina sol and a gelling agent may be dropped into an oil bath to form spherical particles of an alumina gel. The resulting alumina gel may be converted to gamma- or eta-alumina carrier material using known techniques (e.g., by aging, drying and calcining).

In other embodiments, alumina cylinders may be prepared by mulling alumina powder with water and a suitable peptizing agent (e.g., nitric acid) to form an extrudable composition. The composition may be extruded through a suitably sized die then cut to form extrudate particles. Other shapes of the alumina carrier material may be prepared by conventional methods. After the alumina particles are shaped, they may be dried and calcined. The alumina carrier may be subjected to intermediate treatments (e.g., washing with water or a solution of ammonium hydroxide) during preparation.

The dehydrogenation catalyst may include a halogen component. The halogen component may include, but is not limited to, fluorine, chlorine, bromine, iodine or mixtures thereof. The halogen component may be present in a combined state with the porous carrier material. In certain embodiments, a halogen component may be dispersed throughout the catalytic composite. A halogen component may range from at least about 0.2 weight percent to about 15 weight percent, calculated on an elemental basis, of the final catalytic composite. In certain embodiments, a dehydrogenation catalyst contains about 1 weight percent to about 3 weight percent chlorine.

In certain embodiments, a catalyst composition may include at least about 0.2 weight percent, calculated on an elemental basis, of a halogen component. The halogen component in the catalyst may improve the activity of the catalyst for dehydrogenating hydrocarbons. In some embodiments, an active halogen component may suppress carbon formation on the catalyst during the dehydrogenation process. An advantage of the catalyst composition may be that undesirable isomerization or cracking side reactions may be inhibited. In certain embodiments, halogen content may increase the acidity of the catalyst. The acidity may be lowered by steaming the dehydrogenation catalyst to remove excess halogen from the dehydrogenation catalyst.

A halogen component may be incorporated in the catalytic composite in any suitable manner. The incorporation of the halogen may be before preparation of the carrier material. In some embodiments, incorporation of a halogen may be during incorporation of other catalytic components. In other embodiments, incorporation of a halogen may be after other catalytic components are incorporated. In certain embodiments, an alumina sol carrier may contain a halogen, which may contribute to at least some portion of the halogen content in the final catalyst composite. In some embodiments, a halogen component, or a portion thereof, may be added to the catalyst composite during the incorporation of the carrier material with other catalyst components (e.g., using chloroplatinic acid to impregnate the platinum component). In other embodiments, a halogen component or a portion thereof may be added to the catalyst composite by contacting the catalyst with the halogen. In some embodiments, a halogen may be added to the catalyst as a compound, solution, suspension or dispersion containing the halogen, (e.g., hydrochloric acid) before or after other catalyst components are incorporated with the carrier material. In certain embodiments, a halogen component or a portion thereof may be incorporated by contacting the catalyst with a compound, solution, suspension or dispersion containing the halogen in a subsequent catalyst regeneration step. In the regeneration step, carbon deposited on the catalyst as coke during use of the catalyst in a hydrocarbon conversion process may be burned off the catalyst. The noble metal on the catalyst may be redistributed to provide a regenerated catalyst with performance characteristics similar to those of the fresh catalyst. The halogen component may be added during the carbon burn step or during the noble metal redistribution step (e.g., contacting the catalyst with a hydrogen chloride gas). In some embodiments, a halogen component may be added to the catalyst composite by adding the halogen or a compound, solution, suspension or dispersion containing the halogen (e.g., propylene dichloride) to the hydrocarbon feed stream. In other embodiments, a halogen component may be added to the recycle gas during operation of the dehydrogenation unit.

In some embodiments, a dehydrogenation catalyst may include a sulfur component ranging from about 0.01 weight percent to about 10 weight percent, calculated on an elemental basis, of the final catalytic composition. The sulfur component may be incorporated into the catalytic composite in any suitable manner. In certain embodiments, sulfur or a compound containing sulfur (e.g., hydrogen sulfide or a lower molecular weight mercaptan) may be contacted with the catalyst composition in the presence of hydrogen at a temperature ranging from about 10° C. to about 540° C. under anhydrous conditions. A hydrogen to sulfur ratio, in some embodiments, may be about 100.

The dehydrogenation catalyst, in some embodiments, may also contain other, additional components or mixtures thereof, which act alone or in concert, as catalyst modifiers to improve catalyst activity, selectivity or stability. Examples of catalyst modifiers include, but are not limited to, antimony, arsenic, beryllium, bismuth, cadmium, calcium, chromium, cobalt, copper, gallium, gold, indium, iron, lithium, manganese, molybdenum, nickel, rhenium, scandium, silver, tantalum, thallium, titanium, tungsten, uranium, zinc and zirconium. Catalytic modifiers may be added in any suitable manner to the carrier material during preparation of the dehydrogenation catalyst. In other embodiments, catalytic modifiers may be added in any suitable manner after preparation of the dehydrogenation catalyst. In some embodiments, catalytic modifiers may be added in any suitable manner to the catalytic composite before other catalytic components are incorporated. In certain embodiments, catalytic modifiers may be added during incorporation of other catalytic components. In other embodiments, catalytic modifiers may be added after other catalytic components are incorporated. A description of a dehydrogenation catalyst may be found in U.S. Pat. No. 4,506,032 to Imai et al., entitled "Dehydrogenation Catalyst Composition," which is incorporated by reference herein.

The olefinic hydrocarbon stream may pass into isomerization zone 312. In certain embodiments, a temperature decrease from dehydrogenation zone 310 to isomerization zone 312 may be necessary to prevent cracking of the olefinic hydrocarbon stream as it enters the isomerization zone. Cool hydrogen gas may be introduced to dehydrogenation zone 310 via gas conduit 314 to control temperatures in dehydrogenation zone 310. In isomerization zone 312, at least a portion of the olefins in the olefinic hydrocarbon stream may be isomerized to branched olefins to produce a second hydrocarbon stream.

In certain embodiments, an isomerization catalyst may be the same as described for isomerization of olefins in System 200. A description of the isomerization catalyst may be found in U.S. Pat. No. 5,510,306 to Murray, entitled "Process For Isomerizing Linear Olefins to Isoolefins," which is incorporated by reference herein. In some embodiments, about 0.01 weight percent to about 5 weight percent of a noble metal may be added to an isomerization catalyst used in a stacked bed configuration to increase the dehydrogenation activity of the zeolitic catalyst. Common metal incorporation methods (e.g., impregnation, noble metal ion exchange, co-mulling) may be used to incorporate a noble metal (e.g., platinum, palladium) into a zeolite to produce a working catalyst useful in the dehydrogenation-isomerization of paraffins.

The second hydrocarbon stream may exit isomerization zone 312 and enter hydroformylation unit 116 via second conduit 114. At least a portion of the olefins in the second hydrocarbon stream may be hydroformylated to produce a hydroformylation reaction stream as described for System 100. At least a portion of the hydroformylation reaction stream may be separated into a bottoms stream and a top stream using generally known methods. The top stream may be purified and separated as described for System 100 to produce a paraffins and unreacted olefins stream and a crude aliphatic alcohol product stream. The crude aliphatic alcohol product stream may be further purified as described for System 100 to produce an aliphatic alcohol product stream. The hydroformylation reaction mixture stream may enter separator 126 via third conduit 128. In separator 126 at least two streams, a bottom stream and top stream, may be produced as previously described for System 100. The bottom stream may be recycled to hydroformylation unit 116 via bottom stream recycle conduit 130. The top stream may be purified and separated into at least two streams, a paraffins and unreacted olefins stream and a crude aliphatic alcohol product stream. At least a portion of the paraffins and unreacted olefins stream may be recycled, combined with other process streams, sent to other processing units and/or sent to a storage vessel. The crude aliphatic alcohol product stream may be further purified as described for System 100 to produce an aliphatic alcohol product stream. The aliphatic alcohol product stream may include branched aliphatic alcohols (e.g., branched primary aliphatic alcohols). The aliphatic alcohol product stream may be transported via product conduit 132 to be stored on site, sold commercially, transported off-site and/or utilized in other processing units.

At least a portion of the paraffins and unreacted olefins stream may be combined with the first hydrocarbon stream in first conduit 112 to produce a combined hydrocarbon stream via fourth conduit 134. The combined hydrocarbon stream may enter dehydrogenation zone 310 of dehydrogenation-isomerization unit 110 via first conduit 112. The combined hydrocarbon stream entering dehydrogenation zone 310 continues the dehydrogenation-isomerization process and hydroformylation process to produce aliphatic alcohols. By recycling the paraffins and unreacted olefins stream, the yield of product may be maximized. In an embodiment, a paraffins and unreacted olefins stream may directly enter dehydrogenation-isomerization unit 110 through one or more entry points.

In some embodiments, an olefin and paraffin concentration in hydroformylation unit 116 may be adjusted depending on the source of the olefin stream entering the hydroformylation unit. At least a portion of a third hydrocarbon stream may be introduced into the second conduit upstream of the hydroformylation unit as previously described for System 100. The combined stream may be introduced into hydroformylation unit 116 via second conduit 114. At least a portion of the olefins in the combined stream may be hydroformylated to produce aliphatic alcohols.

In an embodiment, a third hydrocarbon stream includes a paraffin content between about 50 percent and about 99 percent relative to the total hydrocarbon content. In certain embodiments, a paraffin content of the third hydrocarbon stream ranges between 60 percent and 90 percent relative to the total hydrocarbon content. In other embodiments, a paraffin content of the third hydrocarbon stream may be greater than 80 percent relative to the total hydrocarbon content.

In an embodiment, an olefin content of a third hydrocarbon stream ranges between about 1 percent and about 99 percent relative to the total hydrocarbon content. In other embodiments, an olefin content of a third hydrocarbon stream may be greater than 80 percent relative to the total hydrocarbon stream.

In certain embodiments, a Fischer-Tropsch feed stream may contain olefins and paraffins of low carbon number (e.g., 4, 5, 6, 7, 8, 9). Typically, a low carbon number feed stream may be sold as fuel, sent to waste and/or recycled to other processing units. The low carbon number feed stream may be less useful in the production of detergents. Typically detergents are made from olefins having a carbon number greater than 7. Conversion of the olefins in the feed stream to branched olefins with higher average carbon number (e.g., 7 to 18) may result in a more commercially valuable use of a low carbon number feed stream (e.g., processed to produce detergents and/or surfactants). The amount and type of branching of the alkyl group may increase the value of the feed stream.

Figure 7:
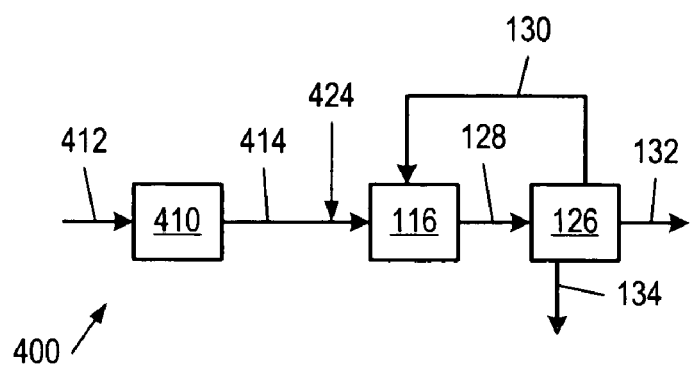
FIG. 7 depicts a schematic diagram of an embodiment of a system for producing branched aliphatic alcohols using a dimerization unit.

A first hydrocarbon stream, including olefins and paraffins may be transported to dimerization unit 410 via first conduit 412 as depicted for System 400 in FIG. 7. Hydrocarbons in the first hydrocarbon stream may have an average carbon number from 4 to 9. In certain embodiments, hydrocarbons in a first hydrocarbon stream may have an average carbon number from 5 to 8. In some embodiments, hydrocarbons in a first hydrocarbon stream may have an average carbon number from 5 to 7. In other embodiments, hydrocarbons in a first hydrocarbon stream may have an average carbon number from 5 to 9. A first hydrocarbon stream may, in some embodiments, be derived from a Fischer-Tropsch process. In dimerization unit 410, at least a portion of the olefins may be dimerized. At least a portion of the dimerized olefins exit dimerization unit 410 as a second hydrocarbon stream via second conduit 414. Depending on the choice of catalyst, the resulting dimer may be branched. The branches of the olefin produced in dimerization unit 410 may include methyl, ethyl and/or longer carbon chains. In an embodiment, dimerized olefins may contain greater than 50 percent methyl branches. In certain embodiments, dimerized olefins may contain greater than 90 percent methyl branches. The dimerized olefins may be separated from the unreacted products through techniques known in the art. One such technique is fractional distillation. At least a portion of the paraffins and unreacted olefins may be separated and recycled back to the dimerization unit and/or sent to other processing units.

In certain embodiments, dimerization unit 410 may have several points of entry to accommodate process streams that vary in composition. Process streams may be from other processing units and/or storage units. Examples of process streams include a diluent hydrocarbon stream, and/or other hydrocarbon streams that include olefins and paraffins derived from other processes. Examples of other processes may include Shell Higher Olefins Process or wax cracking process. As used herein, "entry into the dimerization unit" refers to entry of process streams into the dimerization unit through one or more entry points.

A dimerization catalyst used in dimerization unit 410 may be a homogeneous or heterogeneous catalyst. In certain embodiments, a dimerization catalyst used in dimerization unit 410 may be a catalyst that includes oxides of Group III, Group IVA, Group IVB, Group VIIIA, or combinations thereof. Examples of such oxides include, but are not limited to, nickel oxide, silicon dioxide, titanium dioxide, aluminum oxide or zirconium dioxide. The dimerization catalyst may include an amorphous nickel oxide (NiO) present as a dispersed substantial monolayer on the surfaces of a silica ($SiO_2$) support. The silica support may also include on the surface minor amounts of an oxide of aluminum, gallium or indium such that the ratio of nickel oxide to metal oxide present in the catalyst is within the range from about 4:1 to about 100:1. The dimerization catalyst may be prepared by precipitating a water insoluble nickel salt onto the surface of a silica support. The silica support may be impregnated with a metal oxide. In other embodiments, a dimerization catalyst may be prepared by precipitating a water insoluble nickel salt onto a silica-alumina support. The silica-alumina support may be dealuminized such that the resulting nickel oxide/alumina ratio falls within the range from about 4:1 to about 100:1. The catalyst may be activated by calcination in the presence of oxygen at a temperature with a temperature range from about 300° C. to about 700° C. In some embodiments, the catalyst may be activated by calcination in the presence of oxygen at a temperature with a temperature range from about 500° C. to about 600° C.

Silica useful as a support material may have a surface area within a range from about 100 $m^2/g$ to about 450 $m^2/g$. In an embodiment, a silica surface area may be within the range from about 200 $m^2/g$ to about 400 $m^2/g$. A range of nickel oxide content may be from about 7 percent to about 70 percent by weight. In certain embodiments, a nickel oxide content may be from about 20 percent to about 50 percent by weight, depending on the surface area of the particular support utilized in preparing the catalyst. For a silica support having a surface area of about 300 $m^2/g$, a nickel oxide content may, in some embodiments, range from about 21 percent to about 35 percent by weight. A nickel oxide content may, in other embodiments, be about 28 percent by weight.

The silica support may be in dry granular form or in a hydrogel form prior to precipitation of the nickel oxide precursor compound on the surfaces thereof. Silica hydrogel may be prepared by mixing a water-soluble silicate, (e.g., a sodium or potassium silicate) with a mineral acid. The water-soluble silicate may be washed with water to remove water-soluble ions. The resulting silica hydrogel may be partially dried. In some embodiments, a silica hydrogel may be completely dried.

A nickel oxide precursor may include a water-insoluble nickel salt, such as nickel carbonate, nickel phosphate, nickel nitrate or nickel hydroxide. A water-insoluble nickel salt may be generated in-situ by forming an aqueous mixture of the silica gel and a water-soluble nickel salt. The nickel salt may include, but is not limited to, nickel nitrate, nickel sulfonate, nickel carbonylate, nickel halide. A base may be added to the aqueous mixture to induce precipitation of the water-insoluble nickel salt. The water-insoluble nickel salt may be precipitated in finely divided form within the interstices and on the surface of the silica support. The treated silica support may then be recovered, washed several times and dried.

A second component in the catalyst may be a trivalent metal oxide, which may include, but is not limited to, aluminum, gallium and indium or combinations thereof.

Although a nickel oxide and/or silica catalyst may be active for olefin dimerization, it may deactivate quickly. Deactivation may be from formation of large oligomers that remain attached to the catalyst surface. Large oligomers may act as coke precursors, in some embodiments. A presence of a small amount of the trivalent metal oxide within the catalyst may form acid sites. Acidic sites may promote catalytic activity without promoting unwanted and/or excessive oligomer formation.

A trivalent metal oxide may be incorporated into the silica support by generally known techniques (e.g., precipitation, impregnation). In an embodiment, a trivalent metal oxide may be impregnated into the silica support as an aqueous solution by the addition of a water-soluble salt. The water-soluble metal salt may include, but is not limited to, metal nitrates, metal chlorides or metal sulfates. Once impregnated with a metal salt, the silica support may be dried and calcinated to reduce the metal salt to the oxide form. The silica-trivalent oxide support may further treated to incorporate a nickel oxide layer onto the silica-trivalent metal oxide support.

In an embodiment, silica-trivalent metal oxide (e.g., silica/alumina, silica/gallia or silica/india gel) may be utilized as support material. In certain embodiments, a content of metal oxide (e.g., alumina) present in the support may be low in comparison with the content of nickel oxide. Dealuminization of the silica/alumina gel of relatively high alumina content (e.g., above about 5 percent by weight) may be necessary to reduce the content of alumina. Dealuminization may be accomplished by known techniques (e.g., extraction of the aluminum with an organic or inorganic acid). Organic or inorganic acids may include, but are not limited to, nitric acid, sulfuric acid, hydrochloric acid, chloroacetic acid or ethylene diamine tetraacetic acid. Extraction may be accomplished by adding the acid to an aqueous dispersion of the alumino silicate followed by stirring, decantation and washing with water. The process may be repeated one or more times until the desired alumina content is achieved. The solids are then dried, calcined and further treated to incorporate the nickel oxide layer onto the silica/alumina support.

A content of trivalent metal oxide with respect to the content of the nickel oxide present in the silica support may be significant. In certain embodiments, when the content of trivalent metal oxide is too low (e.g., above a nickel oxide to trivalent metal oxide ratio of about 100 to 1) then the yield of dimer decreases and the catalyst may tend to deactivate quickly. In certain embodiments, a content of trivalent metal oxide may be high (e.g., below a nickel oxide to trivalent metal oxide ratio of about 4 to 1). A high trivalent metal oxide content may lower the yield of dimer. In some embodiments, a high trivalent metal oxide content may raise an average content of methyl branching in the dimerized olefin product. In certain embodiments, a content of trivalent metal oxide may be such that the ratio of nickel oxide to trivalent metal oxide falls within the range from about 4:1 to about 30:1. In other embodiments, a content of trivalent metal oxide may be such that the ratio of nickel oxide to trivalent metal oxide is between about 5:1 to about 20:1. In certain embodiments, a ratio of nickel oxide to trivalent metal oxide may be between about 8:1 to about 15:1.

In certain embodiments, a dimerization catalyst may contain from about 21 percent to about 35 percent by weight of nickel oxide and about 1 percent to about 5 percent by weight of trivalent metal oxide, based on the total weight of nickel oxide, trivalent metal oxide and silica. In certain embodiments, a dimerization catalyst may include from about 1.5 percent to about 4 percent by weight trivalent metal oxide based on the total weight of nickel oxide, trivalent metal oxide and silica.

Preparation of dimerization catalysts are described in U.S. Pat. No. 5,849,972 to Vicari et al., entitled "Oligomerization Of Olefins To Highly Linear Oligomers, and Catalyst For This Purpose," and U.S. Pat. No., 5,169,824 to Saleh et al., entitled "Catalyst Comprising Amorphous NiO On Silica/Alumina Support," both of which are fully incorporated herein by reference.

Conversion of olefins in the first hydrocarbon feed stream to dimers in dimerization unit 410, may be carried out as a batch, continuous (e.g., using a fixed bed), semi-batch or multi-step process. In a batch process, the catalyst may be slurried with the first hydrocarbon feed stream. Temperature conditions for the dimerization reaction may range from about 120° C. to about 200° C. In an embodiment, a reaction temperature may range from about 150° C. to about 165° C. Reaction temperatures may be controlled with evaporative cooling (e.g., the evaporation of lighter hydrocarbon fractions from the reaction mixture may control the reaction temperature).

At least a portion of the produced dimerized olefins may be transported to other processing units (e.g., an alkylation unit and hydroformylation unit) via second conduit 414. Produced dimerized olefins may include olefins with an average carbon number from 8 to 18. In certain embodiments, produced dimerized olefins may include olefins with an average carbon number from 10 to 16. In some embodiments, produced dimerized olefins may include olefins with an average carbon number from 10 to 14. In other embodiments, produced dimerized olefins may include olefins with an average carbon number from 14 to 18.

Figure 8:
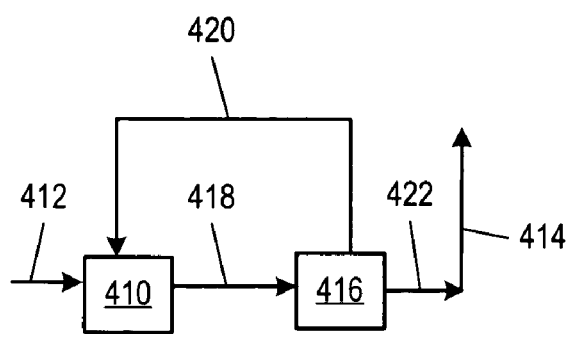
FIG. 8 depicts a schematic diagram of an embodiment of a separation unit to separate produced dimerized olefins from a reaction mixture.

Produced dimerized olefins may be separated, if desired, from the reaction mixture through techniques known in the art (e.g., distillation, adsorption/desorption). In an embodiment, at least a portion of second hydrocarbon stream may exit dimerization unit 410 and enter separation unit 416 via conduit 418 as depicted in FIG. 8. In separation unit 416 the reaction mixture may be separated into a produced dimerized olefins stream and a paraffins and unreacted olefins stream through fractional distillation. The paraffins and unreacted olefins stream may contain hydrocarbons with a carbon number less than 9. At least a portion of the paraffins and unreacted olefins stream may be introduced into dimerization unit 410 via conduit 420. Produced dimerized olefins stream may exit separation unit 416 and be introduced into second conduit 414 via conduit 422.

At least a portion of the second hydrocarbon stream may be transported to hydroformylation unit 116 via second conduit 414. At least a portion of a third hydrocarbon stream may be introduced into second conduit 414 via fourth conduit 424 to produce a combined hydrocarbon stream. The combined stream may enter hydroformylation unit 116. At least a portion of the olefins in the second hydrocarbon stream may be hydroformylated in hydroformylation unit 116 to produce aliphatic alcohols. The hydroformylation and subsequent purification steps may be performed under conditions described for System 100.

As previously described for System 100, at least a portion of the third hydrocarbon stream may be used to regulate the olefin concentration in hydroformylation unit 116 at a concentration sufficient to maximize hydroformylation of the olefin. In addition, a third hydrocarbon stream may optimize the ratio of linear to branched aliphatic alcohols. The third hydrocarbon stream may be, but is not limited to, a hydrocarbon stream containing olefins, paraffins and/or hydrocarbon solvents.

In an embodiment, a third hydrocarbon stream may include olefins and paraffins. In certain embodiments, an average carbon number of the hydrocarbons in the third hydrocarbon stream ranges from 7 to 18. In some embodiments, a paraffin content of the third hydrocarbon stream may be between about 60 percent and about 90 percent by weight. In other embodiments, a paraffin content of the third hydrocarbon stream may be greater than 90 percent by weight.

In an embodiment, an olefin content of a third hydrocarbon stream ranges between about 1 percent and about 99 percent relative to the total hydrocarbon content. In certain embodiments, an olefin content of the third hydrocarbon stream may be between about 45 percent and about 99 percent by weight. In other embodiments, an olefin concentration of the third hydrocarbon stream may be greater than 80 percent by weight.

The hydroformylation reaction mixture stream may enter separator 126 via third conduit 128. In separator 126 at least two streams, bottom stream and a top stream may be produced. The bottom stream may be recycled back to hydroformylation unit 116 via recycle conduit 130. The top stream may be purified and separated to produce at least two streams, a paraffins and unreacted olefins stream and a crude aliphatic alcohol product stream. Methods used for purification and separation, in certain embodiments, may be the same as those described for System 100. The crude aliphatic alcohol product stream may be further purified to form an aliphatic alcohol product stream. The aliphatic alcohol product stream may include branched aliphatic alcohols (e.g., branched primary alcohols). The aliphatic alcohol product stream may exit separator 126 via product conduit 132 to be stored on site, sold commercially, transported off-site, and/or utilized in other processing units. At least a portion of the paraffins and unreacted olefins stream may exit separator 126 and be recycled, combined with other process streams, sent to other processing units and/or be stored on site via fourth conduit 134. In certain embodiments, a paraffins and unreacted olefins stream may be further separated into a hydrocarbons stream including paraffins and unreacted olefins with a carbon number less than 9. The hydrocarbon stream including paraffins and unreacted olefins with a carbon number less than 9 may be introduced upstream of and/or into the dimerization unit.

In certain embodiments, a hydrocarbon stream from a dimerization unit may be combined with a hydrocarbon stream from an isomerization unit to produce a combined stream. The combined stream may be introduced into a hydroformylation unit. Combining streams from the two units may result in a more economically valuable process to produce aliphatic alcohols. A first hydrocarbon stream, that includes paraffins and olefins may enter dimerization unit 410 via first conduit 412 as depicted for System 500, in FIG. 9. In an embodiment, a first hydrocarbon stream, may be produced from a Fischer-Tropsch process. An average carbon number of hydrocarbons in a first hydrocarbon stream may range from 4 to 9. In certain embodiments, hydrocarbons in a first hydrocarbon stream may have an average carbon number range from 5 to 8. In some embodiments, an average carbon number of hydrocarbons in a first hydrocarbon stream may range from 5 to 7. In other embodiments, an average carbon number of hydrocarbons in a first hydrocarbon stream may range from 7 to 9.

In dimerization unit 410, at least a portion of the olefins may be dimerized as previously described for System 400. At least a portion of the dimerized olefins exit dimerization unit 410 as a second hydrocarbon stream. Depending on the choice of catalyst, the resulting dimer may be branched. Branches of the olefin produced in dimerization unit 410 may include methyl, ethyl and/or longer carbon chains. In an embodiment, produced dimerized olefins may contain greater than 50 percent methyl branches. In an alternate embodiment, produced dimerized olefins may contain greater than 90 percent methyl branches. The average carbon number of produced dimerized olefins may range from 8 to 18. In some embodiments, an average carbon number of produced dimerized olefins may range from 10 to 16. In certain embodiments, an average carbon number of produced dimerized olefins may range from 10 to 14. In other embodiments, an average carbon number of produced dimerized olefins may range from 14 to 18. Produced dimerized olefins may be separated from the reactor product using generally known techniques (e.g., fractional distillation). In an embodiment, produced dimerized olefins may be separated from the reaction mixture and processed as previously described for System 400. $^1$H NMR analysis of the composition and determination of the branching of the dimerized olefins may be performed. The second hydrocarbon stream may be transferred to other processing units, (e.g., separation units, alkylation units, hydroformylation units) or to storage units through a conduit.

At least a portion of the second hydrocarbon stream may exit dimerization unit 410 and enter hydroformylation unit 116 via second conduit 414. A fourth hydrocarbon stream may be introduced directly into hydroformylation unit 116 through one or more hydroformylation unit ports. At least a portion of a fourth hydrocarbon stream may be introduced into second conduit 414 via fifth conduit 512 upstream of hydroformylation unit 116 to produce a combined stream. The fourth hydrocarbon stream may be a stream exiting from isomerization unit 514.

Isomerization unit 514 may be fed by a third hydrocarbon stream containing paraffins and unreacted olefins via a sixth conduit 516. In isomerization unit 514, at least a portion of the olefins in the third hydrocarbon stream may be isomerized to branched olefins to produce the fourth hydrocarbon stream. A third hydrocarbon stream may include hydrocarbons with an average carbon number from 7 to 18. In certain embodiments, a third hydrocarbon stream may include hydrocarbons with an average carbon number from 10 to 17. In some embodiments, a third hydrocarbon stream may include hydrocarbons with an average carbon number from 10 to 13. In other embodiments, a third hydrocarbon stream may include hydrocarbons with an average carbon number from 14 to 17. In some embodiments, a third hydrocarbon stream includes alpha-olefins. In certain embodiments, a third hydrocarbon stream is a stream derived from a Fischer-Tropsch process. The alpha-olefin content of the third hydrocarbon stream may be greater than 70 percent of the total amount of olefins in the third hydrocarbon stream. In isomerization unit 514, at least a portion of the olefins in the third hydrocarbon stream may be isomerized to branched olefins (e.g., isoolefins) to produce a fourth hydrocarbon stream.

In certain embodiments, isomerization unit 514 may have several points of entry to accommodate process streams, which may vary in composition. Process streams may be from other processing units and/or storage units. Examples of process streams include, but are not limited to, a diluent hydrocarbon stream, and/or other hydrocarbon streams that include olefins and paraffins derived from other processes. As used herein, "entry into the isomerization unit" refers to entry of process streams into the isomerization unit through one or more entry points.

Conditions for olefin isomerization in isomerization unit 514 may be controlled such that the number of carbon atoms in the olefins before and after the isomerization is substantially the same. U.S. Pat. No. 5,648,584 to Murray, entitled "Process for Isomerizing Linear Olefins to Isoolefins" and U.S. Pat. No. 5,648,585 to Murray et al., entitled "Process for Isomerizing Linear Olefins to Isoolefins," both of which are incorporated herein by reference; describe catalysts and process conditions to skeletally isomerize linear olefins to branched olefins.

In an embodiment, linear olefins in a third hydrocarbon stream are isomerized in isomerization unit 514 by contacting at least a portion of the third hydrocarbon stream with a zeolite catalyst. The zeolite catalyst may have at least one channel with a crystallographic free channel diameter ranging from greater than 4.2 Å and less than 7 Å. The zeolite catalyst may have an elliptical pore size large enough to permit entry of a linear olefin and diffusion, at least partially, of a branched olefin. The pore size of the zeolite catalyst may also be small enough to retard coke formation.

Temperatures at which the olefin isomerization may be conducted in isomerization unit 514 range from about 200° C. to about 500° C. Temperatures in isomerization unit 514 are, in some embodiments, kept below the temperature at which the olefin will crack extensively. As used herein, "cracking" refers to the process of thermally degrading molecules into smaller molecules. To inhibit cracking, low temperatures may be used at low feed rates. In certain embodiments, lower temperatures may be used when the amount of oxygenates present in the process stream is low. Higher feed rates may be desirable to increase the production rate of isomerised products. Higher feed rates may be used, in some embodiments, when operating at higher reaction temperatures. The reaction temperature, however, should be set such that cracking to lower boiling weight products is minimized. For example, greater than 90 percent of linear $C_{12}$-$C_{14}$ olefins may be converted to branched olefins at 230° C. at a feed rate of 60 grams per hour per 6 grams of catalyst with minimal cracking. Pressures maintained in isomerization unit 514 may be at a hydrocarbon partial pressure ranging from about 0.1 atmospheres (10 kPa) to about 20 atmospheres (2026 kPa). In an embodiment, a partial pressure may range from above about 0.5 atmospheres (51 kPa) to about 10 atmospheres (1013 kPa).

The fourth hydrocarbon stream may be combined with the second hydrocarbon stream in second conduit 414. Hydrocarbons in the fourth hydrocarbon stream may have an average carbon number from 7 to 18. In certain embodiments, hydrocarbons in the fourth hydrocarbon stream may have an average carbon number from 10 to 17. In some embodiments, hydrocarbons in the fourth hydrocarbon stream may have an average carbon number from 10 to 13. In other embodiments, an average carbon number of the hydrocarbons in a feed stream may range from 14 to 17.

In an embodiment, a fifth hydrocarbon stream may be introduced into hydroformylation unit 116 through one or more hydroformylation ports. In certain embodiments, at least a portion of a fifth hydrocarbon stream may be introduced into second conduit 414 upstream of hydroformylation unit 116 via seventh conduit 518 to produce a combined stream. The combined stream may enter hydroformylation unit 116 and at least a portion of the olefins in the combined stream may be hydroformylated to produce a hydroformylation reaction stream.

Hydroformylation reaction conditions may be the same as previously described for System 100. Separation of the hydroformylation reaction stream into at least two streams, a bottom stream and a top stream, may be performed as previously described for System 100. The bottom stream may be recycled to the hydroformylation unit, in certain embodiments. The top stream may be further purified and separated into at least two streams, a paraffins and unreacted olefins stream and a crude aliphatic alcohol product stream, using techniques generally known. In certain embodiments, techniques used for purification and separation of a top stream may be the same as those described for System 100. The crude aliphatic alcohol product stream may be further purified to produce an aliphatic alcohol product stream using techniques previously described for System 100. The aliphatic alcohols in the aliphatic alcohol product stream may be branched aliphatic alcohols.

The fourth and fifth hydrocarbon streams may be used to regulate the olefin concentration in hydroformylation unit 116 at a concentration sufficient to maximize hydroformylation of the olefin. The fourth and fifth hydrocarbon streams may be, but are not limited to, a hydrocarbon stream containing olefin, paraffins and/or hydrocarbon solvents. In an embodiment, a paraffin content of the fourth and fifth hydrocarbon streams may be greater than 50 percent and less than 99 percent relative to the total hydrocarbon content. In certain embodiments, a paraffin content of the fourth and fifth hydrocarbon streams may be between about 60 percent and about 90 percent relative to the total hydrocarbon content. In other embodiments, a paraffin content may be greater than 90 percent relative to the total hydrocarbon content.

In an embodiment, an olefin content of a fifth hydrocarbon stream ranges between about 1 percent and about 99 percent relative to the total hydrocarbon content. In certain embodiments, an olefin content of a fifth hydrocarbon stream ranges between about 45 percent and about 95 percent. In other embodiments, an olefin content of a fifth hydrocarbon stream may be greater than 80 percent relative to the total hydrocarbon stream.

A combined stream may include, but is not limited to, a second hydrocarbon stream, a fourth hydrocarbon stream, a fifth hydrocarbon stream and/or combinations thereof, may be introduced into hydroformylation unit 116 via second conduit 414. An advantage of combining the streams may be that overall production of aliphatic alcohols may be increased with fewer throughputs. At least a portion of the olefins in the combined stream may be hydroformylated under conditions previously described for System 100 to produce aliphatic alcohols. An average carbon number of the alcohols produced in hydroformylation unit 116 may be less than 20. In certain embodiments, an average carbon number of alcohols produced in hydroformylation unit 116 may range from 7 to 19. In some embodiments, an average number of alcohols produced in hydroformylation unit 116 may range from 10 to 18. In other embodiments, an average number of alcohols produced in a hydroformylation unit 116 may range from 14 to 19.

The hydroformylation reaction mixture stream may enter separator 126 via third conduit 128. Separation of the aliphatic alcohol product from at least a portion of the hydroformylation reaction stream may be performed in separation unit 126. The separation may produce at least two streams, a bottom stream and a top stream using generally known techniques (e.g., distillation). At least a portion of the bottom stream may be recycled to hydroformylation unit 116 via recycle conduit 130. The top stream may be further purified and separated to produce at least two streams, a paraffins and unreacted olefins stream and a crude aliphatic alcohol product stream using techniques previously described for System 100. At least a portion of the crude aliphatic alcohol product stream may be further purified to produce an aliphatic alcohol product stream using generally known techniques. The aliphatic alcohol product stream may exit separation unit 126 and be transported via product conduit 132 to be stored on site, sold commercially, transported off-site, and/or utilized in other processing units.

At least a portion of the paraffins and unreacted olefins stream may exit separation unit 126 and be transported via fourth conduit 134 to another processing unit, and/or storage vessel. In certain embodiments, a paraffins and unreacted olefins stream may be further separated into a hydrocarbons stream including paraffins and unreacted olefins with a carbon number less than 8. The hydrocarbon stream including paraffins and unreacted olefins with a carbon number less than 8 may be introduced upstream of the dimerization unit and/or into the dimerization unit.

In certain embodiments, to reduce production costs of producing branched aliphatic alcohols, a stream containing a significant amount of paraffins and a minor amount of olefins may first be isomerized then hydroformylated to form branched aliphatic alcohols. Processing a stream containing a minor amount of olefins through an isomerization unit prior to hydroformylation may save production time, dehydrogenation catalyst cost and/or enhance the overall economic viability of the stream. In some embodiments, after hydroformylation, paraffins and unreacted olefins may be recycled to a dehydrogenation unit to produce a stream enriched in olefins. The enriched olefins stream may be recycled into an isomerization unit.

Figure 10:
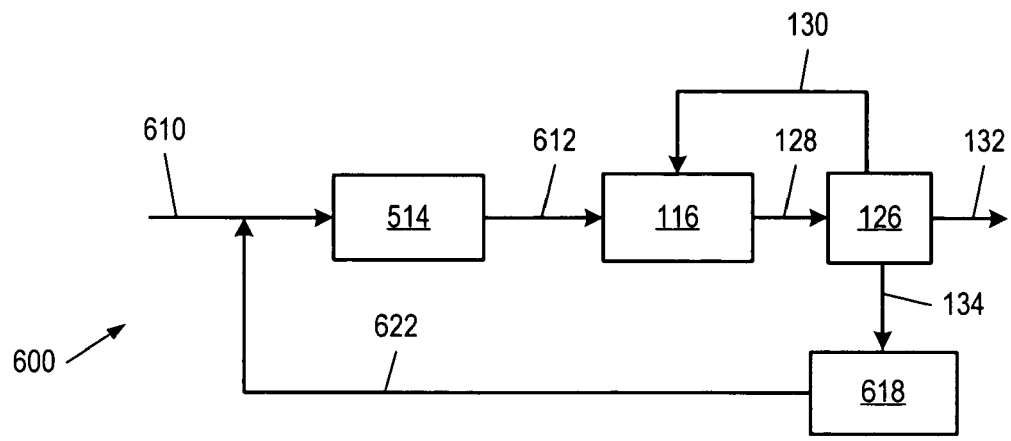
FIG. 10 depicts a schematic diagram of an embodiment of a system for producing branched aliphatic alcohols using an olefin isomerization unit.

Referring to System 600 in FIG. 10, a first hydrocarbon stream may be introduced into isomerization unit 514 via first conduit 610. In isomerization unit 514, at least a portion of the olefins in the first hydrocarbon stream may be isomerized to branched olefins to produce a second hydrocarbon stream. A first hydrocarbon stream may include hydrocarbons with an average carbon number from 7 to 18. In certain embodiments, a first hydrocarbon stream may include hydrocarbons with an average carbon number from 10 to 17. In some embodiments, a first hydrocarbon stream may include hydrocarbons with an average carbon number from 10 to 17. In other embodiments, a first hydrocarbon stream may include hydrocarbons with an average carbon number from 14 to 17. A first hydrocarbon stream may be a stream derived from a Fischer-Tropsch process. A first hydrocarbon stream includes alpha-olefins, in some embodiments. The alpha-olefin content of the first hydrocarbon stream may be greater than 70 percent of the total amount of olefins in the first hydrocarbon stream. In isomerization unit 514, at least a portion of the olefins in the first hydrocarbon stream may be isomerized to branched olefins (e.g., isoolefins) to produce a second hydrocarbon stream.

Conditions for olefin isomerization in isomerization unit 514 may be controlled such that the number of carbon atoms in the olefins before and after the isomerization is substantially the same. U.S. Pat. No. 5,648,584 to Murray, entitled "Process for Isomerizing Linear Olefins to Isoolefins" and U.S. Pat. No. 5,648,585 to Murray et al., entitled "Process for Isomerizing Linear Olefins to Isoolefins," both of which are incorporated herein by reference; describe catalysts and process conditions to skeletally isomerize linear olefins to branched olefins.

In an embodiment, linear olefins in a first hydrocarbon stream are isomerized in isomerization unit 514 by contacting at least a portion of the first hydrocarbon stream with a zeolite catalyst. The zeolite catalyst may have at least one channel with a crystallographic free channel diameter ranging from greater than 4.2 Å and less than 7 Å. The zeolite catalyst may have an elliptical pore size large enough to permit entry of a linear olefin and diffusion, at least partially, of a branched olefin. The pore size of the zeolite catalyst may also be small enough to retard coke formation.

Temperatures at which the olefin isomerization may be conducted range from about 200° C. to about 500° C. Temperatures in isomerization unit 514 are, in some embodiments, kept below the temperature at which the olefin will crack extensively. To inhibit cracking, low temperatures may be used at low feed rates. In certain embodiments, lower temperatures may be used when the amount of oxygenates present in the process stream is low. Higher feed rates may be desirable to increase the production rate of isomerised products. Higher feed rates may be used, in some embodiments, when operating at higher reaction temperatures. The reaction temperature, however, should be set such that cracking to lower boiling weight products is minimized. For example, greater than 90 percent of linear olefins may be converted to branched olefins at 230° C. at a feed rate of 60 grams per hour per 6 grams of catalyst with minimal cracking. Pressures maintained in isomerization unit 514 may be at a hydrocarbon partial pressure ranging from about 0.1 atmosphere (10 kPa) to about 20 atmospheres (2026 kPa). In an embodiment, partial pressure may range from above about 0.5 atmosphere (51 kPa) to about 10 atmospheres (1013 kPa).

The branched olefin produced in isomerization unit 514 may include methyl, ethyl and/or longer carbon chain branches. The isomerized olefin composition may be analyzed by $^1$H NMR as previously described for System 100.

Isomerization unit 514 may produce a second hydrocarbon stream that includes olefins and paraffins. At least a portion of the second hydrocarbon stream contains branched olefins. The second hydrocarbon stream may exit isomerization unit 514 via second conduit 612 and be introduced into hydroformylation unit 116. At least a portion of the olefins in the second hydrocarbon stream may be hydroformylated under conditions previously described for System 100 to produce aliphatic alcohols.

Figure 11:
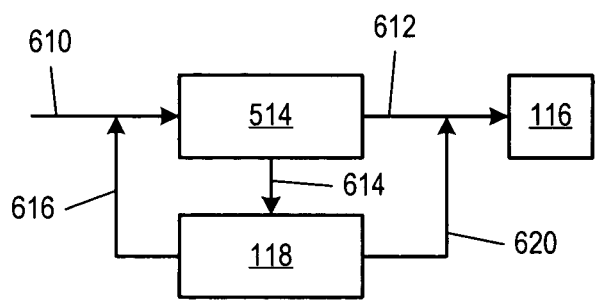
FIG. 11 depicts a schematic diagram of an embodiment of a system for producing branched aliphatic alcohols using a isomerization unit and a separation unit to separate branched olefins from linear olefins and paraffins.

In an embodiment, olefins may be separated, if desired, from the second hydrocarbon stream through techniques generally known in the art (e.g., distillation, molecular sieves, extraction, adsorption, adsorption/desorption, and/or membranes). Referring to FIG. 11, a second hydrocarbon stream may exit isomerization unit 514 and enter separation unit 118 via separation conduit 614. Separation unit 118 may produce at least two streams, a branched olefins stream and a linear olefins and paraffins stream. In separation unit 118, the second hydrocarbon stream may be contacted with molecular sieves (e.g., zeolite or urea) of the correct pore size for absorption of branched olefins and/or linear olefins and paraffins. Subsequent desorption of at least a portion of the branched olefins and/or at least a portion of the linear olefins and paraffins from the molecular sieves may produce at least two streams, a branched olefins stream and a linear olefins and paraffins stream.

Separation unit 118 may include a fixed bed containing adsorbent for separation of the second hydrocarbon stream to produce a branched olefin stream and a linear olefins and paraffins stream. Separation temperatures in separation unit 118 may range from about 100° C. to about 400° C. In some embodiments, separation temperatures may range from 180° C. to about 380° C. Separations in separation unit 118 may be conducted at a pressure ranging from about 2 atmospheres (202 kPa) to about 7 atmospheres (710 kPa). In some embodiments, a pretreatment of a second hydrocarbon stream may be performed to prevent adsorbent poisoning.

At least a portion of the linear olefins and paraffins stream may be recycled, transported to other processing units and/or stored on site. In an embodiment, at least a portion of the linear olefins and paraffins stream may be combined with first hydrocarbon stream in first conduit 610 via linear olefin and paraffin recycle conduit 616. The combined stream may enter isomerization unit 514 via first conduit 610 to continue the process to produce isomerized olefins. In some embodiments, a linear olefins and paraffins stream may be introduced directly into isomerization unit 514. In some embodiments, a linear olefins and paraffins stream may be introduced into dehydrogenation unit 618.

At least a portion of the branched olefins stream may be transported and utilized in other processing streams and/or stored on site via branched olefins conduit 620. In some embodiments, at least a portion of a branched olefins stream may exit separation unit 118 and be combined with second hydrocarbon stream in second conduit 612 upstream of hydroformylation unit 116 via branched olefins conduit 620. In other embodiments, at least a portion of a branched olefins stream may exit separation unit 118 and be introduced directly into a hydroformylation unit.

Referring to FIG. 10, the second hydrocarbon stream may exit isomerization unit 514 and via second conduit 612 and enter hydroformylation unit 116. Hydroformylation reaction conditions may be the same as previously described for System 100. Separation of the hydroformylation reaction stream into at least two streams, a bottom stream and a top stream, may be performed as previously described for System 100. The bottom stream may be recycled to the hydroformylation unit, in certain embodiments. The top stream may be further purified and separated into at least two streams, a paraffins and unreacted olefins stream and a crude aliphatic alcohol product stream, using techniques generally known. In certain embodiments, techniques used to purification and separation atop stream may be the same as those described for System 100. The crude aliphatic alcohol product stream may be further purified to produce an aliphatic alcohol product stream using techniques previously described for System 100. The aliphatic alcohols in the aliphatic alcohol product stream may be branched aliphatic alcohols.

In some embodiments, a third hydrocarbon stream may be used to regulate the olefin concentration in hydroformylation unit 116 at a concentration sufficient to maximize hydroformylation of the olefin. The third hydrocarbon streams may be, but is not limited to, a hydrocarbon stream containing olefin, paraffins and/or hydrocarbon solvents. In an embodiment, a third hydrocarbon stream may include olefins and paraffins. In certain embodiments, an average carbon number of the hydrocarbons in the third hydrocarbon stream ranges from 7 to 18. In some embodiments, a paraffin content of the third hydrocarbon stream may be between about 60 percent and about 90 percent by weight. In other embodiments, a paraffin content of the third hydrocarbon stream may be greater than 90 percent by weight.

In an embodiment, an olefin content of a third hydrocarbon stream ranges between about 1 percent and about 99 percent relative to the total hydrocarbon content. In certain embodiments, an olefin content of the third hydrocarbon stream may be between about 45 percent and about 99 percent by weight. In other embodiments, an olefin concentration of the third hydrocarbon stream may be greater than 80 percent by weight.

The hydroformylation reaction mixture stream may enter separator 126 via third conduit 128. Separation of the aliphatic alcohol product from at least a portion of the hydroformylation reaction stream may be performed in separation unit 126. The separation may produce at least two streams, a bottom stream and a top stream, using generally known techniques (e.g., distillation). At least a portion of the bottom stream may be recycled to hydroformylation unit 116 via recycle conduit 130. The top stream may be further purified and separated to produce at least two streams, a paraffins and unreacted olefins stream and a crude aliphatic alcohol product stream using techniques previously described for System 100. At least a portion of the crude aliphatic alcohol product stream may be further purified to produce an aliphatic alcohol product stream using generally known techniques. The aliphatic alcohol product stream may exit separation unit 126 and be transported via product conduit 132 to be stored on site, sold commercially, transported off-site, and/or utilized in other processing units.

At least a portion of the paraffins and unreacted olefins stream may exit separation unit 126 and be transported via fourth conduit 134 to another processing unit, and/or storage vessel. At least a portion of the separated paraffins and unreacted olefins may enter dehydrogenation unit 618 via fourth conduit 134. An average carbon number of the hydrocarbons in the paraffins and unreacted olefins stream may range from 7 to 18. In certain embodiments, an average carbon number of the paraffins and unreacted olefins stream may range from 10 to 17. In some embodiments, an average carbon number of the paraffins and unreacted olefins stream may range from 10 to 13. In other embodiments, an average carbon number of the hydrocarbons in the paraffins and unreacted olefins stream may range from 14 to 17.

In an embodiment, at least a portion of the paraffins and unreacted olefins stream may be introduced into dehydrogenation unit 618 via fourth conduit 134. At least a portion of the unreacted paraffins in the hydrocarbon stream may be dehydrogenated to produce an olefinic hydrocarbon stream by use of a catalyst selected from a wide range of catalyst types. For example, the catalyst may be based on a metal and/or a metal compound deposited on a porous support. The metal or metal compound may include, but is not limited to, chrome oxide, iron oxide and noble metals.

Techniques of preparing catalysts, for performing the dehydrogenation step and for performing associated separation steps are generally known. For example, suitable procedures for preparing catalysts and performing the dehydrogenation step are described in U.S. Pat. No. 5,012,021 to Vora et al., entitled "Process For the Production of Alkyl Aromatic Hydrocarbons Using Solid Catalysts;" U.S. Pat. No. 3,274,287 to Moore et al., entitled "Hydrocarbon Conversion Process and Catalyst;" U.S. Pat. No. 3,315,007 to Abell et al., entitled "Dehydrogenation of Saturated Hydrocarbons Over Noble-Metal Catalyst;" U.S. Pat. No. 3,315,008 to Abell et al., entitled "Dehydrogenation of Saturated Hydrocarbons Over Noble-Metal Catalyst;" U.S. Pat. No. 3,745,112 to Rausch, entitled "Platinum-Tin Uniformly Dispersed Hydrocarbon Conversion Catalyst and Process;" U.S. Pat. No. 4,506,032 to Imai et al., entitled "Dehydrogenation Catalyst Composition" and U.S. Pat. No. 4,430,517 to Imai et al., entitled "Dehydrogenation Process Using a Catalytic Composition," all of which are incorporated by reference herein.

Reaction conditions in dehydrogenation unit 618 may be varied to control unwanted side products (e.g., coke, dienes oligomers, cyclized hydrocarbons) and control double bond position in the olefin. In certain embodiments, temperatures may range from greater than 300° C. to less than 700° C. In other embodiments, a dehydrogenation reaction temperature may range from about 450° C. to about 550° C. During dehydrogenation, pressures in dehydrogenation unit 618 may range from greater than 0.010 atmosphere (1 kPa) to about 25.0 atmospheres (2534 kPa). In an embodiment, a total pressure of dehydrogenation unit 618 during the reaction may range from about 0.10 atmosphere (10 kPa) to about 15.0 atmospheres (15200 kPa). In certain embodiments, pressure in dehydrogenation unit 618 may range from about 1.0 atmosphere (101 kPa) to about 5.0 atmospheres (510 kPa). In order to prevent coke from forming, hydrogen may be fed into dehydrogenation unit 618 together with the paraffins and unreacted olefins stream. The hydrogen to paraffins molar ratio may be set between about 0.1 moles of hydrogen to about 20 moles of paraffins. In some embodiments, a hydrogen to paraffin molar ratio is about 1 to 10.

The amount of time (e.g., the residence time) that a process stream remains in dehydrogenation unit 618 may determine, to some extent, the amount of olefins produced. Generally, the longer a process stream remains in dehydrogenation unit 618, the conversion level of paraffins to olefins increases until an olefin-paraffin thermodynamic equilibrium is obtained. Residence time of the paraffins and unreacted olefins stream in dehydrogenation unit 618 may be such that the conversion level of paraffins to olefins may be kept below 50 mole percent. In certain embodiments, conversion level of paraffins to olefins may be kept in the range of from 5 to 30 mole percent. By keeping the conversion level low, side reactions may be prevented (e.g., diene formation and cyclization reactions).

Dehydrogenation unit 618 receives at least a portion of the paraffins and unreacted olefins stream from separation unit 126 and produces an olefinic hydrocarbon stream. The olefinic hydrocarbon stream may include paraffins. The concentration of the olefins in the olefinic hydrocarbon stream may be between 5 and 50 percent by weight. In certain embodiments, a concentration of olefins may range from 10 to 20 percent by weight. The olefins produced in dehydrogenation unit 618 may be predominately linear olefins. The average carbon number of the hydrocarbons in the olefinic stream may range from 7 to 18. The average carbon number of the hydrocarbons in the olefinic stream ranges, in certain embodiments, from about 10 to 17. In some embodiments, hydrocarbons in the olefinic stream may have an average carbon number from 10 to 13. In other embodiments, an average carbon number of the hydrocarbons in the olefinic stream may range from 14 to 17.

In certain embodiments, at least a portion of non-converted paraffins may be separated from the olefinic stream and, if desired, the non-converted paraffins may be recycled to dehydrogenation unit 618 to undergo dehydrogenation. Such separation may be accomplished by extraction, distillation or adsorption techniques.

In some embodiments, at least a portion of a paraffinic hydrocarbon stream may be introduced upstream of dehydrogenation unit 618 to produce a combined stream. The combined stream may enter dehydrogenation unit 618 to undergo dehydrogenation. In other embodiments, a paraffinic hydrocarbon stream is introduced directly into dehydrogenation unit 618 through one or more points of entry.

The olefinic hydrocarbon stream may be combined with first hydrocarbon stream in first conduit 610 of isomerization unit 514 via fifth conduit 622. The combined stream may enter isomerization unit 514 and at least a portion of the olefins present in the combined stream may be isomerized to branched olefins. In some embodiments, an olefinic hydrocarbon stream may exit dehydrogenation unit 618 and be directly introduced into isomerization unit 514 through one or more points of entry.

Figure 12:
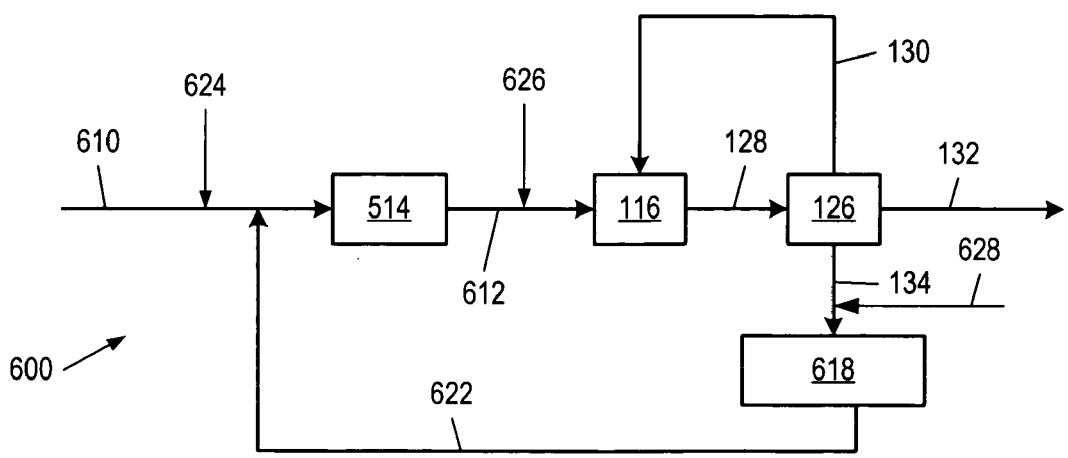
FIG. 12 depicts a schematic diagram of an embodiment of a system for producing branched aliphatic alcohols using an olefin isomerization unit with addition of an additional hydrocarbon stream.

In certain embodiments, additional hydrocarbon streams may be used control reaction conditions and/or optimize the concentration of paraffins and unreacted olefins in isomerization unit 514, hydroformylation unit 116 and/or other processing units used to produce aliphatic alcohols. Referring to FIG. 12, a first hydrocarbon stream may be introduced into isomerization unit 514 via first conduit 610. The first hydrocarbon stream may include olefins and paraffins. In certain embodiments, hydrocarbons in the first hydrocarbon stream may have an average carbon number from 7 to 18. In certain embodiments, hydrocarbons in the first hydrocarbon stream may have an average carbon number from 10 to 17. In some embodiments, an average carbon number of the hydrocarbons in a feed stream may range from 10 to 13. In other embodiments, an average carbon number of the hydrocarbons in a feed stream may range from 14 to 17. Olefins may, in some embodiments, be alpha-olefins. The alpha-olefin content of the first hydrocarbon stream may be greater than 70 percent of the total amount of olefins in the first hydrocarbon stream. In certain embodiments, a first hydrocarbon stream is derived from a Fischer-Tropsch process. In isomerization unit 514, at least a portion of the olefins in the first hydrocarbon stream may be isomerized to branched olefins to produce a second hydrocarbon stream. Conditions of the olefin isomerization may be controlled, as previously described for System 600, such that the number of carbon atoms in the olefin prior to and subsequent to the isomerization conditions is substantially the same.

At least a portion of a paraffinic hydrocarbon stream may be introduced into first conduit 610 via sixth conduit 624 upstream of isomerization unit 514 to produce a combined stream. The combined stream may enter isomerization unit 514 via first conduit 610. In other embodiments, a paraffinic hydrocarbon stream is introduced directly into isomerization unit 514 through one or more points of entry.

At least a portion of the olefins in the combined stream may be isomerized to branched olefins in isomerization unit 514 to produce a second hydrocarbon stream. Addition of the paraffinic hydrocarbon stream may be used to optimize the olefin concentration in isomerization unit 514 and to control the extent of branching in the produced olefins. Concentration of paraffins in the paraffinic hydrocarbon stream may be between about 10 percent and about 99 percent by weight. In certain embodiments, a paraffin concentration may range between about 10 percent and about 50 percent by weight. In some embodiments, a paraffin concentration may range between about 25 percent and about 75 percent by weight. In other embodiments, a paraffinic stream may include olefins. An olefin concentration in the hydrocarbon stream may be between 20 and 80 percent.

The second hydrocarbon stream may exit isomerization unit 514 and be introduced into hydroformylation unit 116 via second conduit 612. The second hydrocarbon stream may include branched olefins. At least a portion of a third hydrocarbon stream may be introduced into second conduit 612 via seventh conduit 626 upstream of hydroformylation unit 116 to form a mixed stream. The mixed stream may be then introduced into hydroformylation unit 116 via second conduit 612. At least a portion of the olefins in the mixed stream may be hydroformylated using process conditions as previously described for System 100. In some embodiments, a third hydrocarbon stream may be introduced directly into hydroformylation unit 116 through one or more points of entry. It should be understood that an olefin concentration in the process streams may be adjusted by adding a stream through sixth conduit 624 only, seventh conduit 626 only, directly into hydroformylation unit 116 only or by combinations thereof.

The third hydrocarbon stream in conduit 626 may be used to optimize the olefin concentration in hydroformylation unit 116 to maximize hydroformylation of the olefins. The third hydrocarbon stream may be from the same source as the first hydrocarbon stream. Alternatively, the third hydrocarbon stream may be a hydrocarbon stream that includes olefins, paraffins, and/or hydrocarbon solvents derived from another source.

The third hydrocarbon stream may include olefins and paraffins. In certain embodiments, an average carbon number of the hydrocarbons in the third hydrocarbon stream ranges from 7 to 18. In certain embodiments, a third hydrocarbon stream may include olefins and paraffins. In some embodiments, a paraffin content of the third hydrocarbon stream may be between about 60 percent and about 90 percent by weight. In other embodiments, a paraffin content of the third hydrocarbon stream may be greater than 90 percent by weight.

In an embodiment, an olefin content of a third hydrocarbon stream ranges between about 1 percent and about 99 percent relative to the total hydrocarbon content. In certain embodiments, an olefin content of the third hydrocarbon stream may be between about 45 percent and about 99 percent by weight. In other embodiments, an olefin concentration of the third hydrocarbon stream may be greater than 80 percent by weight.

In some embodiments, a third hydrocarbon stream may include linear olefins. Addition of a stream that includes linear olefins downstream from the isomerization unit allows the creation of a hydroformylation feed stream that includes a mixture of linear and branched olefins. By introducing a stream including branched and linear olefins into hydroformylation unit 116 a mixture of branched and linear aliphatic alcohol products may be obtained. Varying the amount of linear olefins added to the hydroformylation feed stream may control the ratio of linear to branched aliphatic alcohol products. A mixture of branched and linear aliphatic alcohols may have improved properties when converted to surfactants or other products. Examples of improved surfactant properties include, but are not limited to, low skin and eye irritation, foaming properties, biodegradability, cold-water solubility and cold-water detergency. Applications for these surfactants include, but are not limited to, personal care products, household and industrial laundry products, hand dishwashing products, machine lubricant additives and lubricating oil formulations.

The hydroformylation reaction mixture stream may enter separator 126 via third conduit 128. Separation of the aliphatic alcohol product from at least a portion of the hydroformylation reaction stream may be performed in separation unit 126. The separation may produce at least two streams, a bottom stream and a top stream using generally known techniques (e.g., distillation). At least a portion of the bottom stream may be recycled to hydroformylation unit 116 via recycle conduit 130. The top stream may be further purified and separated to produce at least two streams, a paraffins and unreacted olefins stream and a crude aliphatic alcohol product stream using techniques previously described for System 100. At least a portion of the crude aliphatic alcohol product stream may be further purified to produce an aliphatic alcohol product stream using generally known techniques. The aliphatic alcohol product stream may exit separation unit 126 and be transported via product conduit 132 to be stored on site, sold commercially, transported off-site, and/or utilized in other processing units. Produced aliphatic alcohols in the aliphatic alcohol product stream may have an average carbon number from 8 to 19. In certain embodiments, produced aliphatic alcohols in the aliphatic alcohol product stream may have an average carbon number from 11 to 18. In some embodiments, produced aliphatic alcohols in the aliphatic alcohol product stream may have an average carbon number from 11 to 14. In other embodiments, produced aliphatic alcohols in the aliphatic alcohol product stream may have an average carbon number from 15 to 18.

At least a portion of the paraffins and unreacted olefins stream may exit separation unit 126 and be transported via fourth conduit 134 to another processing unit, and/or storage vessel. At least a portion of the separated paraffins and unreacted olefins may enter dehydrogenation unit 620 via fourth conduit 134. An average carbon number of the hydrocarbons in the paraffins and unreacted olefins stream may range from 7 to 18. In certain embodiments, an average carbon number of the paraffins and unreacted olefins stream may range from 10 to 17. In some embodiments, an average carbon number of the paraffins and unreacted olefins stream may range from 10 to 13. In other embodiments, an average carbon number of the hydrocarbons in the paraffins and unreacted olefins stream may range from 14 to 17.

At least a portion of the paraffins in the hydrocarbon stream may be dehydrogenated using process conditions as previously described. At least a portion of the resulting olefinic hydrocarbon stream may exit dehydrogenation unit 618 and be transported to another processing unit and/or a storage vessel via fifth conduit 622.

At least a portion of a paraffinic hydrocarbon stream may be introduced into fourth conduit 134 via eighth conduit 628 upstream of dehydrogenation unit 618 to produce a combined stream. The combined stream may enter dehydrogenation unit 618 via fourth conduit 134. In other embodiments, a paraffinic hydrocarbon stream is introduced directly into dehydrogenation unit 618 through one or more points of entry.

In certain embodiments, at least a portion of non-converted paraffins may be separated from dehydrogenated compounds in the olefinic stream. Such separation may be accomplished by extraction, distillation or, adsorption techniques. At least a portion of the non-converted paraffins may be recycled to dehydrogenation unit 618 to undergo further dehydrogenation.

At least a portion of the olefinic hydrocarbon stream may exit dehydrogenation unit 618 via fifth conduit 622 and be combined with the first hydrocarbon stream in first conduit 610 upstream of isomerization unit 514 to produce a combined stream. The combined stream may be introduced into isomerization unit 514 via first conduit 610 and at least a portion of the olefins in the combined stream may be isomerized to branched olefins. In some embodiments, an olefinic hydrocarbon stream may be introduced directly into isomerization unit 514 via one or more points of entry. Alternatively, at least a portion of the olefinic hydrocarbon stream may be combined with a second hydrocarbon stream in second conduit 612 downstream of isomerization unit 514 to produce a mixed stream. Depending on the dehydrogenation conditions, the mixed stream may include linear olefins. Addition of the olefinic hydrocarbon stream with the second hydrocarbon stream may produce a mixed stream that includes both linear and branched olefins.

In certain embodiments, a first hydrocarbon stream may contain unwanted compounds (e.g., oxygenates and dienes) that may reduce catalyst selectivity in processes used to produce aliphatic alcohols. Removal of the unwanted compounds may be performed by hydrogenation of the first hydrocarbon stream. Hydrogenation of the first hydrocarbon stream, in certain embodiments, may produce a hydrocarbon stream that includes greater than 90 percent paraffins. The hydrogenated hydrocarbon stream may be dehydrogenated to produce an olefinic stream. The catalyst used in the dehydrogenation process may control the position of the olefin double bond. In certain embodiments, an olefinic hydrocarbon stream may include olefins in which greater than 70 percent of the olefins are alpha-olefins of a linear carbon skeletal structure. In other embodiments, an olefinic hydrocarbon stream may include olefins in which 50 percent or more of the olefin molecules present may be internal olefins.

Figure 13:
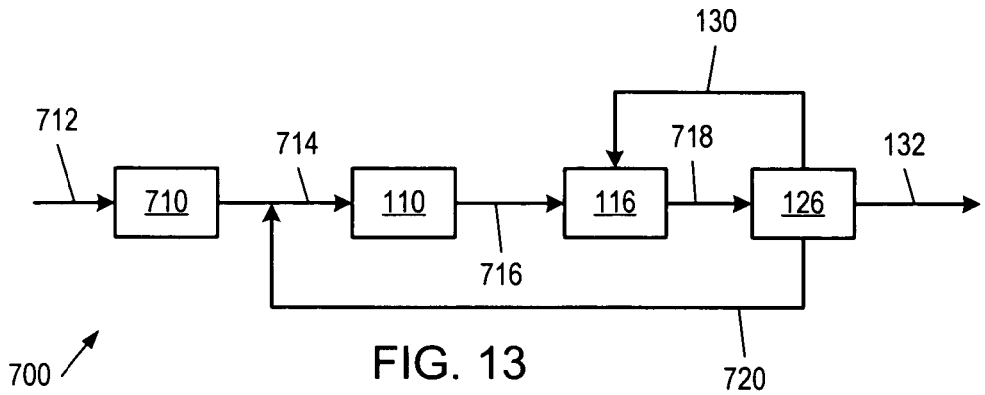
FIG. 13 depicts a schematic diagram of an embodiment of a system for producing aliphatic alcohols using a hydrogenation unit and a dehydrogenation-isomerization unit.

A first hydrocarbon stream may be introduced into hydrogenation unit 710 via first conduit 712 as depicted for System 700, in FIG. 13. Hydrocarbons in the first hydrocarbon stream may have an average carbon number from 7 to 18. In certain embodiments, hydrocarbons in the first hydrocarbon stream may have an average carbon number from 10 to 17. In some embodiments, hydrocarbons in the first hydrocarbon stream may have an average carbon number from 10 to 13. In other embodiments, an average carbon number of the hydrocarbons in a feed stream may range from 14 to 17. The first hydrocarbon stream includes olefins and paraffins. In hydrogenation unit 710, at least a portion of the olefins in the first hydrocarbon stream may be hydrogenated to paraffins to produce a second hydrocarbon stream.

Reaction conditions in hydrogenation unit 710 may be controlled to hydrogenate olefins and dienes and to remove oxygenates. An operating temperature of hydrogenation unit 710 may range between about 100° C. and about 300° C. In some embodiments, an operating temperature may range between about 150° C. and about 275° C. In other embodiments, an operating temperature may range between about 175° C. and 250° C. An operating pressure may range from about 5 atmospheres (506 kPa) to about 150 atmospheres (1520 kPa). In some embodiments, an operating pressure may range from 10 atmospheres psi (1013 kPa) to about 50 atmospheres (5065 kPa).

Hydrogenation processes may be carried out using any type of catalyst bed arrangement (e.g., fluidized bed, moving bed, slurry phase bed or a fixed bed). In certain embodiments, a fixed bed arrangement may be used. In a fixed bed system, hydrogen may be supplied to the hydrogenation stage at a gas hourly space velocity in the range from about 100 normal liter gas/liter catalyst/hour (NL/L/hr) to about 1000 NL/L/hr. In some embodiments, hydrogen may be supplied at a gas hourly space velocity in the range from about 250 NL/L/hr to 5000 NL/L/hr. "Gas space velocity as expressed in units of normal liter of gas/liter of catalyst/hour," as used herein, is the volume of a gas in liters at standard conditions of 0° C. and 760 mm Hg.

Hydrogenation catalysts are generally known and are commercially available in a large variety of compositions. In some embodiments, a hydrogenation catalyst may include one or more metals from Groups VIB and VII of the periodic Table of the Elements. In certain embodiments, metals may include, but are not limited to, molybdenum, tungsten, cobalt, nickel, ruthenium, iridium, osmium, platinum and palladium. The hydrogenation catalyst may include a refractory oxide or a silicate as a binder.

Hydrogenation reaction conditions and catalysts are described in European Patent No. 0 583 836 to Eilers et al., entitled "Process For The Preparation of Hydrocarbon Fuels;" European Patent No. 0 668 342 to Eilers et al., entitled "Lubricating Base Oil Preparation Process." Hydrogenation reaction conditions and catalysts are also described in U.S. Pat. No. 5,371,308 to Gosselink et al., entitled "Process For The Preparation Of Lower Olefins;" which is incorporated by reference herein.

At least a portion of the second hydrocarbon stream may enter dehydrogenation-isomerization unit 110 via second conduit 714. At least a portion of the paraffins in the second hydrocarbon stream may be dehydrogenated to olefins. At least a portion of the resulting olefins and at least a portion of the olefins that were already present in the feed stream may be isomerized to produce a second hydrocarbon stream. Process conditions used in dehydrogenation-isomerization unit 110 may be the same as previously described for Systems 100, 200 and 300. At least a portion of the resulting olefinic hydrocarbon stream and at least a portion of the unreacted hydrocarbons in the second hydrocarbon stream may form a third hydrocarbon stream.

In an embodiment, olefins may be separated, if desired, from the third hydrocarbon stream through techniques generally known in the art (e.g., distillation, molecular sieves, extraction, adsorption, adsorption/desorption, and/or membranes). Separation of at least a portion of the branched olefins from the linear olefins and paraffins may increase the concentration of branched olefins entering the hydroformylation unit. In addition, separation of at least a portion of the branched olefins from the linear olefins and paraffins may influence the ratio of linear to branched olefins produced in the hydroformylation unit.

Figure 14:
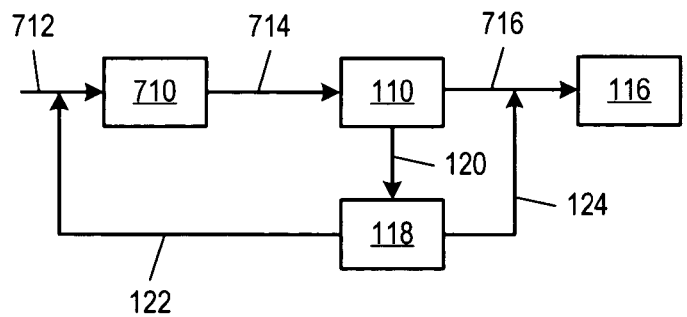
FIG. 14 depicts a schematic diagram of an embodiment of a system for producing branched aliphatic alcohols using a hydrogenation unit, a dehydrogenation-isomerization unit and a separation unit to separate branched olefins from linear olefins and paraffins.

Referring to FIG. 14, a third hydrocarbon stream may exit dehydrogenation-isomerization unit 110 and enter separation unit 118 via separation conduit 120. Separation unit 118 may produce at least two streams, a branched olefins stream and a linear olefins and paraffins stream. In separation unit 118, separation of branched olefins from linear olefins and paraffins may be performed using techniques described earlier for system 100.

At least a portion of the linear olefins and paraffins stream may be recycled transported to other processing units and/or stored on site. In an embodiment, at least a portion of the linear olefins and paraffins stream may be combined with first hydrocarbon stream in first conduit 712 via linear olefins and paraffins recycle conduit 122. The combined stream may enter hydrogenation unit 710 via first conduit 712 to continue the process to produce aliphatic alcohols. In some embodiments, the linear olefins and paraffins stream may be introduced directly into hydrogenation unit 710. In other embodiments, at least a portion of the linear olefins and paraffins stream may be combined with the second hydrocarbon stream upstream of the dehydrogenation-isomerization unit. The combined stream may enter the dehydrogenation-isomerization unit to continue the process to produce aliphatic alcohols. In some embodiments, a linear olefins and paraffins stream may be introduced directly into the dehydrogenation-isomerization unit.

At least a portion of the branched olefins stream may be transported and utilized in other processing streams and/or stored on site via branched olefins conduit 124. In some embodiments, at least a portion of a branched olefins stream may exit separation unit 118 and be introduced into third conduit 716 via branched olefins conduit 124. In other embodiments, at least a portion of a branched olefins stream may exit separation unit 118 and be introduced directly into a hydroformylation unit.

The third hydrocarbon stream may exit dehydrogenation-isomerization unit 110 and be introduced into hydroformylation unit 116 via third conduit 716. The third hydrocarbon stream may include branched olefins. An average carbon number of hydrocarbons in the third hydrocarbon stream may range from 7 to 18. In certain embodiments, hydrocarbons in a third hydrocarbon stream may have an average carbon number from 10 to 17. In some embodiments, hydrocarbons in the third hydrocarbon stream may have an average carbon number from 10 to 13. In other embodiments, an average carbon number of the hydrocarbons in a feed stream may range from 14 to 17. At least a portion of the olefins in the third hydrocarbon stream may be hydroformylated to produce aliphatic alcohols using process conditions as previously described for System 100.

In certain embodiments, it may be desirable to adjust the olefin and paraffin concentration entering hydroformylation unit 116 depending on the source of the olefin stream as previously described for System 100. An olefinic stream may be added to a process stream that contains less than 50 percent mono-olefins upstream of a hydroformylation unit to produce a process stream that is greater than 50 percent mono-olefins. In some embodiments, a process stream containing about 80 percent linear olefins and 20 percent paraffins may be added to a process stream containing primarily branched olefins upstream of a hydroformylation unit. Hydroformylation of olefins with the combined stream may result in a mixed stream containing branched and linear aliphatic alcohols.

In an embodiment, a fourth hydrocarbon stream may be added to a process stream upstream of the hydroformylation unit. The fourth hydrocarbon stream may have an olefin content that ranges between about 1 percent and about 99 percent relative to the total hydrocarbon content. In other embodiments, an olefin content of a fourth hydrocarbon stream may be greater than 80 percent relative to the total hydrocarbon content.

The hydroformylation reaction mixture stream may enter separator 126 via fourth conduit 718. Separation of at least a portion of paraffins and at least a portion of olefins from the hydroformylation reaction mixture may be accomplished as previously described for System 100. In separator 126 at least two streams, a bottom stream and a top stream, may be produced. The bottom stream may be recycled back to hydroformylation unit 116 via recycle conduit 130. The top stream may be purified and separated to produce at least two streams, a paraffins and unreacted olefins stream and a crude aliphatic alcohol product stream. Methods used for purification and separation, in certain embodiments, may be the same as those described for System 100. The crude aliphatic alcohol product stream may be further purified to form an aliphatic alcohol product stream. The aliphatic alcohol product stream may include branched aliphatic alcohols (e.g., branched primary alcohols). The aliphatic alcohol product stream may exit separator 126 via product conduit 132 to be stored on site, sold commercially, transported off-site, and/or utilized in other processing units (e.g., oxyalkylation, sulfation unit).

At least a portion of a paraffins and unreacted olefins stream may be combined with the second hydrocarbon stream in second conduit 714 upstream of dehydrogenation-isomerization unit 110 to produce a combined stream. The combined stream may be introduced into dehydrogenation-isomerization unit 110 and at least a portion of the paraffins in the combined stream may be dehydrogenated to olefins. The resulting olefins may be isomerized to branched olefins. In an embodiment, a paraffins and unreacted olefins stream may be introduced directly into dehydrogenation-isomerization unit 110.

In certain embodiments, at least a portion of a paraffins and unreacted olefins stream may be combined upstream of the hydrogenation unit to produce a combined stream. The combined stream may be introduced into the hydrogenation unit. At least a portion of the olefins and at least a portion of by-products from the hydroformylation reaction may be hydrogenated to paraffins. The resulting paraffins may be dehydrogenated and isomerized in the dehydrogenation-isomerization unit. In an embodiment, a paraffins and unreacted olefins stream may be introduced directly into the hydrogenation unit.

In certain embodiments, a first hydrocarbon stream may contain unwanted compounds (e.g., oxygenates and dienes) that may reduce catalyst selectivity in a dimerization process used to produce aliphatic alcohols. Removal of the unwanted compounds may be performed by hydrogenation of the first hydrocarbon stream. Hydrogenation of the first hydrocarbon stream, in certain embodiments, may produce a hydrocarbon stream that includes greater than 90 percent paraffins. The hydrogenated hydrocarbon stream may be dehydrogenated to produce an olefinic stream. The catalyst used in the dehydrogenation process may control the position of the olefin double bond. In certain embodiments, an olefinic hydrocarbon stream may include olefins in which greater than 70 percent of the olefins are alpha-olefins of a linear carbon skeletal structure. In other embodiments, an olefinic hydrocarbon stream may include olefins in which 50 percent or more of the olefin molecules present may be internal olefins.

Figure 15:
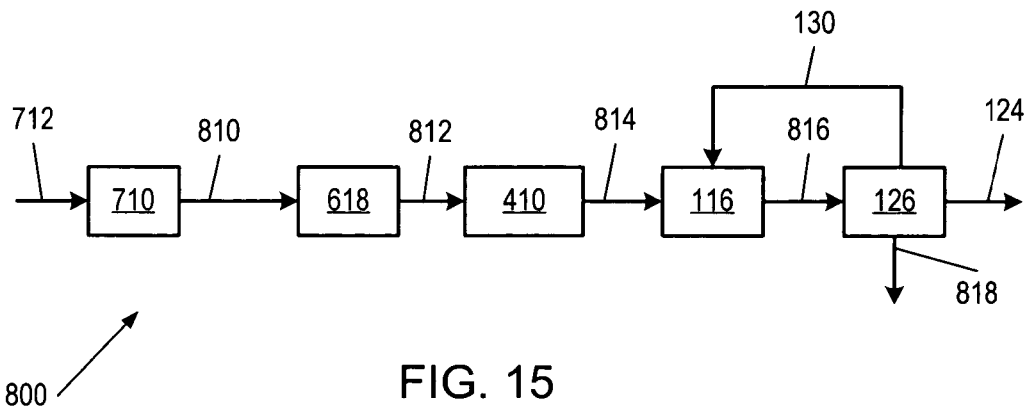
FIG. 15 depicts a schematic diagram of an embodiment of a system for producing aliphatic alcohols using a hydrogenation unit, a dehydrogenation unit and a dimerization unit.

Referring to System 800 as depicted in FIG. 15, a first hydrocarbon stream may be introduced into hydrogenation unit 710 via first conduit 712. The first hydrocarbon stream includes olefins and paraffins. Hydrocarbons in the first hydrocarbon stream may have an average carbon number from 4 to 9. In certain embodiments, hydrocarbons in a first hydrocarbon stream may have an average carbon number from 5 to 8. In some embodiments, hydrocarbons in a first hydrocarbon stream may have an average carbon number from 5 to 7. In other embodiments, hydrocarbons in a first hydrocarbon stream may have an average carbon number from 5 to 9. In hydrogenation unit 710, at least a portion of the olefins in the first hydrocarbon stream may be hydrogenated to paraffins to produce a second hydrocarbon stream. Reaction conditions in the hydrogenation unit 710, may be the same as previously described for System 700.

At least a portion of the second hydrocarbon stream may exit hydrogenation unit 710 and enter dehydrogenation unit 618 via second conduit 810. At least a portion of the unreacted paraffins in the second hydrocarbon stream may be dehydrogenated to produce an olefinic hydrocarbon stream by use of a catalyst selected from a wide range of catalyst types. For example, the catalyst may be based on a metal or metal compound deposited on a porous support. The metal or metal compound may be selected from, but is not limited to, chrome oxide, iron oxide and noble metals. Techniques of preparing catalysts, for performing the dehydrogenation step and for performing associated separation steps may be the same as described for Systems 500 and 600.

Reaction conditions in dehydrogenation unit 618 may be varied to control unwanted side products (e.g., coke, dienes, oligomers, cyclized hydrocarbons) and control double bond position in the olefin. In certain embodiments, temperatures may range from greater than 300° C. to less than 700° C. In other embodiments, a reaction temperature may range from about 450° C. to about 550° C. During the dehydrogenation reaction, the pressures in dehydrogenation unit 618 may range from greater 0.010 atmosphere (1 kPa) to about 25.0 atmospheres (2534 kPa). In an embodiment, a total pressure of dehydrogenation unit 618 during the reaction may range from about 0.010 atmosphere (1 kPa) to about 15.0 atmospheres (15200 kPa). In certain embodiments, pressure in dehydrogenation unit 618 may range from about 1.0 atmosphere (101 kPa) to about 5.0 atmospheres (510 kPa). In some embodiments, hydrogen may be fed into dehydrogenation unit 618 together with the paraffins and unreacted olefins stream in order to prevent coke from forming. The hydrogen to paraffins molar ratio may be set between about 0.1 moles of hydrogen to about 20 moles of paraffins. In some embodiments, hydrogen to paraffin molar ratio is about 1 to 10.

The amount of time (e.g., the residence time) that a process stream remains in dehydrogenation unit 618 may determine, to some extent, the amount of olefins produced. Generally, the longer a process stream remains in dehydrogenation unit 618, the conversion level of paraffins to olefins increases until an olefin-paraffin thermodynamic equilibrium is obtained. The residence time of the paraffins and unreacted olefins stream in dehydrogenation unit 618 may be selected such that the conversion level of paraffins to olefins may be kept below 50 mole percent. In certain embodiments, a conversion level of paraffins to olefins may be kept in the range from 5 to 30 mole percent. By keeping the conversion level low, side reactions may be prevented (e.g., diene formation and cyclization reactions).

In certain embodiments, at least a portion of non-converted paraffins may be separated from a third hydrocarbon stream using generally known techniques. Such separation may be accomplished by extraction, distillation or adsorption techniques. The paraffins may be recycled to dehydrogenation unit 618 to undergo dehydrogenation to continue the process to produce aliphatic alcohols.

At least a portion of the third hydrocarbon steam may exit the dehydrogenation unit 618 and enter dimerization unit 410 via third conduit 812. In dimerization unit 410, at least a portion of the olefins in the third hydrocarbon stream may be dimerized. The conditions of the olefin dimerization may be controlled, as previously described for System 400. The resulting dimerized olefins and the unreacted hydrocarbons in the third hydrocarbon stream may exit dimerization unit 410 as a fourth hydrocarbon stream.

Figure 16:
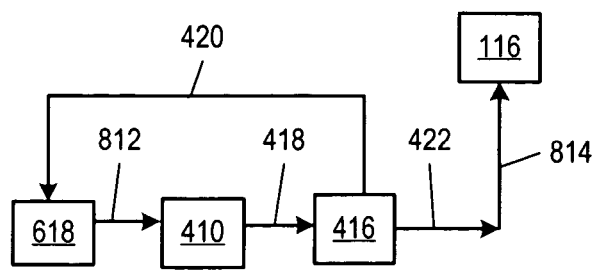
FIG. 16 depicts a schematic diagram of an embodiment of a separation unit to separate produced dimerized olefins from a reaction mixture.

In an embodiment, depicted in FIG. 16, a separation unit may be used to separate the produced dimerized olefins from the unreacted hydrocarbons in the fourth hydrocarbon stream. In an embodiment, at least a portion of fourth hydrocarbon stream may exit dimerization unit 410 and enter separation unit 416 via conduit 418. In separation unit 416 the reaction mixture may be separated into a produced dimerized olefins stream and a paraffins and unreacted olefins stream (e.g., by fractional distillation). The produced dimerized olefins stream may exit separation unit 416 and be introduced into fourth conduit 814 via conduit 422. The paraffins and unreacted olefins stream may contain hydrocarbons with a carbon number less than 8. At least a portion of the paraffins and unreacted olefins stream may be recycled into dehydrogenation unit 618 via conduit 420. In other embodiments, a paraffins and unreacted olefins stream may be combined with a process stream upstream of the dehydrogenation unit. In certain embodiments, a paraffins and unreacted olefins stream may be combined with a process stream upstream of the hydrogenation unit. In some embodiments, a paraffins and unreacted olefins stream may be recycled directly into the hydrogenation unit.

At least a portion of the fourth hydrocarbon stream may exit dimerization unit 410 and be introduced into hydroformylation unit 116 via fourth conduit 814. The fourth hydrocarbon stream includes branched olefins. At least a portion of the olefins in the fourth hydrocarbon stream may be hydroformylated to produce aliphatic alcohols using process conditions as previously described for System 100.

In certain embodiments, it may be desirable to adjust the olefin and paraffin concentration in hydroformylation unit 116 depending on the source of the olefin stream as previously described for System 100. An olefinic stream may be added to a process stream that contains less than 50 percent mono-olefins upstream of a hydroformylation unit to produce a process stream that is greater than 50 percent mono-olefins. In some embodiments, a fifth hydrocarbon stream containing about 80 percent linear olefins and 20 percent paraffins may be added to a process stream containing primarily branched olefins upstream of a hydroformylation unit. Hydroformylation of olefins in the combined stream may result in a mixed stream containing branched and linear aliphatic alcohols.

In an embodiment, a fifth hydrocarbon stream may be added to a process stream upstream of the hydroformylation unit. The olefin content of the fifth hydrocarbon stream may range between about 1 percent and about 99 percent relative to the total hydrocarbon content. In certain embodiments, an olefin content of a fifth hydrocarbon stream may be greater than 80 percent relative to the total hydrocarbon content.

The hydroformylation reaction mixture stream may enter separator 126 via fifth conduit 816. Separation of at least a portion the crude aliphatic alcohols from the hydroformylation reaction mixture may be accomplished as previously described for System 100. In separator 126, at least two streams, a bottom stream and a top stream, may be produced. The bottom stream may be recycled back to hydroformylation unit 116 via recycle conduit 130. The top stream may be purified and separated to produce at least two streams, a paraffins and unreacted olefins stream and a crude aliphatic alcohol product stream. Methods used for purification and separation, in certain embodiments, may be the same as those described for System 100. The crude aliphatic alcohol product stream may be further purified to form an aliphatic alcohol product stream. The aliphatic alcohol product stream may include branched aliphatic alcohols (e.g., branched primary alcohols). The aliphatic alcohol product stream may exit separator 126 via product conduit 132 to be stored on site, sold commercially, transported off-site, and/or utilized in other processing units (e.g., oxyalkylation unit and sulfation unit).

At least a portion of a paraffins and unreacted olefins stream may exit separator 126 and be recycled, combined with other process streams, sent to other processing units and/or be stored on site via sixth conduit 818. In certain embodiments, a paraffins and unreacted olefins stream may be further separated into a hydrocarbons stream including paraffins and unreacted olefins with a carbon number less than 8. The hydrocarbon stream including paraffins and unreacted olefins with a carbon number less than 8 may be introduced upstream of and/or into dehydrogenation unit 618. In other embodiments, a hydrocarbon stream including paraffins and unreacted olefins with a carbon number less than 8 may be introduced upstream of and/or into the hydrogenation unit.

Figure 17:
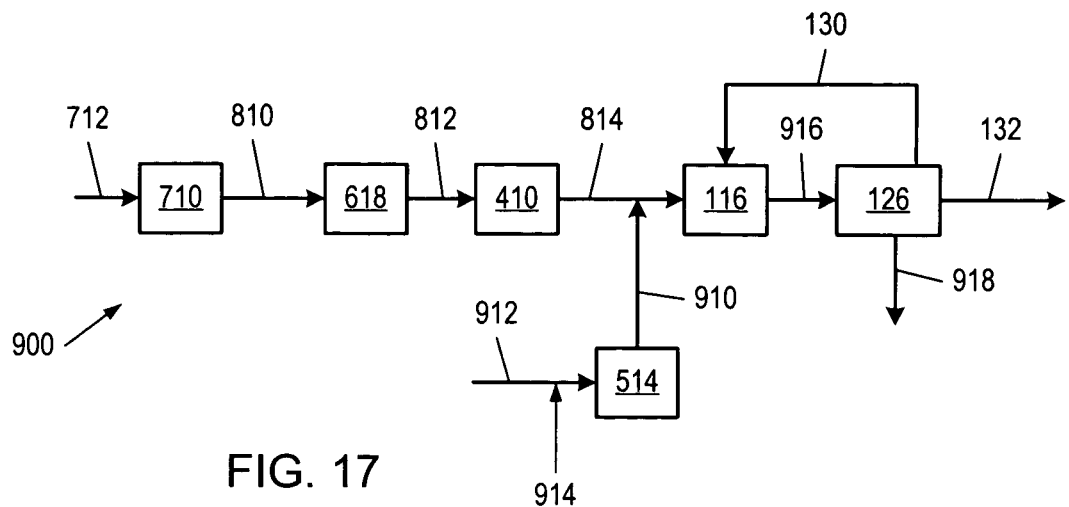
FIG. 17 depicts a schematic diagram of an embodiment of a system for producing aliphatic alcohols using a hydrogenation unit, a dehydrogenation unit, a dimerization unit and an isomerization unit.

In certain embodiments, a hydrocarbon stream from a dimerization unit may be combined with a hydrocarbon stream from an isomerization unit to produce a combined stream. The combined stream may be introduced into a hydroformylation unit. Combining streams from the two units may result in a more economically valuable process to produce branched aliphatic alcohols. Referring to System 900, as depicted in FIG. 17, a first hydrocarbon stream may be introduced into hydrogenation unit 710 via first conduit 712. The first hydrocarbon stream includes olefins and paraffins. In hydrogenation unit 710, at least a portion of the olefins in the first hydrocarbon stream may be hydrogenated to paraffins to produce a second hydrocarbon stream. Reaction conditions in the hydrogenation unit 710, may be the same as previously described for System 700.

At least a portion of the second hydrocarbon stream may enter dehydrogenation unit 618 via second conduit 810. At least a portion of the paraffins in the second hydrocarbon stream may be dehydrogenated using process conditions as previously described for Systems 300, 500, 600 and/or 800. At least a portion of the resulting olefinic hydrocarbon stream and at least a portion of the unreacted hydrocarbons in the second hydrocarbon stream may form a third hydrocarbon stream.

At least a portion of the third hydrocarbon steam may exit the dehydrogenation unit and enter dimerization unit 410 via third conduit 812. In dimerization unit 410, at least a portion of the olefins may be dimerized. At least a portion of the dimerized olefins exit dimerization unit 410 as a fourth hydrocarbon stream. The conditions of the olefin dimerization and isomerization may be controlled, as previously described for System 400.

At least a portion of the fourth hydrocarbon stream may exit dimerization unit 410 and enter hydroformylation unit 116 via fourth conduit 814. In certain embodiments, a fourth hydrocarbon stream may include olefins with an average carbon number that ranges from 8 to 16. At least a portion of a sixth hydrocarbon stream may be introduced into fourth conduit 814 via sixth conduit 910 upstream of hydroformylation unit 116 to produce a combined stream. The sixth hydrocarbon stream may be a stream exiting from isomerization unit 514. Isomerization unit 514 may be fed by a fifth hydrocarbon stream containing olefins and paraffins via a fifth conduit 912. In isomerization unit 514, at least a portion of the olefins in the fifth hydrocarbon stream may be isomerized to branched olefins to produce the sixth hydrocarbon stream using process conditions previously described for Systems 500 and 600. The sixth hydrocarbon stream may exit isomerization unit 514 via sixth conduit 910 and be combined with fourth hydrocarbon stream in conduit 814.

The combined stream may enter hydroformylation unit 116 and at least a portion of the olefins in the combined stream may be hydroformylated to produce aliphatic alcohols. In certain embodiments, a combined hydrocarbon stream may include hydrocarbons with an average carbon number ranging from 7 to 18. Hydroformylation reaction conditions and subsequent purification steps may be the same as previously described for System 100. The resulting alcohol products may be branched aliphatic alcohols with an average carbon number ranging from 8 to 19.

Figure 9:
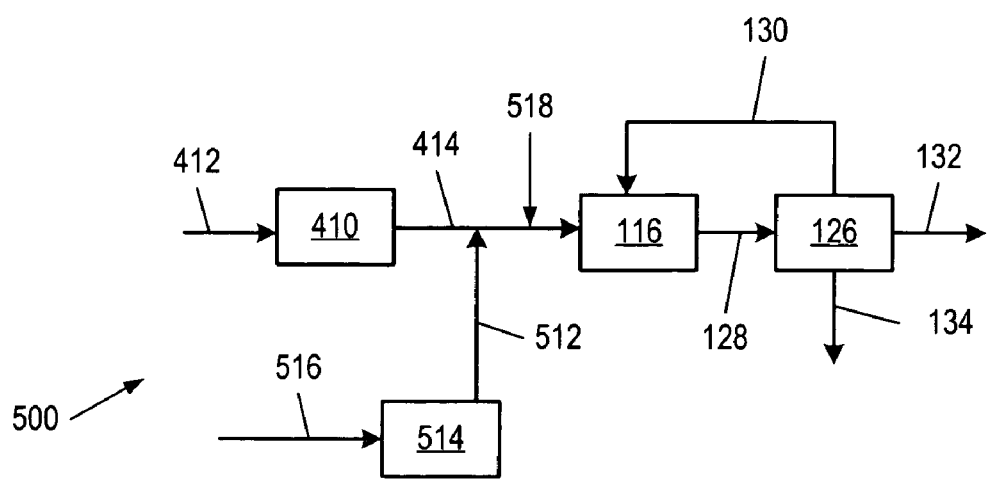
FIG. 9 depicts a schematic diagram of an embodiment of a system for producing branched aliphatic alcohols using a dimerization unit and an isomerization unit.

In certain embodiments, it may be desirable to adjust the olefin and paraffin concentration entering hydroformylation unit 116 and/or isomerization unit 514 depending on the source of the olefin stream as previously described for Systems 100, 500 and 600 in FIGS. 1, 9 and 12. A paraffinic stream containing less than 50 percent mono-olefins may be added to a process stream upstream of an isomerization unit to produce a process stream that is less than 50 percent mono-olefins. In some embodiments, a seventh hydrocarbon stream containing about 80 percent linear olefins and 20 percent paraffins may be added to a process stream containing primarily branched olefins upstream of a hydroformylation unit and/or isomerization unit. Subsequent hydroformylation of the olefins in the combined stream may result in a mixed stream containing branched and linear aliphatic alcohols. A paraffinic stream may be introduced upstream of isomerization unit via seventh conduit 914.

In an embodiment, a seventh hydrocarbon stream may be added to process stream upstream of the hydroformylation unit. The olefin content of a seventh hydrocarbon stream may range between about 1 percent and about 99 percent relative to the total hydrocarbon content. A paraffinic stream containing greater than 50 percent mono-olefins may be added to a process stream upstream of a hydroformylation unit to produce a process stream that is greater than 50 percent mono-olefins. In certain embodiments, an olefin content of a seventh hydrocarbon stream may be greater than 80 percent relative to the total hydrocarbon content.

The hydroformylation reaction mixture stream may enter separator 126 via eighth conduit 916. Separation of at least a portion of crude aliphatic alcohols from the hydroformylation reaction mixture may be accomplished as previously described for System 100. In separator 126 at least two streams, a bottom stream and a top stream, may be produced. The bottom stream may be recycled back to hydroformylation unit 116 via recycle conduit 130. The top stream may be purified and separated to produce at least two streams, a paraffins and unreacted olefins stream and a crude aliphatic alcohol product stream. Methods used for purification and separation, in certain embodiments, may be the same as those described for System 100. The crude aliphatic alcohol product stream may be further purified to form an aliphatic alcohol product stream. The aliphatic alcohol product stream may include branched aliphatic alcohols (e.g., branched primary alcohols). The aliphatic alcohol product stream may exit separator 126 via product conduit 132 to be stored on site, sold commercially, transported off-site, and/or utilized in other processing units (e.g., an oxyalkylation and/or a sulfation unit).

In certain embodiments, a paraffins and unreacted olefins stream may be introduced upstream of and/or into dehydrogenation unit 618 and/or hydrogenation unit 710 via other ports and/or conduits via ninth conduit 918. In other embodiments, a paraffins and unreacted olefins stream may be further separated into a hydrocarbons stream including paraffins and unreacted olefins with a carbon number less than 9. At least a portion of the paraffins and unreacted olefins stream may be introduced upstream of the dehydrogenation unit and/or the hydrogenation unit via other ports and/or conduits.

In certain embodiments, a first hydrocarbon stream may contain unwanted compounds (e.g., oxygenates and dienes) that may reduce catalyst selectivity in an isomerization process used to produce aliphatic alcohols. Removal of the unwanted compounds may be performed by hydrogenation of the first hydrocarbon stream. Hydrogenation of the first hydrocarbon stream, in certain embodiments, may produce a hydrocarbon stream that includes greater than 90 percent paraffins. The hydrogenated hydrocarbon stream may be dehydrogenated to produce an olefinic stream. The catalyst used in the dehydrogenation process may control the position of the olefin double bond. In certain embodiments, an olefinic hydrocarbon stream may include olefins in which greater than 70 percent of the olefins are alpha-olefins of a linear carbon skeletal structure. In other embodiments, an olefinic hydrocarbon stream may include olefins in which 50 percent or more of the olefin molecules present may be internal olefins.

Figure 18:
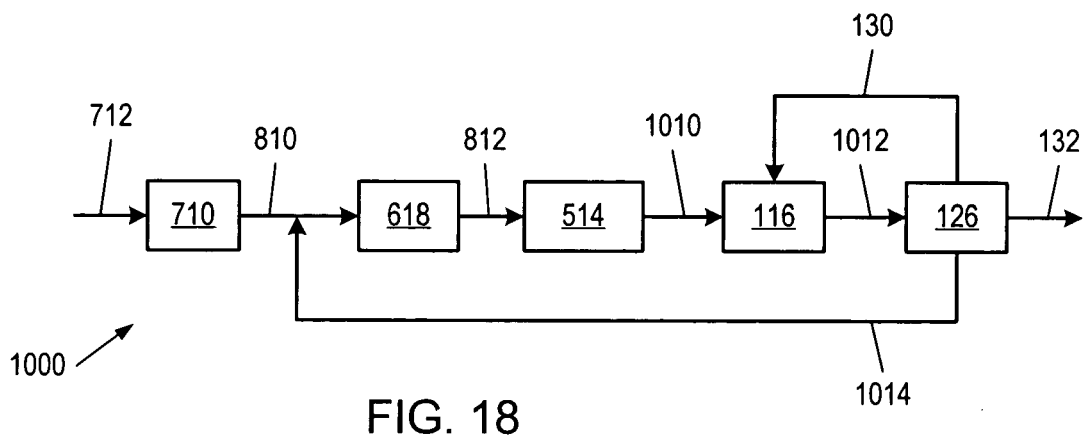
FIG. 18 depicts a schematic diagram of an embodiment of a system for producing aliphatic alcohols using a hydrogenation unit, a dehydrogenation unit and an isomerization unit.

Referring to System 1000 as depicted in FIG. 18, a first hydrocarbon stream may be introduced into hydrogenation unit 710 via first conduit 712. The first hydrocarbon stream includes olefins and paraffins. A first hydrocarbon stream may include hydrocarbons with an average carbon number from 7 to 18. In certain embodiments, a first hydrocarbon stream may include hydrocarbons with an average carbon number from 10 to 17. In some embodiments, a first hydrocarbon stream may include hydrocarbons with an average carbon number from 10 to 13. In other embodiments, a first hydrocarbon stream may include hydrocarbons with an average carbon number from 14 to 17. In hydrogenation unit 710, at least a portion of the olefins in the first hydrocarbon stream may be hydrogenated to paraffins to produce a second hydrocarbon stream. Reaction conditions in the hydrogenation unit 710, may be the same as previously described for System 700.

At least a portion of the second hydrocarbon stream may exit hydrogenation unit 710 and enter dehydrogenation unit 618 via second conduit 810. At least a portion of the paraffins in the second hydrocarbon stream may be dehydrogenated using process conditions as previously described for System 600.

At least a portion of the third hydrocarbon steam may exit the dehydrogenation unit 618 and enter isomerization unit 514 via third conduit 812. Conditions of the olefin isomerization may be controlled, as previously described in Systems 500 and 600, such that the number of carbon atoms in the olefin before and after isomerization is substantially the same. At least a portion of the olefins in the combined stream may be isomerized to branched olefins in isomerization unit 514 to produce a fourth hydrocarbon stream.

The fourth hydrocarbon stream may exit isomerization unit 514 and be introduced into hydroformylation unit 116 via fourth conduit 1010. The fourth hydrocarbon stream includes branched olefins. An average carbon number of hydrocarbons in the fourth hydrocarbon stream may range from 7 to 18. In certain embodiments, an average carbon number of hydrocarbons in the fourth hydrocarbon stream may range from 10 to 17. In some embodiments, an average carbon number of hydrocarbons in the fourth hydrocarbon stream may range from 10 to 13. In other embodiments, an average number of hydrocarbons in the fourth hydrocarbon stream may range from 14 to 17. At least a portion of the olefins may be hydroformylated using process conditions as previously described for System 600.

In certain embodiments, it may be desirable to adjust the olefin and paraffin concentration entering isomerization unit 514 and/or hydroformylation unit 116 depending on the source of the olefin stream as previously described for System 600. An olefinic stream may be added to a process stream that contains less than 50 percent mono-olefins upstream of an isomerization unit to produce a process stream that is less than 50 percent mono-olefins. In some embodiments, a fifth hydrocarbon stream containing about 20 percent linear olefins and 80 percent paraffins may be added to a process stream containing primarily branched olefins upstream of a hydroformylation unit. Subsequent hydroformylation of the olefins in the combined stream may result in a mixed stream containing branched and linear aliphatic alcohols.

In an embodiment, a fifth hydrocarbon stream may be added to process stream upstream of the hydroformylation unit and/or isomerization unit that contains an olefin content of between about 1 percent and about 99 percent relative to the total hydrocarbon content. An olefinic stream may be added to a process stream that contains greater than 50 percent mono-olefins upstream of a hydroformylation unit to produce a process stream that is greater than 50 percent mono-olefins. In other embodiments, an olefin content of a fifth hydrocarbon stream may be greater than 80 percent relative to the total hydrocarbon content.

In an embodiment, olefins may be separated, if desired, from the fourth hydrocarbon stream through techniques generally known in the art (e.g., distillation, molecular sieves, extraction, adsorption, adsorption/desorption and/or membranes). Separation of at least a portion of the branched olefins from the linear olefins and paraffins may increase the concentration of branched olefins entering the hydroformylation unit. In addition, separation of at least a portion of the branched olefins from the linear olefins and paraffins may influence the ratio of linear to branched olefins produced in the hydroformylation unit.

Figure 19:
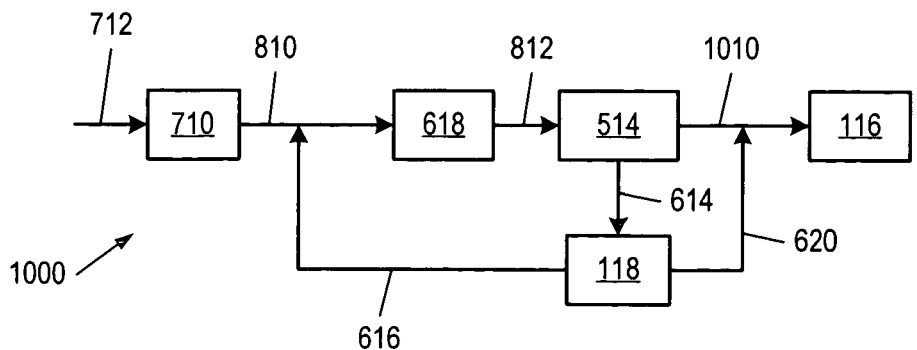
FIG. 19 depicts a schematic diagram of an embodiment of a system for producing branched aliphatic alcohols using a hydrogenation unit, a dehydrogenation-isomerization unit and a separation unit to separate branched olefins from linear olefins and paraffins.

Referring to FIG. 19, a fourth hydrocarbon stream may exit isomerization unit 514 and enter separation unit 118 via separation conduit 614. Separation unit 118 may produce at least two streams, a branched olefins stream and a linear olefins and paraffins stream. In separation unit 118, separation of branched olefins from linear olefins and paraffins using techniques described for System 100.

At least a portion of the linear olefins and paraffins stream may be recycled, transported to other processing units and/or stored on site. In an embodiment, at least a portion of the linear olefins and paraffins stream may be combined with first hydrocarbon stream in first conduit 712 via linear olefins and paraffins recycle conduit 616. The combined stream may enter hydrogenation unit 710 via first conduit 712 to continue the process to produce aliphatic alcohols. In some embodiments, the linear olefins and paraffins stream may be introduced directly into the hydrogenation unit. In other embodiments, at least a portion of the linear olefins and paraffins stream may be combined with the second hydrocarbon stream upstream of the dehydrogenation unit. The combined stream may enter the dehydrogenation unit to continue the process to produce aliphatic alcohols. In some embodiments, a linear olefins and paraffins stream may be introduced directly into the dehydrogenation unit.

At least a portion of the branched olefins stream may be transported and utilized in other processing streams and/or stored on site via branched olefins conduit 620. In some embodiments, at least a portion of a branched olefins stream may exit separation unit 118 and be combined with third hydrocarbon stream in fourth conduit 1010 upstream of hydroformylation unit 116 via branched olefins conduit 620. In other embodiments, at least a portion of a branched olefins stream may exit separation unit 118 and be introduced directly into the hydroformylation unit.

Referring to FIG. 18, the hydroformylation reaction mixture stream may enter separator 126 via fifth conduit 1012. Separation of at least a portion the crude aliphatic alcohols from the hydroformylation reaction mixture may be accomplished as previously described for System 100. In separator 126 at least two streams, a bottom stream and a top stream, may be produced. The bottom stream may be recycled back to hydroformylation unit 116 via recycle conduit 130. The top stream may be purified and separated to produce at least two streams, a paraffins and unreacted olefins stream and a crude aliphatic alcohol product stream. Methods used for purification and separation, in certain embodiments, may be the same as those described for System 100. The crude aliphatic alcohol product stream may be further purified to form an aliphatic alcohol product stream. The aliphatic alcohol product stream may include branched aliphatic alcohols (e.g., branched primary alcohols). The aliphatic alcohol product stream may exit separator 126 via product conduit 132 to be stored on site, sold commercially, transported off-site, and/or utilized in other processing units (e.g., an oxyalkylation and a sulfation unit).

At least a portion of a paraffins and unreacted olefins stream may exit separator 126 and be recycled, combined with other process streams, sent to other processing units and/or be stored on site via sixth conduit 1014. At least a portion of the paraffins and unreacted olefins stream may be combined with the second hydrocarbon stream in second conduit 810 upstream of dehydrogenation unit 618 via sixth conduit 1014 to produce a combined stream. The combined stream may be introduced into dehydrogenation unit 618 and at least a portion of the paraffins in the combined stream may be dehydrogenated to olefins. In an embodiment, a paraffins and unreacted olefins stream may be introduced directly into dehydrogenation unit 618. The concentration of the olefins in the olefinic hydrocarbon stream may be between 5 and 50 percent by weight. In certain embodiments, a concentration of the olefins may range between 10 and 20 percent by weight. Hydrocarbons in a paraffins and unreacted olefins stream may have an average carbon number from 10 to 18. An average carbon number of the hydrocarbons in a paraffins and unreacted olefins stream may range, in certain embodiments, from 10 to 17. In some embodiments, hydrocarbons in a paraffins and unreacted olefins stream may range from 10 to 13. In other embodiments, an average carbon number of the hydrocarbons in a paraffins an unreacted olefins stream may range from 14 to 17. In some embodiments, a paraffins and unreacted olefins stream may be introduced directly into and/or upstream of the hydrogenation unit.

Aliphatic alcohols may be converted to oxy alcohols, sulfates or other commercial products. At least a portion of the aliphatic alcohols in the alcohol product stream may be reacted in an oxyalkylation unit with an epoxide (e.g., ethylene oxide, propylene oxide, butylene oxide) in the presence of a base to produce an oxyalkyl alcohol. Condensation of an alcohol with an epoxide allows the alcohol functionality to be expanded by one or more oxy groups. The number of oxy groups may range from 3 to 12. For example, reaction of an alcohol with ethylene oxide may produce alcohol products having between 3 to 12 ethoxy groups. Reaction of an alcohol with ethylene oxide and propylene oxide may produce alcohols with an ethoxy/propoxy ratio of ethoxy to propoxy groups from about 4:1 to about 12:1. In some embodiments, a substantial proportion of alcohol moieties may become combined with more than three ethylene oxide moieties. In other embodiments, an approximately equal proportion may be combined with less than three ethylene oxide moieties. In a typical oxyalkylation product mixture, a minor proportion of unreacted alcohol may be present in the product mixture. In an embodiment, at least a portion of the aliphatic alcohol product stream may be formed by condensing a $C_5$ to $C_{31}$ aliphatic alcohol with an epoxide. In certain embodiments, a $C_5$ to $C_{15}$ branched primary alcohol may be condensed with ethylene oxide and/or propylene oxide. In other embodiments, a $C_{11}$ to $C_{17}$ branched primary alcohol may be condensed with ethylene oxide and/or propylene oxide. The resulting oxyalkyl alcohols may be sold commercially, transported off-site, stored on site and/or used in other processing units. In some embodiments, an oxyalkyl alcohol may be sulfated to form an anionic surfactant.

In an embodiment, at least a portion of the alcohols in the aliphatic alcohol product stream may be added to a base. The base may be an alkali metal or alkaline earth metal hydroxide (e.g., sodium hydroxide or potassium hydroxide). The base may act as a catalyst for the oxyalkylation reaction. An amount from about 0.1 percent by weight to about 0.6 percent by weight of a base, based on the total weight of alcohol, may be used for oxyalkylation of an alcohol. In an embodiment, a weight percent of a base may range from about 0.1 percent by weight to 0.4 percent by weight based on the total alcohol amount. The reaction of the alcohol with the base may result in formation of an alkoxide. The resulting alkoxide may be dried to remove any water present. The dried alkoxide may be reacted with an epoxide. An amount of epoxide used may be from about 1 mole to about 12 moles of epoxide per mole of alkoxide. A resulting alkoxide-epoxide mixture may be allowed to react until the epoxide is consumed. A decrease in overall reaction pressure may indicate that the reaction is complete.

Reaction temperatures in an oxyalkylation unit may range from about 120° C. to about 220° C. In an embodiment, reaction temperatures may range from about 140° C. to about 160° C. Reaction pressures may be achieved by introducing to the reaction vessel the required amount of epoxide. Epoxides have a high vapor pressure at the desired reaction temperature. For consideration of process safety, the partial pressure of the epoxide reactant may be limited, for example, to less than 4 atmospheres (413 kPa). Other safety measures may include diluting the reactant with an inert gas such as nitrogen. For example, inert gas dilution may result in a vapor phase concentration of reactant of about 50 percent or less. In some embodiments, an alcohol-epoxide reaction may be safely accomplished at a greater epoxide concentration, a greater total pressure and a greater partial pressure of epoxide if suitable, generally known, safety precautions are taken to manage the risks of explosion. With respect to ethylene oxide, a total pressure from about 3 atmospheres (304 kPa) to about 7 atmospheres (709 kPa) may be used. Total pressures of ethylene oxide from about 1 atmosphere (101 kPa) to about 4 atmospheres (415 kPa) may be used in certain embodiments. In an embodiment, total pressures from about 1.5 atmospheres (150 kPa) to about 3 atmospheres (304 kPa) with respect to ethylene oxide may be used. The pressure may serve as a measure of the degree of the reaction. The reaction may be considered substantially complete when the pressure no longer decreases with time.

Aliphatic alcohols and oxyalkyl alcohols may be derivatized to form compositions (e.g., sulfonates, sulfates, phosphates) useful in commercial product formulations (e.g., detergents, surfactants, oil additives, lubricating oil formulations). For example, alcohols may be sulfurized with $SO_3$ to produce sulfates. The term "sulfurized" refers to a sulfur atom or sulfur containing functionality being added to a carbon or oxygen. Sulfurization processes are described in U.S. Pat. No. 6,462,215 to Jacobson et al., entitled "Sulfonation, Sulfation and Sulfamation"; U.S. Pat. No. 6,448,435 to Jacobson et al., entitled "Sulfonation, Sulfation and Sulfamation"; U.S. Pat. No. 3,462,525 to Levinsky et al, entitled, "Dental Compositions Comprising Long-Chain Olefin Sulfonates;" U.S. Pat. No. 3,428,654 to Rubinfeld et al., entitled, "Alkene Sulfonation Process and Products;" U.S. Pat. No. 3,420,875 to DiSalvo et al., entitled, "Olefin Sulfonates;" U.S. Pat. No. 3,506,580 to Rubinfeld et al., entitled, "Heat-Treatment Of Sulfonated Olefin Products;" and U.S. Pat. No. 3,579,537 to Rubinfeld, entitled, "Process For Separation Of Sultones From Alkenyl Sulfonic Acids," all of which are incorporated herein by reference.

A general class of aliphatic alcohol sulfates may be characterized by the chemical formula: $(R—O-(A)_x-SO_3)_nM$. R' represents the aliphatic moiety. "A" represents a moiety of an alkylene oxide; x represents the average number of A moieties per R—O moiety and may range from 0 to 15; and n is a number depending on the valence of cation M. Examples of cation M include, but are not limited to, alkali metal ions, alkaline earth metal ions, ammonium ions and/or mixtures thereof. Examples of cations include, but are not limited to, magnesium, potassium, monoethanol amine, diethanol amine or triethanol amine.

Aliphatic and oxyalkyl alcohols may be sulfated in a sulfation unit. Sulfation procedures may include the reaction of sulfur trioxide ($SO_3$), chlorosulfonic acid ($ClSO_3H$), sulfamic acid ($NH_2SO_3H$) or sulfuric acid with an alcohol. In an embodiment, sulfur trioxide in concentrated (e.g., fuming) sulfuric acid may be used to sulfate alcohols. The concentrated sulfuric acid may have a concentration of about 75 percent by weight to about 100 percent by weight in water. In an embodiment, concentrated sulfuric acid may have a concentration of about 85 percent by weight to about 98 percent by weight in water. The amount of sulfur trioxide may range from about 0.3 mole to about 1.3 moles of sulfur trioxide per mole of alcohol. In certain embodiments, an amount of sulfur trioxide may range from about 0.4 moles to about 1.0 moles of sulfur trioxide per mole of alcohol.

In an embodiment, a sulfur trioxide sulfation procedure may include contacting a liquid alcohol or an oxyalkyl alcohol and gaseous sulfur trioxide in a falling film sulfator to produce a sulfuric acid ester of the alcohol. The reaction zone of the falling film sulfator may be operated at about atmospheric pressure and at a temperature in the range from about 25° C. to about 70° C. The sulfuric acid ester of the alcohol may exit the failing film sulfator and enter a neutralization reactor. The sulfuric acid ester may be neutralized with an alkali metal solution to form the alkyl sulfate salt or the oxyalkyl sulfate salt. Examples of an alkali metal solution may include solutions of sodium or potassium hydroxide.

The derivatized alcohols may be used in a wide variety of applications. An example of an application includes detergent formulations. Detergent formulations include, but are not limited to, granular laundry detergent formulation, liquid laundry detergent formulations, liquid dishwashing detergent formulations and miscellaneous formulations. Examples of miscellaneous formulations may include general purpose cleaning agents, liquid soaps, shampoos and liquid scouring agents.

Granular laundry detergent formulations may include a number of components besides the derivatized alcohols (e.g., surfactants, builders, co-builders, bleaching agents, bleaching agent activators, foam controlling agents, enzymes, anti-graying agents, optical brighteners and stabilizers). Examples of other surfactants may include ionic, nonionic, amphoteric or cationic surfactants.

Liquid laundry detergent formulations may include the same components as granular laundry detergent formulations. In certain embodiments, liquid laundry detergent formulations may include less of an inorganic builder component than granular laundry detergent formulations. Hydrotropes may be present in the liquid detergent formulations. General purpose cleaning agents may include other surfactants, builders, foam control agents, hydrotropes and solubilizer alcohols.

The present formulations may include a large amount of the builder and co-builder components. In some embodiments, builder and co-builder components may be about 90 percent by weight. To intensify the cleaning action, the builder and co-builder components may, in other embodiments, be in amounts from about 5 percent to about 35 percent by weight, based on the weight of the formulation. Examples of common inorganic builders may include phosphates, polyphosphates, alkali metal carbonates, silicates and sulfonates. Examples of organic builders may include polycarboxylates, aminocarboxylates such as ethylenediaminetetraacetates, nitrilotriacetates, hydroxycarboxylates, citrates, succinates, and substituted and unsubstituted alkane di- and polycarboxylic acids. Another type of builder, useful in granular laundry and built liquid laundry agents, includes various substantially water-insoluble materials, which are capable of reducing the water hardness. An example of process to reduce water hardness is an ion exchange process. In an embodiment, complex sodium aluminosilicates, known as type A zeolites, may be useful for this purpose.

The present formulations may include percompounds with a bleaching action. Examples of percompounds may include perborates, percarbonates, persulfonates and organic peroxy acids. Formulations containing percompounds may also include stabilizing agents. Examples of stabilizing agents may include magnesium silicate, sodium ethylenediaminetetraacetate or sodium salts of phosphonic acids. In some embodiments, bleach activators may be used to increase the efficiency of the inorganic persalts at lower washing temperatures. Substituted carboxylic acid amides, tetraacetylethylenediamine, substituted carboxylic acids may be useful for lower washing temperatures in other embodiments. Examples of substitute carboxylic acids may include isononyloxybenzenesulfonate and sodium cyanamide.

Examples of suitable hydrotropic substance include, but are not limited to, alkali metal salts of benzene, toluene and xylenes, sulfonic acids; alkali metal salts of formic acid; citric and succinic acid; alkali metal chlorides; urea; and mono-, di- and tri-ethanolamine. Examples of solubilizer alcohols may include ethanol, isopropanol, mono- or polyethylene glycols, monopropylene glycol and ether alcohols.

Examples of foam control agents may include high molecular weight fatty acid soaps, paraffinic hydrocarbons and silicon containing defoamers. In an embodiment, hydrophobic silica particles are efficient foam control agents in laundry detergent formulations.

Examples of known enzymes that are effective in the laundry detergent formulations may include protease, amylase and lipase. Enzymes, which have an optimum performance at the design conditions of the washing and cleaning agent, may be used.

A large number of fluorescent whiteners are described in the literature. For the laundry washing formulations, the derivatives of diaminostilbene, disulfonates and substituted distyrybiphenyl may be used.

Water-soluble colloids of an organic nature may be used as anti-graying agents. Examples of water-soluble antigraying agents may include polyanionic polymers such as polymers and copolymers of acrylic and maleic acid, cellulose derivatives such as carboxymethyl cellulose methyl- and hydroxyethylcellulose.

The formulations may typically include one or more inert components. For example, the balance of liquid detergent formulations may typically be an inert solvent or diluent (e.g., water). Powdered or granular detergent formulations typically contain quantities of inert filler or carrier materials.

EXAMPLES

Example 1

Isomerization of Olefins in a Fischer-Tropsch Derived Hydrocarbon Stream

Carbon monoxide and hydrogen were reacted under Fischer-Tropsch process conditions to yield a hydrocarbon mixture of linear paraffins, linear olefins, a minor amount of dienes and a minor amount of oxygenates. The Fischer-Tropsch hydrocarbon stream was separated into different hydrocarbon streams using fractional distillation techniques. A hydrocarbon stream containing olefins and paraffins with an average number of carbon atoms from 8 to 10 was obtained. The composition of the resulting $C_8$-$C_{10}$ hydrocarbon stream was analysed by gas chromatography and is tabulated in Table 1.

TABLE 1

| Fischer-Tropsch Hydrocarbon Stream Composition | Wt. % |
|---|---|
| $C_7$ and lighter hydrocarbons | 0.12 |
| $C_8$ branched olefins | 0.02 |
| $C_8$ linear olefins | 0.75 |
| 1-Octene | 0.69 |
| n-Octane | 2.21 |
| $C_9$ branched olefins | 0.16 |
| $C_9$ linear olefins | 8.52 |
| 1-Nonene | 8.07 |
| n-Nonane | 20.03 |
| $C_{10}$ branched olefins | 0.28 |
| $C_{10}$ linear olefins | 22.92 |
| 1-Decene | 20.87 |
| n-Decane | 41.12 |
| $C_{11}$ and heavier hydrocarbons | 0.21 |
| $C_9$-$C_{11}$ alcohols | 3.56 |

A zeolite catalyst used for isomerization of linear olefins in the hydrocarbon stream was prepared in the following manner. Ammonium-ferrierite (645 grams) exhibiting a 5.4% loss on ignition and exhibiting the following properties: molar silica to alumina ratio of 62:1, surface area of 369 square meters per gram (P/Po=0.03), soda content of 480 ppm and n-hexane sorption capacity of 7.3 g per 100 g of ammonium-ferrierite was loaded into a Lancaster mix muller. CATAPAL® D alumina (91 grams) exhibiting a loss on ignition of 25.7% was added to the muller. During a five-minute mulling period, 152 milliliters of deionized water was added to the alumina/ammonium-ferrierite mixture. Next, a mixture of 6.8 grams glacial acetic acid, 7.0 grams of citric acid and 152 milliliters of deionized water was slowly added to the alumina/ammonium-ferrierite mixture in the muller to peptize the alumina. The resulting alumina/ammonium-ferrierite/acid mixture was mulled for 10 minutes. Over a period of 15 minutes, a mixture of 0.20 grams of tetraamine palladium nitrate in 153 grams of deionized water was slowly added to mulled alumina/ammonium-ferrierite/acid mixture. The resulting mixture exhibited a 90:10 ratio of zeolite to alumina and a loss on ignition of 43.5%. The zeolite/alumina mixture was shaped by extruding the mixture through a stainless steel die plate (1/16" holes) of a 2.25 inch Bonnot extruder.

The moist zeolite/alumina extrudate was dried at 125° C. for 16 hours. After drying, the zeolite/alumina extrudate was longsbroken manually. The zeolite/alumina extrudate was calcined in flowing air at 200° C. for two hours. The temperature was raised to a maximum temperature of 500° C. and the zeolite/alumina extrudate was calcined for an additional two hours to yield an isomerization catalyst. The isomerization catalyst was allowed to cool in a dessicator under a nitrogen atmosphere.

Stainless steel tubing, 1 inch OD, 0.6 inch ID and 26 inches long, was used as an isomerization reactor. A thermowell extended 20 inches from the top of the stainless steel reactor tube. To load the reactor tube, the reactor tube was inverted and a piece of glass wool was transferred down the wall of the reactor tube, over the thermowell and positioned at the bottom of the reactor tube to serve as a plug for the reactor tube. Silicon carbide (20 mesh) was added to a depth of about 6 inches to the reactor tube. A second piece of glass wool was placed over the silicon carbide. A mixture of 6.0 grams of the isomerization catalyst particles (6-20 mesh) and 45 grams of fresh silicon carbide (60-80 mesh) was added to the reactor tube in two parts. The two-part addition distributed the isomerization catalyst evenly in the reactor tube and resulted in an isomerization catalyst bed of about 10 inches in length. A third piece of glass wool was added to the top of the catalyst in the reactor tube. Silicon carbide (20 mesh) was layered onto the third piece of glass wool. A fourth piece of glass wool was positioned over the silicon carbide to serve as a plug for the bottom of the reactor tube. To monitor the temperature of the reaction at various points in the reactor tube, a multipoint thermocouple was inserted into the thermowell of the reactor tube. The temperature above, below and at three different places in the catalyst bed was monitored. The reactor tube was inverted and installed in the furnace. The reactor tube was heated to the operating temperature of 280° C. over a four-hour period under flowing nitrogen. Once the temperature of 280° C. was obtained, the reactor tube was held at the operating temperature for an additional two hours to condition the isomerization catalyst.

After conditioning the isomerization catalyst, the hydrocarbon stream was pumped through the reactor tube at a flow rate of 60 g/hr. Nitrogen, at a flow rate of 6 L/hr, was passed over the isomerization catalyst simultaneously with the hydrocarbon stream. The hydrocarbon stream was vaporized before contacting the isomerization catalyst. The reactor tube was operated at an outlet pressure of 20 kPa above atmospheric pressure.

In Table 2, the weight percent of $C_8$-$C_{10}$ branched olefins, $C_8$-$C_{10}$ linear olefins and $C_8$-$C_{10}$ paraffins in the hydrocarbon stream at 0 hours and in the reactor tube effluent after 24 and 48 hours of isomerization is tabulated. Greater than 90% of the linear olefins in the hydrocarbon stream were converted into branched olefins in the isomerization reactor. During the isomerization step, a small amount of material boiling below $C_8$ was generated from cracking side reactions. In addition, a portion of the $C_9$-$C_{11}$ alcohols present in the feed was dehydrated to yield additional olefins in the product. The average number of alkyl branches on the $C_8$-$C_{10}$ olefins in the product was found to be 1.0 as determined by $^1$H NMR analysis.

TABLE 2

| Fischer-Tropsch Hydrocarbon Stream Composition During Isomerization Reaction | 0 Hr Wt. % | 24 Hr Wt. % | 48 Hr Wt. % |
|---|---|---|---|
| $C_8$-$C_{10}$ branched olefins | 0.46 | 33.04 | 33.16 |
| $C_8$-$C_{10}$ linear olefins | 32.19 | 2.52 | 2.54 |
| $C_8$-$C_{10}$ paraffins | 63.19 | 63.32 | 63.27 |
| Branched to linear $C_8$-$_{10}$ olefin ratio | 0.1 | 13.1 | 13.1 |

Example 2

Isomerization of 1-Dodecene 1-dodecene was obtained from Shell Chemical Co. The composition of 1-dodecene, as assayed by gas chromatography, is tabulated in Table 3.

TABLE 3

| 1-Dodecene Composition | Wt. % |
|---|---|
| 1-Dodecene | 98.0 |
| Other $C_{10}$-$C_{14}$ olefins | 1.2 |
| <$C_{10}$ hydrocarbons | 0.2 |
| >$C_{14}$ hydrocarbons | 0.2 |
| Paraffins | 0.4 |
| Total $C_{10}$-$C_{14}$ hydrocarbons | 99.6 |

1-dodecene was isomerized using the same reactor tube design and isomerization catalyst preparation as described in Example 1. A stream of 1-dodecene was pumped through a reactor tube at a flow rate of 90 g/hr. Nitrogen, at a flow rate of 6 L/hr, was passed over the isomerization catalyst simultaneously with the stream of 1-dodecene. The stream of 1-dodecene was vaporised before contacting the isomerization catalyst. The reactor tube was operated at an outlet pressure of 20 kPa above atmospheric pressure and a temperature of 290° C.

Table 4 is a tabulation of the weight percent of less than $C_{10}$, $C_{10}$-$C_{14}$ and greater than $C_{14}$ molecules in 1-dodecene at 0 hours and the reactor tube effluent after 168 and 849 hours. Linear $C_{10}$-$C_{14}$ olefins were converted in a 94% yield to branched $C_{10}$-$C_{14}$ olefins after a 168 hr processing time. During the isomerization step, less than 3 weight percent of material boiling below $C_{10}$ was generated from cracking side reactions. The average number of alkyl branches on the $C_{10}$-$C_{14}$ olefins in the product was determined to be 1.3 by $^1$H NMR analysis.

TABLE 4

| 1-Dodecene Stream Composition During Isomerization Reaction | 0 Hr Wt. % | 168 Hr Wt. % | 849 Hr Wt. % |
|---|---|---|---|
| <$C_{10}$ hydrocarbons | 0.2 | 2.5 | 2.4 |
| $C_{10}$-$C_{14}$ hydrocarbons | 99.6 | 97.2 | 97.4 |
| >$C_{14}$ hydrocarbons | 0.2 | 0.3 | 0.2 |
| Branched $C_{10}$-$C_{14}$ olefins | 0.6 | 93.2 | 93.4 |
| Linear $C_{10}$-$C_{14}$ olefins | 99.0 | 2.8 | 2.9 |
| Paraffins | 1.0 | 2.0 | 1.9 |

Example 3

Dehydrogenation of Dodecane with Minimal Isomerization

Dodecane was obtained from Aldrich Chemical Company and stored under nitrogen before being processed. The composition of dodecane, as assayed by gas chromatography, is tabulated in Table 5.

TABLE 5

| Dodecane Composition | Wt. % |
|---|---|
| Dodecane | 99.3 |
| <$C_{10}$ hydrocarbons | <0.1 |
| $C_{10}$, $C_{11}$, $C_{13}$ and $C_{14}$ hydrocarbons | <0.6 |
| >$C_{14}$ hydrocarbons | <0.1 |
| Other $C_{10}$-$C_{14}$ olefins | <0.1 |

A paraffin dehydrogenation catalyst was prepared according to Example 1 (catalyst A) of U.S. Pat. No. 4,430,517 to Imai et al., entitled "Dehydrogenation Process Using A Catalytic Composition", which is incorporated by reference herein. The resulting catalyst included 0.8 wt. % platinum, 0.5 wt. % tin, 2.7 wt. % tin, 2.7 wt. % potassium and 1.3 wt. % chlorine on a gamma-alumina support. The atomic ratio of potassium to platinum for this catalyst was 16.8.

The dehydrogenation catalyst was prepared by dissolving substantially pure aluminum pellets in a hydrochloric acid solution. An amount of stannic chloride was added to the resulting solution to provide a final composite containing 0.5 weight % tin and stirred to distribute the tin component evenly throughout the mixture. Hexamethylenetetramine was added to the resulting tin mixture and the resulting tin-amine mixture was dropped into an oil bath in a manner to form spherical particles having an average particle diameter of about 1/16 inch. The spheres were aged, washed with an ammoniacal solution, dried and calcined to form a spherical gamma-alumina carrier material. The resulting spheres contained about 0.5 weight % tin in the form of tin oxide. More details about the method of preparing the alumina carrier material are disclosed in U.S. Pat. No. 2,620,314 to Hoesktra, entitled, "Spheroidal Alumina," which is incorporated by reference herein.

The tin-alumina composite was contacted with a deionized solution of chloroplatinic acid and hydrochloric acid (2 weight percent based on alumina weight) in a rotary drier for 15 minutes at room temperature. The amount of chloroplatinic acid used was the amount necessary to incorporate 0.8 weight percent platinum into the tin-alumina composite. The solution was then heated and purged with nitrogen to remove water resulting in a platinum-chlorine-tin-alumina composite. The incorporated chlorine was removed by heating the platinum-chlorine-tin-alumina composite to 550° C. and treating the composite with a 50/50 air/80° C. steam mixture at a gas hourly space velocity (GHSV) of 300 hr$^{-1}$. After treatment with the air/steam mixture, the platinum-tin-alumina composite contained less than 0.1 weight percent chlorine.

The platinum-tin-alumina composite was contacted with a deionized water solution of potassium nitrate. The amount of potassium nitrate used was the amount necessary to incorporate 2.7 weight percent of potassium in the platinum-tin-alumina composite. The water was removed from the platinum-tin-potassium-alumina composite by heating the composite to 100° C. under a purge of dry air (1000 hr$^{-1}$ GHSV) for 0.5 hour. The temperature was raised to 525° C.

and the platinum-tin-potassium alumina composite was treated with a stream of hydrochloric acid (12 cc/hr, 0.9 M HCl) and a stream of 50/50 air/80° C. steam mixture (300 hr$^{-1}$ GHSV) to incorporate chlorine into the platinum-tin-potassium-alumina composite. The platinum-tin-potassium-chlorine-alumina composite was dried at 525° C. under a purge of dry air (1000 hr$^{-1}$ GHSV). The resulting catalyst spheres had an average particle diameter of 1/16 inch and were crushed and sized into 6-20 mesh particle before testing.

Stainless steel tubing, 1 inch OD, 0.6 inch ID and 26 inches long, was used as an isomerization reactor. A thermowell extended 20 inches from the top of the stainless steel reactor tube. To load the reactor tube, the reactor tube was inverted and a piece of glass wool was transferred down the wall of the reactor tube, over the thermowell and positioned at the bottom of the reactor tube to serve as a plug for the reactor tube. Silicon carbide (20 mesh) was added to a depth of about 6 inches to the reactor tube. A second piece of glass wool was placed over the silicon carbide. A mixture of 6.0 grams of platinum-tin on alumina catalyst particles (6-20 mesh) and 45 grams of fresh silicon carbide (60-80 mesh) was added to the reactor tube in two parts. The two-part addition distributed the catalyst evenly in the reactor tube and resulted in a catalyst bed of about 10 inches in length. A third piece of glass wool was added to the top of the catalyst in the reactor tube. Silicon carbide (20 mesh) was layered onto the third piece of glass wool. A fourth piece of glass wool was positioned over the silicon carbide to serve as a plug for the bottom of the reactor tube. To monitor the temperature of the reaction at various points in the reactor tube, a multipoint thermocouple was inserted into the thermowell of the reactor tube. The temperature above, below and at three different places in the catalyst bed was monitored. The reactor tube was inverted and installed in the furnace. The reactor tube was purged with nitrogen. The reactor tube was heated to the operating temperature of 425° C. over a four-hour period under flowing nitrogen (250 standard liters per hour). Once the temperature of 425° C. was obtained, the reactor tube was held at the operating temperature for an additional two hours. The catalyst was presulfided by flowing a 1% mixture of hydrogen sulfide gas in hydrogen gas at 425° C. for five minutes through the reactor tube. After 5 minutes, the hydrogen sulfide in hydrogen gas flow was switched to a hydrogen gas flow through the reactor tube.

After presulfiding the catalyst, the reactor tube was maintained at 425° C. for eight hours. After eight hours, the reactor tube pressure was increase to 25 psig with hydrogen gas. Dodecane was pumped through the reactor tube at a flow rate of 40 g/hr at a hydrogen flow rate of 125 standard liters per hour. After four hours, the dodecane stream was increased to 80 g/hr. After obtaining a flow rate of 80 g/hr, the reactor tube temperature was raised to 460° C. The reactor tube was sampled every eight hours after obtaining the operating temperature of 460° C.

After twenty-four hours the weight percent of dodecane was 11.4 weight percent as depicted in Table 6. At a temperature of 479° C., the conversion of dodecane to olefins was 16 weight percent after twenty-four hours. Of the olefins, formed 84 weight percent were mono olefins, 4.1 weight percent were aromatic compounds and 7.5 weight percent were di-olefins. Of the total amount of olefins formed, 6 percent were branched, as determined by $^1$H NMR analysis.

TABLE 6

Test Results.

| | |
|---|---|
| Conversion (wt. %) after 24 hours on-stream at 460° C. | 11.4 |
| Temperature required for 16 wt. % conversion | 479° C. |
| Selectivity to mono olefins at 16 wt. % conversion. | 84 wt. % |
| Selectivity to aromatics at 16 wt. % conversion. | 4.1 wt. % |
| Selectivity to di-olefins at 16 wt. % conversion. | 7.5 wt. % |
| % Branched $C_{12}$ olefins in total $C_{12}$ olefins, (wt. %) | 6 |

Example 4

Dehydrogenation-Isomerization of Dodecane

Dodecane was obtained from Aldrich Chemical Company and stored under nitrogen before being processed. The composition of dodecane, as assayed by gas chromatography, is tabulated in Table 5.

A dehydrogenation-isomerization catalyst was prepared in the following manner. Ammonium-ferrierite (645 grams) exhibiting a 5.4% loss on ignition and exhibiting the following properties: molar silica to alumina ratio of 62:1, surface area of 369 square meters per gram (P/Po=0.03), soda content of 480 ppm and n-hexane sorption capacity of 7.3 g per 100 g of ammonium-ferrierite was loaded into a Lancaster mix muller. CATAPAL® D alumina (91 grams) exhibiting a loss on ignition of 25.7% was added to the muller. During a five-minute mulling period, 152 milliliters of deionized water was added to the alumina/ammonium-ferrierite mixture. Next, a mixture of 6.8 grams glacial acetic acid, 7.0 grams of citric acid and 152 milliliters of deionized water was slowly added to the alumina/ammonium-ferrierite mixture in the muller to peptize the alumina. The resulting alumina/ammonium-ferrierite/acid mixture was mulled for 10 minutes. Over a period of 15 minutes, a mixture of 0.20 grams of tetraamine palladium nitrate in 153 grams of deionized water was slowly added to mulled alumina/ammonium-ferrierite/acid mixture. The resulting mixture exhibited a 90:10 ratio of zeolite to alumina and a loss on ignition of 43.5%. The zeolite/alumina mixture was shaped by extruding the mixture through a stainless steel die plate (1/16" holes) of a 2.25 inch Bonnot extruder.

Six grams of the resulting zeolite/alumina mixture was impregnated with an aqueous solution of sodium hexachloroplatinate [IV] hexahydrate to incorporate 0.8 wt. % platinum into the 1/16 inch extrudate. The moist zeolite/alumina platinum impregnated extrudate was dried at 125° C. for 2 hours in flowing air. The temperature was raised to a maximum temperature of 500° C. and the zeolite/alumina platinum impregnated extrudate was calcined to yield a dehydrogenation-isomerization catalyst. The calcined catalyst was crushed and sized into 6-20 mesh particles before testing.

Dodecane was dehydrogenated and isomerized using the same reactor tube design as described in Example 3. A 16.1 weight percent conversion of dodecane to olefins was observed after twenty-fours hours at 459° C. As tabulated in Table 7, of the olefins formed 86 weight percent were mono olefins, 1.2 weight percent were aromatic compounds and 6.8 weight percent were di-olefins. Of the total amount of olefins formed, 86 percent were branched, as determined by $^1$H NMR analysis.

TABLE 7

Test Results.

| | |
|---|---|
| Conversion (wt. %) after 24 hours on-stream at 460° C. | 16.1 |
| Temperature required for 16 wt. % conversion | 459° C. |
| Selectivity to mono olefins at 16 wt. % conversion. | 86 wt. % |
| Selectivity to aromatics at 16 wt. % conversion. | 1.2 wt. % |
| Selectivity to di-olefins at 16 wt. % conversion. | 6.8 wt. % |
| % Branched $C_{12}$ olefins in total $C_{12}$ olefins, (wt. %) | 86 |

Example 5

Dehydrogenation-Isomerization Catalyst

A zeolite portion of a dehydrogenation-isomerization catalyst was prepared as in Example 4. Six grams of the resulting zeolite/alumina mixture was impregnated with an aqueous solution of tetraamine palladium nitrate to incorporate 0.8 wt. % palladium into the 1/16 inch extrudates.

The moist zeolite/alumina palladium impregnated extrudate was dried at 125° C. for 2 hours in flowing air. The temperature was raised to a maximum temperature of 500° C. and the zeolite/alumina platinum impregnated extrudate was calcined to yield a dehydrogenation-isomerization catalyst. The calcined catalyst was carefully crushed and sized into 6-20 mesh particles before testing.

Example 6

Dehydrogenation-Isomerization Catalyst

A dehydrogenation-isomerization catalyst was prepared according to the method for catalyst D of U.S. Pat. No. 5,648,585 to Murray et al., entitled, "Process For Isomerizing Linear Olefins To Isoolefins", which is incorporated by reference herein.

Ammonium-ferrierite having a molar silica to alumina ratio of 62:1, a surface area of 369 m2/g (P/Po=0.03), a soda content of 480 ppm wt and a n-hexane sorption capacity of 7.3 grams per 100 grams of zeolite was used. The catalyst components were mulled using a Lancaster mix muller. The mulled catalyst material was extruded using a Bonnot pin barrel extruder. The binder utilized was CATAPAL® D alumina from Sasol. METHOCEL® F4M, hydroxypropyl methylcellulose, from The Dow Chemical Company was used as an extrusion aid.

The Lancaster mix muller was loaded with 632 grams of ammonium ferrierite (LOI of 3.4%) and 92 grams of CATAPAL®D alumina (LOI of 26.2%). The alumina was blended with the ferrierite for five minutes during which time 156 milliliters of de-ionized water was added. A mixture of 6.8 grams of glacial acetic acid and 156 milliliters of de-ionized water were added slowly to the muller in order to peptize the alumina. The mixture was mix-mulled for 10 minutes. Tetraamine platinum nitrate and Tetraamine palladium nitrate were added to the mix-muller in order to produce a catalyst that contained 0.25 wt. % palladium and 0.55 wt. % platinum. Ten grams of METHOCEL® F4M hydroxypropyl methylcellulose was added and the zeolite/alumina was mulled for 15 additional minutes. The extrudate was transferred to a Bonnot pin barrel extruder and extruded using a stainless steel die plate with 1/16 inch holes. The extrudate was dried at 120° C. for 16 hours and then calcined in air at 500° C. for 2 hours. The calcined catalyst was carefully crushed and sized into 6-20 mesh particles before testing.

Example 7

Dimerization of 1-Hexene

A dimerization catalyst for the dimerization of a $C_6$ olefin stream was prepared by the method for Example 1 in U.S. Pat. No. 5,169,824 to Saleh et al., entitled, "Catalyst Comprising Amorphous NiO On Silica/Alumina Support", which is incorporated by reference herein.

An aluminosilicate cogel (100 gram, 87% by weight $SiO_2$-13% by weight $Al_2O_3$) was dispersed in distilled water (2000 mL). Aluminosilicate cogel may be obtained from Ineos Silicas, Netherlands BV, as Synclist-13. Nitric acid (65%) was added to the aluminosilicate/water dispersion with stirring until a pH of 2.7 was obtained. The resulting acidic mixture was filtered and the aluminosilicate solid washed with distilled water until the filtrate exhibited a pH of 5.7. The recovered aluminosilicate solid was dispersed again in distilled water and nitric acid (65%) was added until a pH of 2.7 was obtained. The resulting acidic mixture was filtered and the resulting aluminosilicate solid was washed with distilled water until the filtrate exhibited a pH of 5.7. The recovered aluminosilicate solid was dried for 16 hours at 110° C. in an air atmosphere and thereafter calcined at 500° C. for 16 hours under an air atmosphere.

$Ni(NO_3)_2.6H_2O$ (67.38 gram) was dissolved in distilled water (700 mL) and heated to a temperature of 32° C. to result in a solution having a pH of 5.7. The aluminosilicate solid (35 gram) was added over time to the nickel solution resulting in a nickel/aluminosilicate slurry. The pH of the nickel/aluminosilicate slurry was approximately 3.9. The nickel/aluminosilicate slurry was neutralized by adding a solution of $(NH_4)_2CO_3$ (33.69 gram) in distilled water (200 mL) drop wise over 30 minutes until the pH of the slurry was approximately 6.9. The neutral slurry was stirred for 30 minutes at 32° C. and then filtered to obtain a solid. The recovered solid was slurried twice with water to the original volume of the nickel/aluminosilicate slurry, stirred for 5 minutes and then filtered to obtain a solid. The resulting solid was dried at 110° C. for 16 hours in an air atmosphere. Calcination of the solid was performed by heating the solid under an air atmosphere at increasing temperatures. Initially, the solid was heated to 232° C. for 1 hour. The temperature was raised to 371° C. and the solid heated for 2 hours. After 2 hours, the temperature was raised to 592° C. and the solid was heated for 16 hours. The resulting NiO catalyst dispersed on an aluminosilicate support was crushed and carefully sized to slightly greater than 60 mesh before testing.

A 15 mL reactor tube of an autoclave unit was charged with the NiO catalyst (0.335 grams), 1-hexene (3.35 grams), and a gas chromatography standard (0.67 grams linear tetradecane). Autoclave units of the type "Endeavour" from Argonaut Technologies, United Kingdom, were used to perform the dimerization experiments. The gas cap of the reactor tube was flushed with nitrogen and the reactor tube was heated to 160° C. Once the reaction temperature of 160° C. was obtained, the reaction temperature was maintained for 10 hours and then cooled to room temperature. The reaction mixture was filtered to remove the NiO catalyst and the filtrate was analysed by gas chromatography. The dimerization results are tabulated in Table 8.

TABLE 8

Test Results.

| | |
|---|---|
| Conversion of 1-hexene (%) | 59 |
| $C_{12}$ olefin dimer in reaction mixture (wt %) | 22 |
| Branched $C_{12}$ olefins in total $C_{12}$ olefins (wt. %) | 77 |

Example 8

Dimerization of Diluted 1-Hexene

A 15 mL reactor tube of the autoclave unit was charged with the NiO catalyst (0.335 grams) prepared according to the method for Example 7,1-hexene (1.675 grams), hexane (1.675 grams) and a gas chromatography standard (0.67 grams linear tetradecane). The gas cap of the reactor tube was flushed with nitrogen and the reactor tube was heated to 160° C. Once the reaction temperature of 160° C. was obtained, the reaction temperature was maintained for eight hours and then cooled to room temperature. The reaction mixture was filtered to remove the NiO catalyst and the filtrate was analyzed by gas chromatography. The dimerization results are tabulated in Table 9.

TABLE 9

Test Results.

| | |
|---|---|
| Conversion of 1-hexene (wt. %) | 54 |
| $C_{12}$ olefin dimer in reaction mixture (wt %) | 8 |
| % Branched $C_{12}$ olefins in total $C_{12}$ olefins | 82 |

In this patent, certain U.S. patents and U.S. patent applications have been incorporated by reference. The text of such U.S. patents and U.S. patent applications is, however, only incorporated by reference to the extent that no conflict exists between such text and the other statements and drawings set forth herein. In the event of such conflict, then any such conflicting text in such incorporated by reference U.S. patents and U.S. patent applications is specifically not incorporated by reference in this patent.

Further modifications and alternative embodiments of various aspects of the invention will be apparent to those skilled in the art in view of this description. Accordingly, this description is to be construed as illustrative only and is for the purpose of teaching those skilled in the art the general manner of carrying out the invention. It is to be understood that the forms of the invention shown and described herein are to be taken as examples of embodiments. Elements and materials may be substituted for those illustrated and described herein, parts and processes may be reversed, and certain features of the invention may be utilized independently, all as would be apparent to one skilled in the art after having the benefit of this description of the invention. Changes may be made in the elements described herein without departing from the spirit and scope of the invention as described in the following claims.

What is claimed is:

1. A method for the production of alphatic alcohols, comprising:
    introducing a Fischer-Tropsch hydrocarbon stream comprising olefins and paraffins, said Fischer-Tropsch hydrocarbon stream containing from 5 to 80 percent olefins having an average carbon number of from 10 to 17, into a dehydrogenation-isomerization unit, wherein the dehydrogenation-isomerization unit is configured to dehydrogenate at least a portion of the paraffins in the Fischer-Tropsch hydrocarbon stream to olefins, and wherein the dehydrogenation-isomerization unit is further configured to isomerize at least a portion of linear olefins to branched olefins in the presence of a dehydrogenation-isomerization catalyst comprising a hydrogen form of a zeolite having a ferrierite isotypic framework structure, and wherein the residence time is such that the conversion of paraffins to olefins is below 40 mole percent, and wherein at least a portion of the unreacted components of the Fischer-Tropsch hydrocarbon stream and at least a portion of the products of the dehydrogenation and isomerization reactions form a second hydrocarbon stream, the second hydrocarbon stream comprising olefins and paraffins, and wherein at least a portion of the olefins in the second hydrocarbon stream is branched olefins; and
    introducing at least a portion of the second hydrocarbon stream into a hydroformylation unit, wherein the hydroformylation unit is configured to hydroformylate at least a portion of the olefins in the second hydrocarbon stream to produce aliphatic alcohols having an average carbon number of from 11 to 18, and wherein at least a portion of the produced aliphatic alcohols comprises a branched alkyl group.

2. The method of claim 1, wherein the dehydrogenation-isomerization unit is operated at a temperature range from about 300° C. to about 500° C.

3. The method of claim 1, wherein the dehydrogenation-isomerization unit is configured to operate at a pressure range from about 0.10 atmosphere to about 15 atmospheres.

4. The method of claim 1, wherein a portion of the branched olefins comprises an average number of branches per total olefin molecules of at least 0.7.

5. The method of claim 1, wherein a portion of the branched olefins comprises methyl and ethyl branches.

6. The method of claim 1, wherein a portion of the branched olefins comprises an average number of branches per total olefin molecules of less than 2.5.

7. The method of claim 1, wherein a portion of the branched olefins comprises an average number of branches per total olefin molecules from about 0.7 to about 2.2.

8. The method of claim 1, wherein a portion of the branched olefins comprises an average number of branches per total olefin molecules of from about 1.0 to about 2.2.

9. The method of claim 1, wherein greater than 50 percent of the branched groups on the branched olefins are methyl groups.

10. The method of claim 1, wherein less than 30 percent of the branched groups on the branched olefins are ethyl groups.

11. The method of claim 1, wherein less than 10 percent of the branched groups on the branched olefins are neither methyl or ethyl groups.

12. The method of claim 1, wherein the branched olefins have less than 0.5 percent aliphatic quaternary carbon atoms.

13. The method of claim 1, wherein the branched olefins have less than 0.3 percent aliphatic quaternary carbon atoms.

14. The method of claim 1, further comprising:
    introducing at least a portion of the second hydrocarbon stream into a separation unit, wherein the separation unit is configured to separate at least a portion of the branched olefins from linear olefins and paraffins to form a linear olefins and paraffins stream and a branched olefins stream;

combining at least a portion of the linear olefins and paraffins stream with the Fischer-Tropsch hydrocarbon stream upstream of the dehydrogenation-isomerization unit; and combining at least a portion of the branched olefins stream with the second hydrocarbon stream upstream of the hydroformylation unit.

15. The method of claim 1, wherein the aliphatic alcohols produced by the hydroformylation unit comprise greater than 50 percent of the total hydrocarbon content of the hydroformylation reaction stream.

16. The method of claim 1, wherein the hydroformylation unit is operated at a reaction temperature from about 100° C. to about 300° C.

17. The method of claim 1, further comprising adjusting a ratio of olefins to paraffins introduced into the hydroformylation unit by adding at least a portion of a third hydrocarbon stream into the hydroformylation unit.

18. The method of claim 1, further comprising adjusting a ratio of olefins to paraffins introduced into the hydroformylation unit by adding at least a portion of a third hydrocarbon stream into the hydroformylation unit, wherein the third hydrocarbon stream comprises greater than 80 percent olefins by weight.

19. The method of claim 1, further comprising adjusting a ratio of olefins to paraffins introduced into the hydroformylation unit by combining at least a portion of a third hydrocarbon stream with at least a portion of the second hydrocarbon stream upstream of the hydroformylation unit and introducing the combined stream into the hydroformylation unit.

20. The method of claim 1, further comprising: adjusting a ratio of olefins to paraffins introduced into the hydroformylation unit by combining at least a portion of a third hydrocarbon stream with at least a portion of the second hydrocarbon stream upstream of the hydroformylation unit, wherein the third hydrocarbon stream comprises greater than 80 percent olefins by weight; and introducing the mixed stream into the hydroformylation unit.

21. The method of claim 1, wherein the branched alkyl groups of the aliphatic alcohols comprise 0.5 percent or less aliphatic quaternary carbon atoms, and an average number of branches per alkyl group of at least 0.7, the branches comprising methyl and ethyl branching.

22. The method of claim 1, further comprising:
separating aliphatic alcohols from the hydroformylation reaction stream to produce at least a paraffins and unreacted olefins stream and an aliphatic alcohols product stream; and
introducing at least a portion of the paraffins and unreacted olefins stream into the dehydrogenation-isomerization unit.

23. The method of claim 22, wherein introducing at least a portion of the paraffins and unreacted olefins stream into the dehydrogenation-isomerization unit comprises: combining at least a portion of the paraffins and unreacted olefins stream with at least a portion of the Fischer-Tropsch hydrocarbon stream to produce a combined stream upstream of the dehydrogenation-isomerization unit; and introducing at least a portion of the combined stream into the dehydrogenation-isomerization unit.

24. The method of claim 1, wherein the dehydrogenation-isomerization unit comprises a dehydrogenation-isomerization catalyst which additionally comprises a binder, a coke-oxidizing compound, and a paraffin dehydrogenation promoting compound.

25. The method of claim 24, wherein the coke-oxidizing compound comprises chrome oxide, iron oxide, noble metals, or mixtures thereof.

26. The method of claim 24, wherein the coke-oxidizing compound comprises a platinum, palladium, iridium, ruthenium, osmium, rhodium, or mixtures thereof.

27. The method of claim 24, wherein the coke-oxidizing compound is a noble metal.

28. The method of claim 24, wherein the paraffin dehydrogenation promoting compound is a noble metal.

29. The method of claim 24, wherein the paraffin dehydrogenation promoting compound is platinum.

30. The method of claim 24, wherein the binder is selected from natural clays, alumina, and silica-alumina.

31. The method of claim 24, wherein the binder is alumina.

32. The method of claim 1, wherein the dehydrogenation-isomerization unit comprises a plurality of zones, wherein the plurality of zones comprises a first reaction zone and a second reaction zone, wherein the first reaction zone is configured to dehydrogenate at least a portion of paraffins to olefins, and wherein the second reaction zone is configured to isomerize at least a portion of linear olefins to branched olefins, and wherein at least a portion of the unreacted components of the Fischer-Tropsch hydrocarbon stream and at least a portion of the products of the dehydrogenation and isomerization reactions form a second hydrocarbon stream.

33. The method of claim 1, wherein the dehydrogenation-isomerization unit comprises a plurality of zones, wherein the plurality of zones comprises a first reaction zone and a second reaction zone, wherein the first reaction zone is configured to dehydrogenate at least a portion of paraffins to olefins, wherein the second reaction zone is configured to isomerize at least a portion of linear olefins to branched olefins; and wherein the first reaction zone is operated at a temperature of between about 300° C. and about 600° C.

34. The method of claim 1, wherein the dehydrogenation-isomerization unit comprises a plurality of zones, wherein the plurality of zones comprises a first reaction zone and a second reaction zone, wherein the first reaction zone is configured to dehydrogenate at least a portion of paraffins to olefins, wherein the second reaction zone is configured to isomerize at least a portion of linear olefins to branched olefins; and wherein the first reaction zone is operated at a temperature of between about 450° C. and about 550° C.

35. The method of claim 1, wherein the dehydrogenation-isomerization unit comprises a plurality of zones, wherein the plurality of zones comprises a first reaction zone and a second reaction zone, wherein the first reaction zone is configured to dehydrogenate at least a portion of paraffins to olefins, wherein the second reaction zone is configured to isomerize at least a portion of linear olefins to branched olefins; and wherein the first reaction zone is operated at a total reaction pressure between about 0.01 atmospheres and about 25.0 atmospheres.

36. The method of claim 1, further comprising introducing hydrogen into the Fischer-Tropsch hydrocarbon stream.

37. The method of claim 1, wherein the dehydrogenation-isomerization unit comprises a plurality of zones, wherein the plurality of zones comprises a first reaction zone and a second reaction zone, wherein the first reaction zone is configured to dehydrogenate at least a portion of paraffins to olefins, and wherein the second reaction zone is configured to isomerize at least a portion of linear olefins to branched olefins.

38. The method of claim 37, further comprising introducing at least a portion of the first hydrocarbon stream exiting the first reaction zone into a heat exchanger, wherein the heat exchanger is configured to remove heat from a portion of the Fischer-Tropsch hydrocarbon stream before it enters the second reaction zone.

39. The method of claim 1, wherein the dehydrogenation-isomerization unit comprises a plurality of zones, wherein the plurality of zones comprises a first reaction zone and a second reaction zone, wherein the first reaction zone is configured to dehydrogenate at least a portion of paraffins to olefins, wherein the second reaction zone is configured to isomerize at least a portion of linear olefins to branched olefins; and wherein the second reaction zone is operated at a temperature range from about 200° C. to about 500° C.

40. The method of claim 1, wherein the dehydrogenation-isomerization unit comprises a plurality of zones, wherein the plurality of zones comprises a first reaction zone and a second reaction zone, wherein the first reaction zone is configured to dehydrogenate at least a portion of paraffins to olefins, wherein the second reaction zone is configured to isomerize at least a portion of linear olefins to branched olefins; and wherein the second reaction zone is operated at a hydrocarbon partial pressure of from about 0.1 atmosphere to about 10 atmospheres.

41. The method of claim 1, wherein the dehydrogenation-isomerization unit comprises a stacked bed catalyst configuration, wherein the stacked bed comprises a dehydrogenation catalyst and an isomerization catalyst.

42. The method of claim 1, further comprising introducing at least a portion of the produced aliphatic alcohols into a sulfation unit, wherein the sulfation unit is configured to sulfate at least a portion of the produced aliphatic alcohols to produce aliphatic sulfates, and wherein at least a portion of the aliphatic sulfates produced comprise branched aliphatic sulfates.

43. The method of claim 1, further comprising introducing at least a portion of the produced aliphatic alcohols into an oxyalkylation unit, wherein the oxyalkylation unit is configured to oxyalkylate at least a portion of the produced aliphatic alcohols to produce oxyalkyl alcohols, wherein at least a portion of the oxyalkyl alcohols produced comprises branched oxyalkyl alcohols.

44. The method of claim 1, further comprising:
forming an hydroformylation reaction stream wherein the hydroformylation reaction stream comprises at least a portion of the unreacted components of the second hydrocarbon stream and at least a portion of the produced aliphatic alcohols; and
separating produced aliphatic alcohols from the hydroformylation reaction stream to produce a paraffins and unreacted olefins stream and an aliphatic alcohol product stream.

45. The method of claim 44, further comprising introducing at least a portion of the paraffins and unreacted olefins stream into the dehydrogenation-isomerization unit.

46. A method for the production of aliphatic alcohols comprising:
introducing a Fischer-Tropsch hydrocarbon stream comprising olefins and paraffins, said Fischer-Tropsch hydrocarbon stream containing from 5 to 80 percent olefins having an average carbon number of from 10 to 17, into a hydrogenation unit, wherein the hydrogenation unit is configured to hydrogenate at least a portion of olefins in the first hydrocarbon stream to paraffins, and wherein at least a portion of the unreacted components of the Fischer-Tropsch hydrocarbon stream and at least a portion of the hydrogenated olefins form a second hydrocarbon stream,
introducing the second hydrocarbon stream into a dehydrogenation-isomerization unit, wherein the dehydrogenation-isomerization unit is configured to dehydrogenate at least a portion of the paraffins in the second hydrocarbon stream to olefins, and wherein the dehydrogenation-isomerization unit is further configured to isomerize at least a portion of linear olefins to branched olefins in the presence of a dehydrogenation-isomerization catalyst comprising a hydrogen form of a zeolite having a ferrierite isotypic framework structure, and wherein the residence time is such that the conversion of paraffins to olefins is below 40 mole percent, and wherein at least a portion of the unreacted components of the second hydrocarbon stream and at least a portion of the products of the dehydrogenation and isomerization reactions form a third hydrocarbon stream, the third hydrocarbon stream comprising olefins and paraffins, and wherein at least a portion of the olefins in the third hydrocarbon stream are branched olefins; and
introducing at least a portion of the third hydrocarbon stream into a hydroformylation unit, wherein the hydroformylation unit is configured to hydroformylate at least a portion of the olefins in the third hydrocarbon stream to produce aliphatic alcohols having an average carbon number of from 11 to 18, and wherein at least a portion of the produced aliphatic alcohols comprises a branched alkyl group.

47. The method of claim 46, wherein the hydrogenation unit is operated at a temperature range from about 175° C. to about 250° C.

48. The method of claim 46, wherein the hydrogenation unit is operated at a hydrogen flow rate between about 250 NL/L/hr and about 5000 NL/L/hr.

49. The method of claim 46, wherein the hydrogenation unit is operated at a pressure range from about 10 atmospheres to about 50 atmospheres.

50. The method of claim 46, wherein the dehydrogenation-isomerization unit is operated at a temperature range from about 300° C. to about 500° C.

51. The method of claim 46, wherein the dehydrogenation-isomerization unit is configured to operate at a pressure range from about 0.010 atmosphere to about 15 atmospheres.

52. The method of claim 46, wherein a portion of the branched olefins comprises an average number of branches per total olefin molecules of at least 0.7.

53. The method of claim 46, wherein a portion of the branched olefins comprises methyl and ethyl branches.

54. The method of claim 46, wherein a portion of the branched olefins comprises an average number of branches per total olefin molecules of less than 2.5.

55. The method of claim 46, wherein a portion of the branched olefins comprises an average number of branches per total olefin molecules from about 0.7 to about 2.2.

56. The method of claim 46, wherein a portion of the branched olefins comprises an average number of branches per total olefin molecules from about 1.0 to about 2.2.

57. The method of claim 46, wherein greater than 50 percent of the branched groups on the branched olefins are methyl groups.

58. The method of claim 46, wherein less than 30 percent of the branched groups on the branched olefins are ethyl groups.

59. The method of claim 46, wherein less than 10 percent of the branched groups on the branched olefins are neither methyl or ethyl groups.

60. The method of claim 46, wherein the branched olefins have less than 0.5 percent aliphatic quaternary carbon atoms.

61. The method of claim 46, wherein the branched olefins have less than 0.3 percent aliphatic quaternary carbon atoms.

62. The method of claim 46, wherein the hydroformylation unit is configured to produce greater than 50 percent of aliphatic alcohols.

63. The method of claim 46, wherein the hydroformylation unit is configured to produce greater than 95 percent of aliphatic alcohols.

64. The method of claim 46, wherein the hydroformylation unit is operated at a reaction temperature range from about 100° C. to about 300° C.

65. The method of claim 46, wherein the branched alkyl groups of the aliphatic alcohols comprise about 0.5 percent or less aliphatic quaternary carbon atoms, and an average number of branches per alkyl group of at least 0.7, the branches comprising methyl and ethyl branching.

66. The method of claim 46, further comprising:
forming a hydroformylation reaction stream comprising at least a portion of the unreacted components of the third hydrocarbon stream, and at least a portion of the produced aliphatic alcohol;
separating aliphatic alcohols from the hydroformylation reaction stream to produce a paraffins and unreacted olefins stream and an aliphatic alcohol product stream;
introducing at least a portion of the paraffins and unreacted olefins stream into the dehydrogenation-isomerization unit.

67. The method of claim 66, wherein introducing at least a portion of the paraffins and unreacted olefins stream into the dehydrogenation-isomerization unit comprises combining at least a portion of the paraffins and unreacted olefins stream with at least a portion of the second hydrocarbon stream to produce a combined stream upstream of the dehydrogenation-isomerization unit and introducing at least a portion of the combined stream into the dehydrogenation-isomerization unit.

68. The method of claim 46, further comprising introducing at least a portion of the produced aliphatic alcohols into a sulfation unit, wherein the sulfation unit is configured to sulfate at least a portion of the aliphatic alcohols to produce aliphatic sulfates; wherein at least a portion of the aliphatic sulfates produced comprises branched aliphatic sulfates.

69. The method of claim 46, further comprising introducing at least a portion of the produced aliphatic alcohols into an oxyalkylation unit, wherein the oxyalkylation unit is configured to oxyalkylate at least a portion of the produced aliphatic alcohols to produce oxyalkyl alcohols, wherein at least a portion of the oxyalkyl alcohols produced comprises branched oxyalkyl alcohols.

70. The method of claim 46, further comprising:
introducing at least a portion of the produced aliphatic alcohols into an oxyalkylation unit, wherein the oxyalkylation unit is configured to oxyalkylate at least a portion of the produced aliphatic alcohols to produce an oxyalkyl alcohol stream, wherein at least a portion of the oxyalkyl alcohols produced comprises branched oxyalkyl alcohols; and
introducing at least a portion of the oxyalkyl alcohol stream into a sulfation unit, wherein the sulfation unit is configured to sulfate at least a portion of the oxyalkyl alcohols in the oxyalkyl alcohol stream to produce oxyalkyl sulfates, wherein at least a portion of the oxyalkyl sulfates produced comprises branched oxyalkyl sulfates.

71. The method of claim 46, wherein the dehydrogenation-isomerization unit comprises a dehydrogenation-isomerization catalyst additionally comprising a binder, a coke-oxidizing compound, and a paraffin dehydrogenation promoting compound.

72. The method of claim 71, wherein the coke-oxidizing compound comprises chrome oxide, iron oxide, noble metals, or mixtures thereof.

73. The method of claim 71, wherein the coke-oxidizing compound comprises a platinum, palladium, iridium, ruthenium, osmium, rhodium, or mixtures thereof.

74. The method of claim 71, wherein the coke-oxidizing compound is a noble metal.

75. The method of claim 71, wherein the paraffin dehydrogenation promoting compound is a noble metal.

76. The method of claim 71, wherein the paraffin dehydrogenation promoting compound is platinum.

77. The method of claim 71, wherein the binder is selected from natural clays, alumina, and silica-alumina.

78. The method of claim 71, wherein the binder is alumina.

79. The method of claim 46, wherein the dehydrogenation-isomerization unit comprises a plurality of zones, wherein the plurality of zones comprises a first reaction zone and a second reaction zone, wherein the first reaction zone is configured to dehydrogenate at least a portion of paraffins to olefins, and wherein the second reaction zone is configured to isomerize at least a portion of linear olefins to branched olefins, and wherein at least a portion of the unreacted components of the first hydrocarbon stream and at least a portion of the products of the dehydrogenation and isomerization reactions form a second hydrocarbon stream.

80. The method of claim 46, wherein the dehydrogenation-isomerization unit comprises a plurality of zones, wherein the plurality of zones comprises a first reaction zone and a second reaction zone, wherein the first reaction zone is configured to dehydrogenate at least a portion of paraffins to olefins, and wherein the second reaction zone is configured to isomerize at least a portion of linear olefins to branched olefins; and wherein the first reaction zone is operated in a temperature range of from about 300° C. to about 600° C.

81. The method of claim 46, wherein the dehydrogenation-isomerization unit comprises a plurality of zones, wherein the plurality of zones comprises a first reaction zone and a second reaction zone, wherein the first reaction zone is configured to dehydrogenate at least a portion of paraffins to olefins, and wherein the second reaction zone is configured to isomerize at least a portion of linear olefins to branched olefins, and wherein the first reaction zone is operated in a temperature range of from about 450° C. to about 550° C.

82. The method of claim 46, wherein the dehydrogenation-isomerization unit comprises a plurality of zones, wherein the plurality of zones comprises a first reaction zone and a second reaction zone, wherein the first reaction zone is configured to dehydrogenate at least a portion of paraffins to olefins, and wherein the second reaction zone is configured to isomerize at least a portion of linear olefins to branched olefins and wherein the first reaction zone is operated at a total reaction pressure between about 0.01 atmospheres and about 25.0 atmospheres.

83. The method of claim 46, further comprising introducing hydrogen into the first hydrocarbon stream.

84. The method of claim 46, wherein the dehydrogenation-isomerization unit comprises a plurality of zones, wherein the plurality of zones comprises a first reaction zone and a second reaction zone, wherein the first reaction zone is configured to dehydrogenate at least a portion of paraffins to olefins, wherein the second reaction zone is configured to isomerize at least a portion of linear olefins to branched olefins.

85. The method of claim 84, further comprising introducing at least a portion of the first hydrocarbon stream exiting the first reaction zone into a heat exchanger, wherein the heat exchanger is configured to remove heat from a portion of said hydrocarbon stream exiting the first reaction zone before it enters the second reaction zone.

86. The method of claim 46, wherein the dehydrogenation-isomerization unit comprises a plurality of zones, wherein the plurality of zones comprises a first reaction zone and a second reaction zone, wherein the first reaction zone is configured to dehydrogenate at least a portion of paraffins to olefins, wherein the second reaction zone is configured to isomerize at least a portion of linear olefins to branched olefins; and wherein the second reaction zone is operated in a temperature range of from about 200° C. to about 500° C.

87. The method of claim 46, wherein the dehydrogenation-isomerization unit comprises a plurality of zones, wherein the plurality of zones comprises a first reaction zone and a second reaction zone, wherein the first reaction zone is configured to dehydrogenate at least a portion of paraffins to olefins, wherein the second reaction zone is configured to isomerize at least a portion of linear olefins to branched olefins; and wherein the second reaction zone is operated at a hydrocarbon partial pressure between about 0.1 atmosphere and about 10 atmospheres.

88. The method of claim 46, wherein the dehydrogenation-isomerization unit comprises a stacked bed catalyst configuration, wherein the stacked bed catalyst comprises a dehydrogenation catalyst and an isomerization catalyst.

* * * * *